(12) United States Patent
Krammer et al.

(10) Patent No.: US 10,227,620 B2
(45) Date of Patent: Mar. 12, 2019

(54) METHOD FOR BIOTECHNOLOGICAL PRODUCTION OF METHYLIZED CINNAMIC ACIDS AND CINNAMIC ACID ESTERS, METHYLIZED PHENETHYLAMINES AND THE COUPLING PRODUCTS THEREOF, PARTICULARLY OF CINNAMIC ACID AMIDES

(71) Applicant: SYMRISE AG, Holzminden (DE)

(72) Inventors: Gerhard Krammer, Holzminden (DE); Jakob Peter Ley, Holzminden (DE); Katrin Geißler, Einbeck (DE); Torsten Geißler, Einbeck (DE); Frauke Gomoll, St. Ingbert (DE); Peter Welters, Nettetal (DE); Guido Jach, Nettetal (DE); Ludger Wessjohann, Halle (DE)

(73) Assignee: SYMRISE AG, Holzminden (DE)

( * ) Notice: Subject to any disclaimer, the term of this patent is extended or adjusted under 35 U.S.C. 154(b) by 240 days.

(21) Appl. No.: 15/011,855

(22) Filed: Feb. 1, 2016

(65) Prior Publication Data
US 2016/0281118 A1 Sep. 29, 2016

(30) Foreign Application Priority Data
Jan. 30, 2015 (EP) ..................... 15153218

(51) Int. Cl.
| | |
|---|---|
| *C12N 9/10* | (2006.01) |
| *C12P 7/22* | (2006.01) |
| *C12P 7/40* | (2006.01) |
| *C12P 7/42* | (2006.01) |
| *C12P 7/62* | (2006.01) |
| *A23L 27/20* | (2016.01) |
| *A23L 27/24* | (2016.01) |
| *C12P 13/00* | (2006.01) |
| *C12P 13/02* | (2006.01) |

(52) U.S. Cl.
CPC ............ *C12P 13/02* (2013.01); *A23L 27/204* (2016.08); *A23L 27/24* (2016.08); *C12N 9/1007* (2013.01); *C12N 9/1085* (2013.01); *C12P 7/22* (2013.01); *C12P 7/40* (2013.01); *C12P 7/42* (2013.01); *C12P 7/62* (2013.01); *C12P 13/001* (2013.01); *C12Y 201/01* (2013.01); *C12Y 205/01006* (2013.01); *A23V 2002/00* (2013.01)

(58) Field of Classification Search
None
See application file for complete search history.

(56) References Cited

U.S. PATENT DOCUMENTS

| | | |
|---|---|---|
| 2013/0078683 A1 | 3/2013 | Loque et al. |
| 2014/0370568 A1 | 12/2014 | Liu et al. |

FOREIGN PATENT DOCUMENTS

WO WO-2014128252 A1 8/2014

OTHER PUBLICATIONS

Kopycki, J.G. et al.: "Functional and Structural Characterization of a Cation-dependent 0-Methyltransferase from the *Cyanobacterium synechocystis* sp. Strain PCC 6803", Journal of Biological Chemistry, Bd. 283, Nr. 30, May 23, 2008 (May 23, 2008), Seiten 20888-20896, XP002743302.

Kim, D.H. et al.: "Regiospecific methylation of naringenin to ponciretin by soybean 0-methyltransferase expressed in *Escherichia coli*", Journal of Biotechnology, Bd. 119, Nr. 2, Sep. 23, 2005 (Sep. 23, 2005), Seiten 155-162, XP027663506.

McFarlane, I.J. & Slaytor, M.: "Alkaloid Biosynthesis in Echinocereus Merkeri", Phytochemistry, Bd. 11, Nr. 1, 1972, Seiten 235-238, XP026609831.

Nelson, T.N. et al.: "Characterization of SafC, a Catechol 4-0-Methyltransferase Involved in Saframycin Biosynthesis", Applied and Environmental Microbiology, Bd. 73, Nr. 11, Apr. 20, 2007 (Apr. 20, 2007), Seiten, 3575-3580, XP002743303.

Adesina, S.K. & Reisch, J.: "Amides From, Zanthoxylum Rubescens", Phytochemistry, Bd. 28, Nr. 3, 1989, Seiten 839-842, XP026616404.

Friedhoff, A.J.: "Biosynthesis of DMPEA, and its Metabolites in Mammalian Tissues", Biological Psychiatry, Bd. 6, Nr. 2, Apr. 1973 (Apr. 1973), Seiten, 187-191, XP008178433.

Database UniProt [Online] Jan. 7, 2015 (Jan. 7, 2015), Schroder, G. et al.: "RecName: Full=Caffeic acid 3-0-methyltransferase; Short=CAOMT; Short=COMT; EC=2.1.1.68", XP002752112.

Database EMBL [Online] Apr. 16, 2005 (Apr. 16, 2005), Schroder, G. et al:: "Catharanthus roseus caffeic acid 0-methyltransferase (ComT1) mRNA, complete cds", XP002752113.

Database UniProt [Online] Jan. 7, 2015 (Jan. 7, 2015), Ma, Q.J. & Xu, Y.: "AltName: Full=Caffeic, acid 3-0-methyltransferase; Short=TaCM", XP002752114.

Database EMBL [Online] Jun. 23, 2006 (Jun. 23, 2006), Zhou, J.M. et al: "Triticum aestivum flavonoid 0-methyltransferase mRNA, complete cds", XP002752115.

European Search Report issued in EP Application No. 15153218.1, dated Jan. 18, 2016.

Partial European Search Report issued in EP Application No. 15153218.1, dated Aug. 31, 2015.

*Primary Examiner* — Anand U Desai
(74) *Attorney, Agent, or Firm* — Polsinelli PC

(57) ABSTRACT

The invention relates to providing both fermentative and biotechnological methods for producing 3,4-methylized cinnamic acids, 3,4-methylized cinnamic acid esters, 3,4-dimethoxyphenethylamine, and 4-methylized cinnamic acid amides using a 4'-O-methyltransferase, optionally in combination with further enzymes, wherein the enzymes are selected by means of metabolic engineering and operation have been adapted by targeted optimization, and compositions obtained by means of the method.

The invention further relates to vector systems, recombinant microorganisms or fungi, and specific nucleic acid segments and polypeptides.

15 Claims, 18 Drawing Sheets
Specification includes a Sequence Listing.

| | |
|---|---|
| Kaffeesäure | Caffeic acid |
| Ferulasäure | Ferulic acid |
| O-Methyltransferase | O-methyltransferase |
| DOPA-Decarboxylase | DOPA decarboxylase |
| Dopamin | Dopamine |
| Lipase oder | Lipase or |
| Co-Ligase + THT | Co-Ligase + THT |
| 3,4-Dimethoxyzimtsäure | 3,4-dimethoxycinnamic acid |
| O-Methyltransferase | O-methyltransferase |
| Rubemamin | Rubemamine |

| Enzyme | ferulic acid [%] | 3,4-dimethoxycinnamic acid [%] |
|---|---|---|
| CbMOMT (SEQ ID NO:27) | 12.0 | 88.0 |
| CbMOMT-L322N (SEQ ID NO:28) | 0.8 | 99.2 |
| CbMOMT-T133S (SEQ ID NO:29) | 44.9 | 55.1 |
| CbMOMT-T133S/L322N (SEQ ID NO:86) | 65.2 | 34.8 |

Figure 18

METHOD FOR BIOTECHNOLOGICAL PRODUCTION OF METHYLIZED CINNAMIC ACIDS AND CINNAMIC ACID ESTERS, METHYLIZED PHENETHYLAMINES AND THE COUPLING PRODUCTS THEREOF, PARTICULARLY OF CINNAMIC ACID AMIDES

TECHNOLOGICAL FIELD

The present invention relates to both fermentative and biotechnical methods for producing 3,4-methylated cinnamic acids, 3,4-methylated cinnamic acid esters, 3,4-dimethyloxyphenethylamines, and 4-methylated cinnamic acid amides using a 4'-O-methyltransferase optionally in combination with an S-adenosylmethionine synthase or a 3'-O-methyltransferase and further enzymes.

The present invention further relates to vector systems and recombinant microorganisms or fungi able to code/express the enzymes for performing the present invention and nucleic acid segments and polypeptides suitable for the same. The present invention further relates to compositions obtained by means of the method according to the present invention.

BACKGROUND OF THE INVENTION

In the field of industrial production of flavoring agents there is a continuous demand for efficient and cost-effective means for synthesizing said flavoring agents. Methylized cinnamic acids and cinnamic acid esters, methylized phenethylamine, and the coupling products thereof, particularly cinnamic acid amides, are examples of such flavoring agents. One exemplary cinnamic acid amide is rubemamine. Rubemamine was identified as a natural material in the plant *Zanthoxylum rubescens*. Currently, however, no biotechnical method for producing said special substance and the direct precursors thereof has been described.

It is known from the prior art that caffeic acid is converted by means of various caffeoyl-CoA-O-methyltransferases (CcAOMT) or cathechol-O-methyltransferases (COMT) and transgenic microorganisms forming a CcAOMT or COMT (Fellenberg, C. et al. Tapetum-specific location of a cation-dependent O-methyltransferase in *Arabidopsis thaliana*. *Plant J.* 56, 132-45 (2008); Ibdah, M., Zhang, X.-H., Schmidt, J. & Vogt, T. A novel Mg(2+)-dependent O-methyltransferase in the phenylpropanoid metabolism of *Mesembryanthemum crystallinum*. *J. Biol. Chem.* 278, 43961-72 (2003)). The 3' position is always thereby modified and exclusively ferulic acid is formed. The methylization of the 4' position has previously been demonstrated only for monolignoles and phenylpropanoids using a variant of (iso) eugenolmethyltransferase from *Clarkia breweri* (U.S. Pat. No. 8,889,392 B2, Zhang, K. et al. An engineered monolignol 4-O-methyltransferase depresses lignin biosynthesis and confers novel metabolic capability in *Arabidopsis*. *Plant Cell* 24, 3135-52 (2012)) and by means of further O-methyltransferases on phenylpropenes such as chavicol or eugenol (Gang, D. R. et al. Characterization of Phenylpropene O-Methyltransferases from Sweet Basil: Facile Change of Substrate Specificity and Convergent Evolution within a Plant O-Methyltransferase Family. *Plant Cell* 14, 505-519 (2002). A method for enzymatically permethylizing phenethylamines such as dopamine, 3-methoxytyramine, or 3-hydroxy-4-methoxy-phenethylamine is not known. Converting L-DOPA to dopamine by means of DOPA-decarboxylases and by means of transgenic microorganisms producing said enzymes has been described (Facchini et al. Plant aromatic L-amino acid decarboxylases: evolution, biochemistry, regulation, and metabolic engineering applications. *Phytochemistry* 54, 121-38 (2000)). Modifying the resulting dopamine by means of 3'-O-methyltransferases (3-OMTs) is also known, wherein 3-methoxytyramine is formed as a product (Lotta, T. et al. Kinetics of Human Soluble and Membrane-Bound Catechol O-Methyltransferase: A Revised Mechanism and Description of the Thermolabile Variant of the Enzyme. *Biochemistry* 34, 4202-4210 (1995)). It has further been demonstrated that 4-methoxytyramine is also produced from the deltaproteobacterium *Myxococcus xanthus* from dopamine by the activity of the enzyme SafC (Nelson, J. T., Lee, J., Sims, J. W. & Schmidt, E. W. Characterization of SafC, a catechol 4-O-methyltransferase involved in saframycin biosynthesis. *Appl. Environ. Microbiol.* 73, 3575-80 (2007)). Permethylization starting with dopamine, 3-methoxytyramine, and/or 3-hydroxy-4-methoxytyramine and forming 3,4-dimethyoxyphenethylamine, however, has not been demonstrated, neither by enzymatic conversion nor by biotransformation using transgenic microorganisms or fungi.

It was further known that S-adenosylmethionine synthases (SAMSs) can be used for producing S-adenosylmethionine (SAM). The combined expression of O-methyltransferases using S-adenosylmethionine-synthases for improved provision of the cofactor S-adenosylmethionine has previously be demonstrated only for forming flavonoids (Sung, S. H. Optimization of Rhamnetin Production in *Escherichia coli*. *J. Microbiol. Biotechnol.* 21, 854-857 (2011)), but not for forming methylized cinnamic acids and phenethylamines. The forming of coenzyme A esters of cinnamic acid by the activity of 4-coumarate:CoA ligases is also known (Lindermayr, C. et al. Divergent members of a soybean (*Glycine max* L.) 4-coumarate:coenzyme A ligase gene family. *Eur. J. Biochem.* 1315, 1304-1315 (2002)). Ligation of the formed CoA esters using the amines by means of tyramine-N-hydroxycinnamoyltransferases, however, has been previously demonstrated only for non-permethylized substrates such as ferulic acid and dopamine (Yu, M. & Facchini, P. J. Purification, characterization, and immunolocalization of hydroxycinnamoyl-CoA:Tyramine N-(hydroxycinnamoyl)transferase from opium poppy. *Planta* 209, 33-44 (1999)). No synthesis method starting with cinnamic acids and L-DOPA is known. Further, the methods known under the prior art do not include any biotechnical method for producing cinnamic acid amides in the sense of the present invention, particularly no method suitable for industrial production of cinnamic acid amides, as the yields are estimated to be very small (e.g., 215 mg/L in Kang, K. & Back, K. Production of phenylpropanoid amides in recombinant *Escherichia coli*. *Metab. Eng.* 11, 64-68 (2009)).

Therefore a need for establishing biotechnical methods has arisen, that is, both fermentative and enzymatic methods comprising the use of a recombinant organism at least in one step and being suitable for industrial application, in order to thereby reproducibly provide methylized cinnamic acids and phenethylamines and derivatives and coupling products thereof at a sufficient scale.

SUMMARY OF THE INVENTION

The object of the present invention is therefore to make available both fermentative and enzymatic biotechnological methods and the necessary recombinant organisms, nucleic acid segments, polypeptides, and vector systems, by means of which (i) methylized cinnamic acids and cinnamic acid esters, (ii) methylized phenethylamines, and (iii) cinnamic acid amides, such as rubemamine, can be produced at large scale using amide coupling, that is, the combining of biosynthesis paths from (i) and (ii) at different levels of said synthesis paths.

Said objects are achieved by providing biotechnological methods and tools necessary therefor for producing natural 3,4-methylized cinnamic acids, 3,4-methylized cinnamic acid esters, 3,4-dimethoxyphenethylamine, and cinnamic acid amides in a recombinant microorganism or fungus using at least one 4'-O-methyltransferase. Further enzymes that have been established by metabolic engineering and that can be used for said biotechnological methods comprise an S-adenosylmethionine-synthase or a 3'-O-methyltransferase and optionally a decarboxylase, a 4-courmarat:CoA-ligase (CL) and a tyramine-N-hydroxycinnamoyltransferase (THT). The reaction can be either completely fermentative, or fermentative and enzymatic, or completely enzymatic, with the stipulation that an enzyme produced by means of one of the methods according to the invention is always used. Further disclosed are suitable recombinant microorganisms and fungi and vector systems, nucleic acid segments, and polypeptides suitable for performing a method according to the present invention.

In a first aspect of the present invention, starting with a hydroxycinnamic acid or a hydroxycinnamic acid esterified on a hemicellulose, a 3,4-methylized cinnamic acid or a 3,4-methylized cinnamic acid ester is obtained using a 4'-O-methyltransferase (4-OMT) and optionally additionally a 3'-O-methyltransferase (3-OMT) and an S-adenosylmethionine-synthase (SAMS).

In one embodiment of said consideration the conversion can be purely fermentative. In a further embodiment, the final conversion of the reactants is enzymatic.

In a second consideration of the present invention, starting with dopamine and/or L-dihydroxyphenylalanine or a precursor or a derivative thereof, 3,4-dimethoxyphenethylamine is obtained using a 4-OMT and 3-OMT.

In one embodiment of said consideration the conversion can be purely fermentative. In a further embodiment, the final conversion of the reactants is enzymatic.

In a third consideration of the present invention, starting with a hydroxycinnamic acid or a hydroxycinnamic acid esterified on a hemicellulose and with dopamine and/or L-dihydroxyphenylalanine or a precursor or a derivative thereof, a 4-methylized cinnamic acid amide is obtained using a 4-OMT, a 4-coumarat:CoA-ligase (CL), and a tyramine-N-hydroxycinnamoyltransferase (THT) and optionally further polypeptides, or nucleic acids coding said polypeptides.

In one embodiment of said consideration the conversion can be entirely fermentative. In a further embodiment, the final conversion of the reactants is enzymatic.

In one embodiment of said aspect the amide coupling for fermentative conversion can take place using a CL and a THT. In a further embodiment the amide coupling takes place for enzymatic conversion by means of a lipase. The enzymatic step of the amide coupling can thereby be catalyzed by a lipase.

In a further embodiment of said aspect, the amide coupling takes place in an arbitrary sequence relative to the reaction steps of the 4'-O-methylization and the optional 3'-methylization.

Further disclosed are recombinant microorganisms and fungi bearing the vectors necessary for performing the method according to the invention or a vector system and thus coding the nucleic acids for performing the methods according to the invention.

Further disclosed are nucleic acid segments and polypeptides specially suited for using the methods disclosed herein.

Further, a composition comprising the products of the method according to the invention according to aspect three are provided.

Aspects and embodiments of the present invention result from the following detailed description and the examples, the figures, the sequence record, and the attached claims.

BRIEF DESCRIPTION OF THE DRAWINGS

FIG. 18 shows a comparison of the conversion of ferulic acid to 3,4-diemthoxycinnamic acid by means of the CbMOMT and by means of the mutants produced thereby.

FULL DESCRIPTION

Definitions

Figure 1:
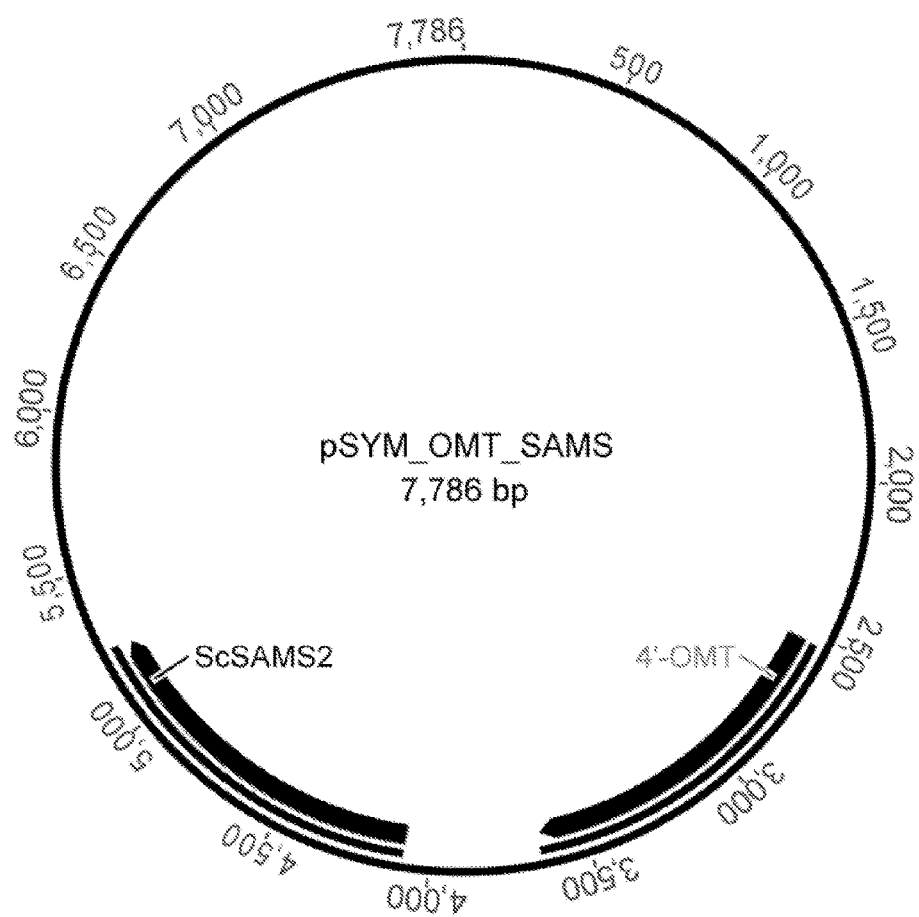
FIG. 1 shows the plasmid SYM_OMT_SAMS with genes that code for a 4'-O-methyltransferase and the S-adenosylmethionine synthase.
Figure 2:
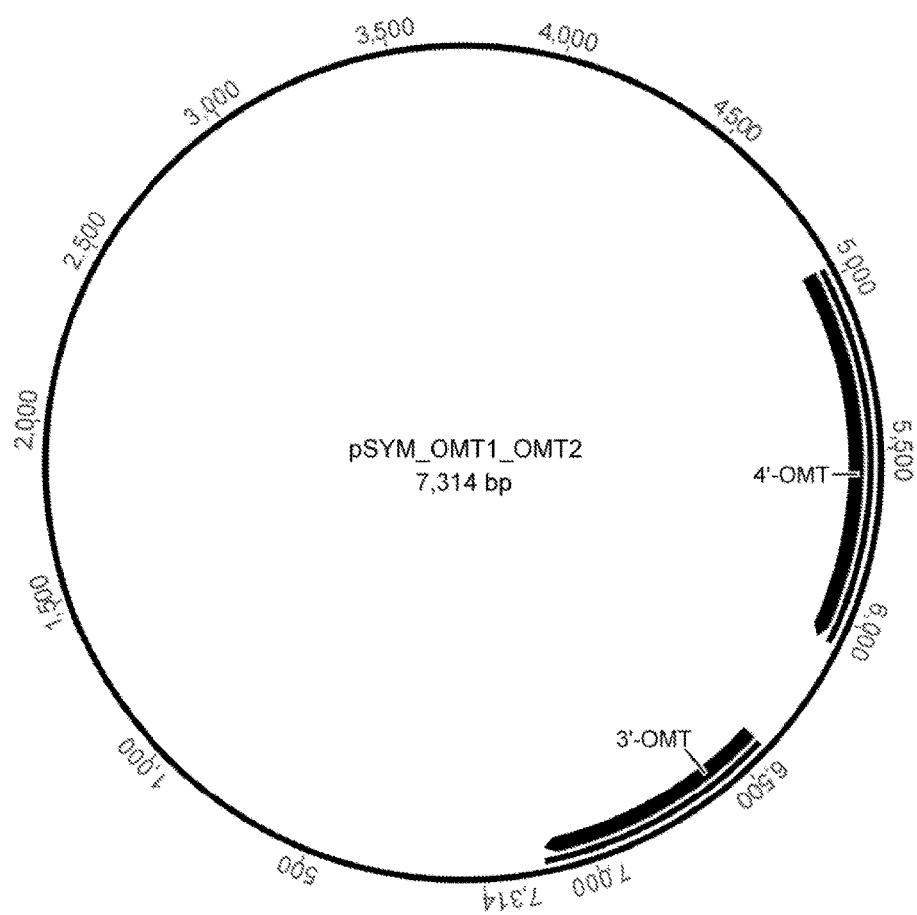
FIG. 2 shows the plasmid pSYM_OMT1_OMT2 with genes that code for the 3'-O-methyltransferase and the 4'-O-methyltransferase.
Figure 3:
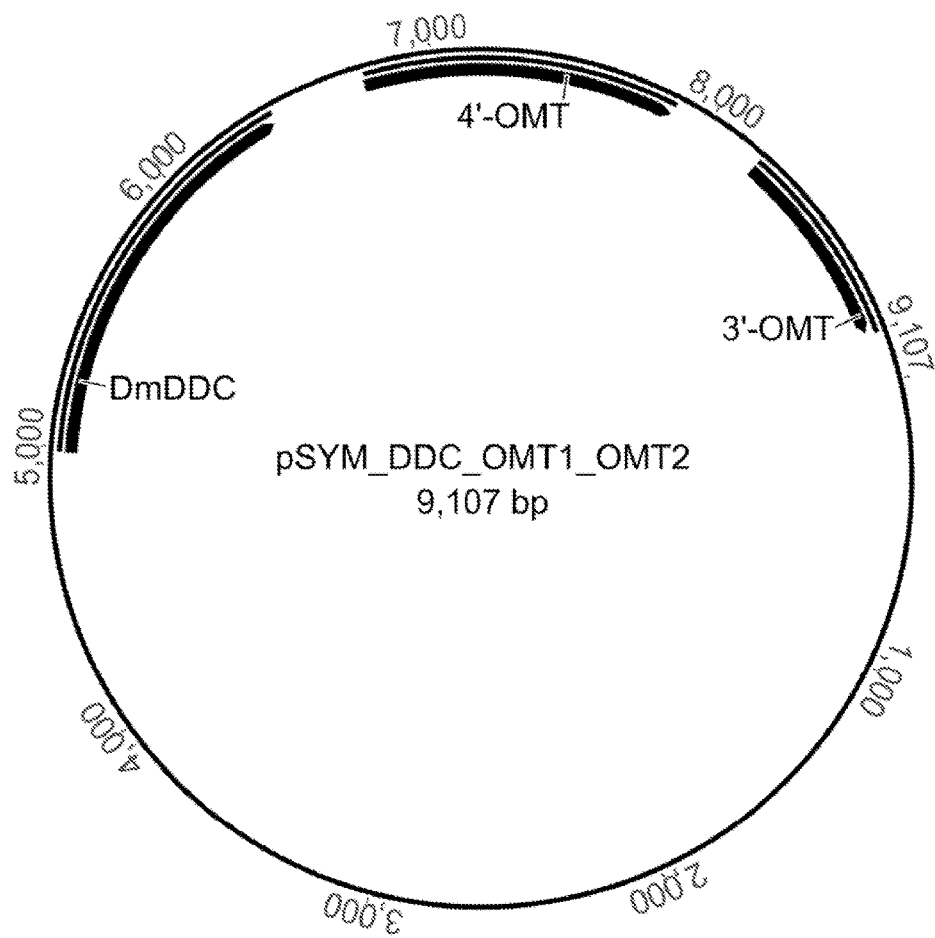
FIG. 3 shows the plasmid pSYM_DDC_OMT1_OMT2 with genes that code for a decarboxylase, a 3'-O-methyltransferase, and a 4'-O-methyltransferase.
Figure 4:
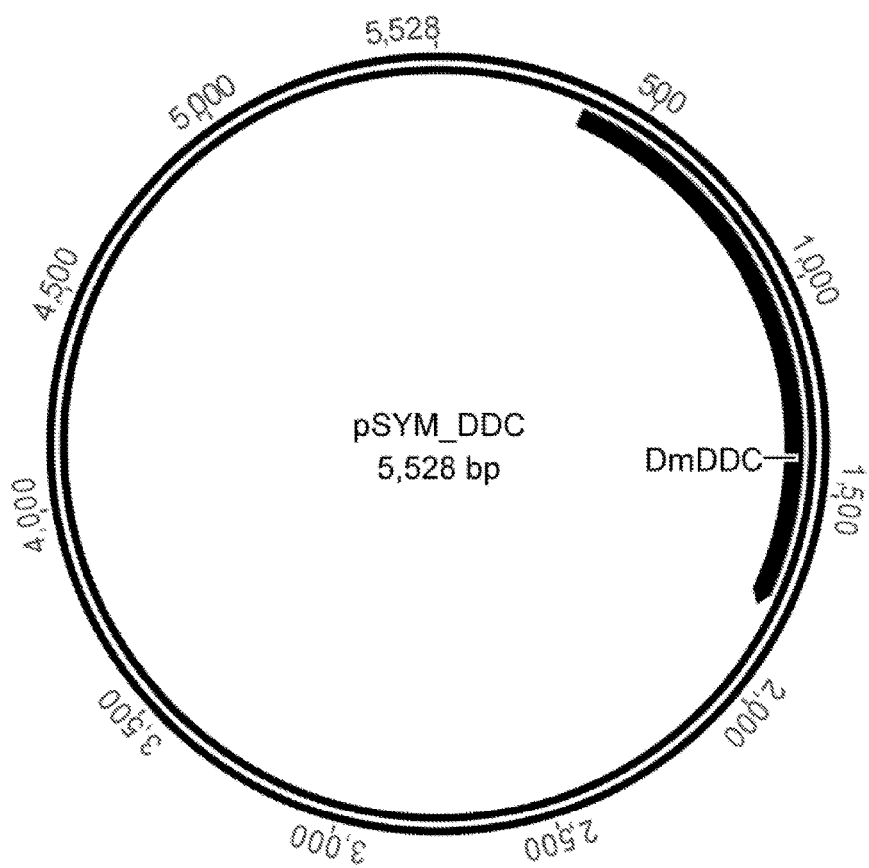
FIG. 4 shows the plasmid pSYM_DDC with a gene that codes for a decarboxylase.
Figure 5:
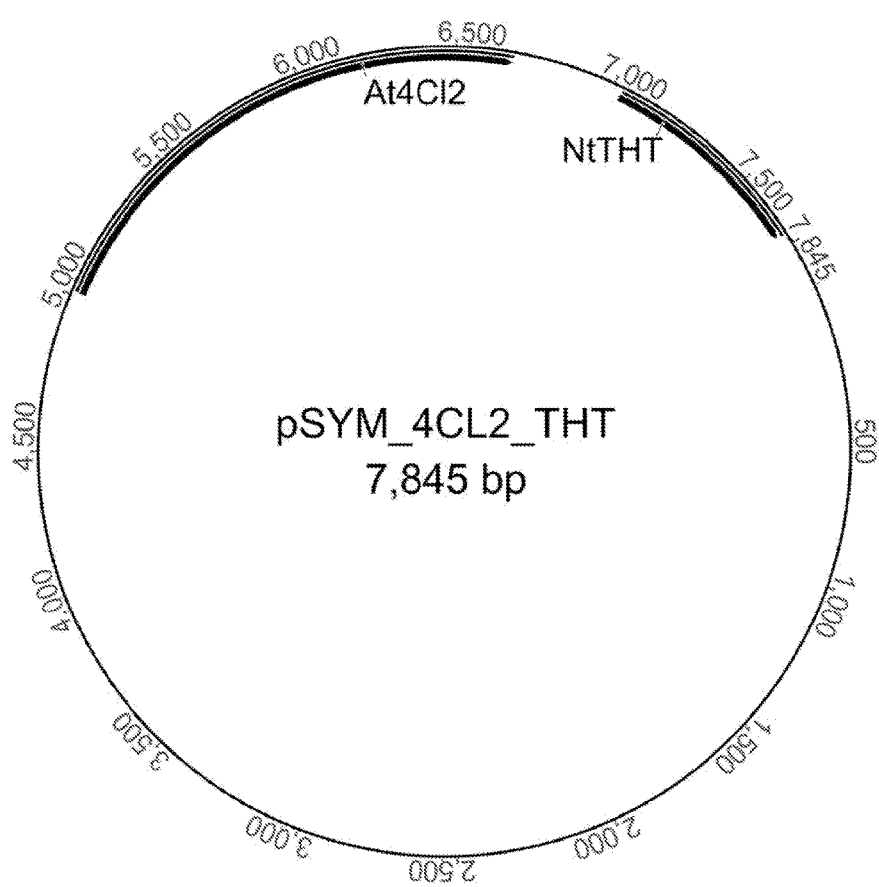
FIG. 5 shows the plasmid pSYM_4 CL2_THT with genes that code for a 4-coumarat:CoA-ligase and a tyramine-N-hydroxycinnamoyltransferase.
Figure 6:
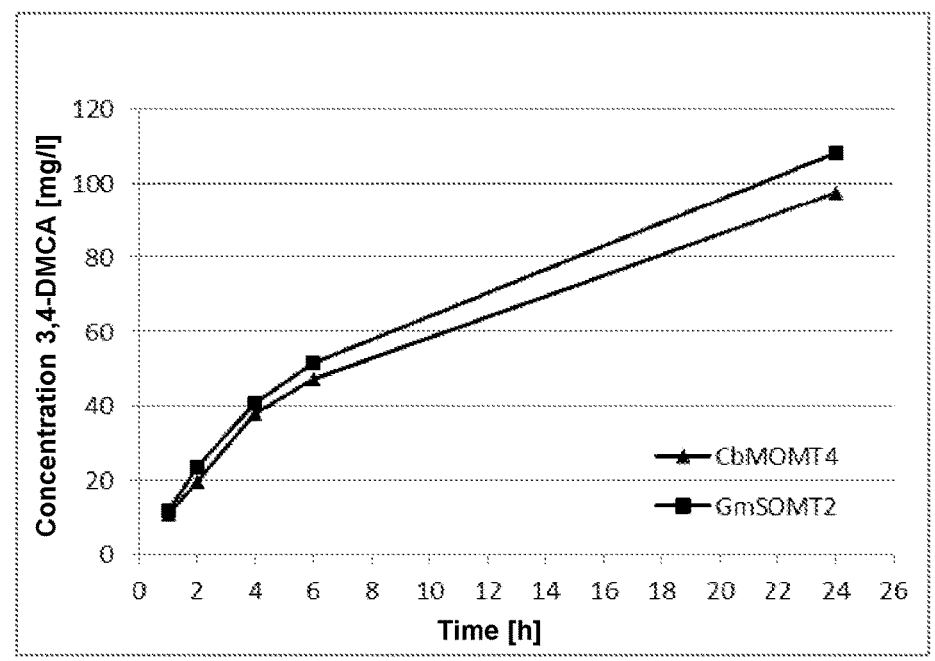
FIG. 6 shows the biocatalytic conversion of ferulic acid to 3,4-dimethoxycinnamic acid.
Figure 7:
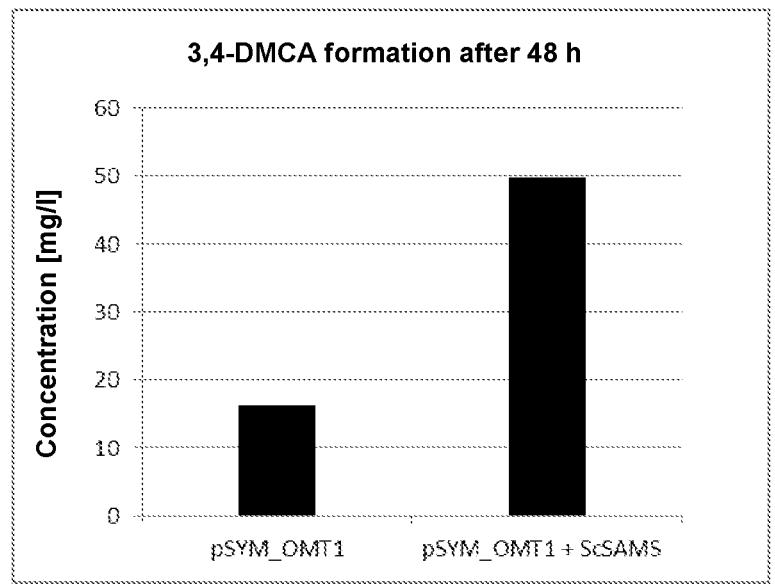
FIG. 7 shows the increased formation of 3,4-dimethoxycinnamic acid by means of joint expression of an O-methyltransferase with an S-adenosylmethionine synthase.
Figure 8:
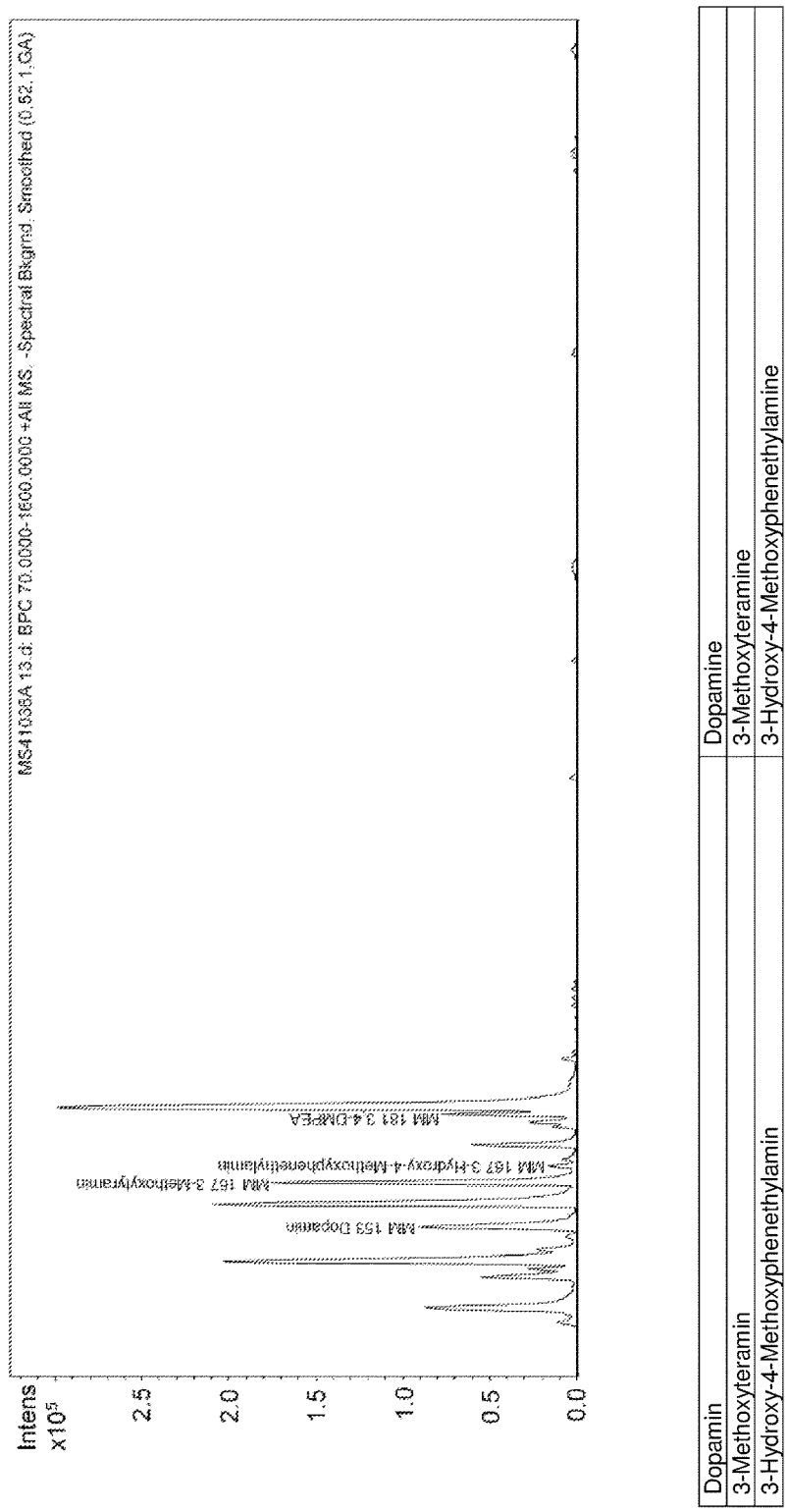
FIG. 8 shows an LC-MS chromatogram of an enzymatic conversion of L-DOPA to 3,4-diemthoxyphentyhlamine.
Figure 9:
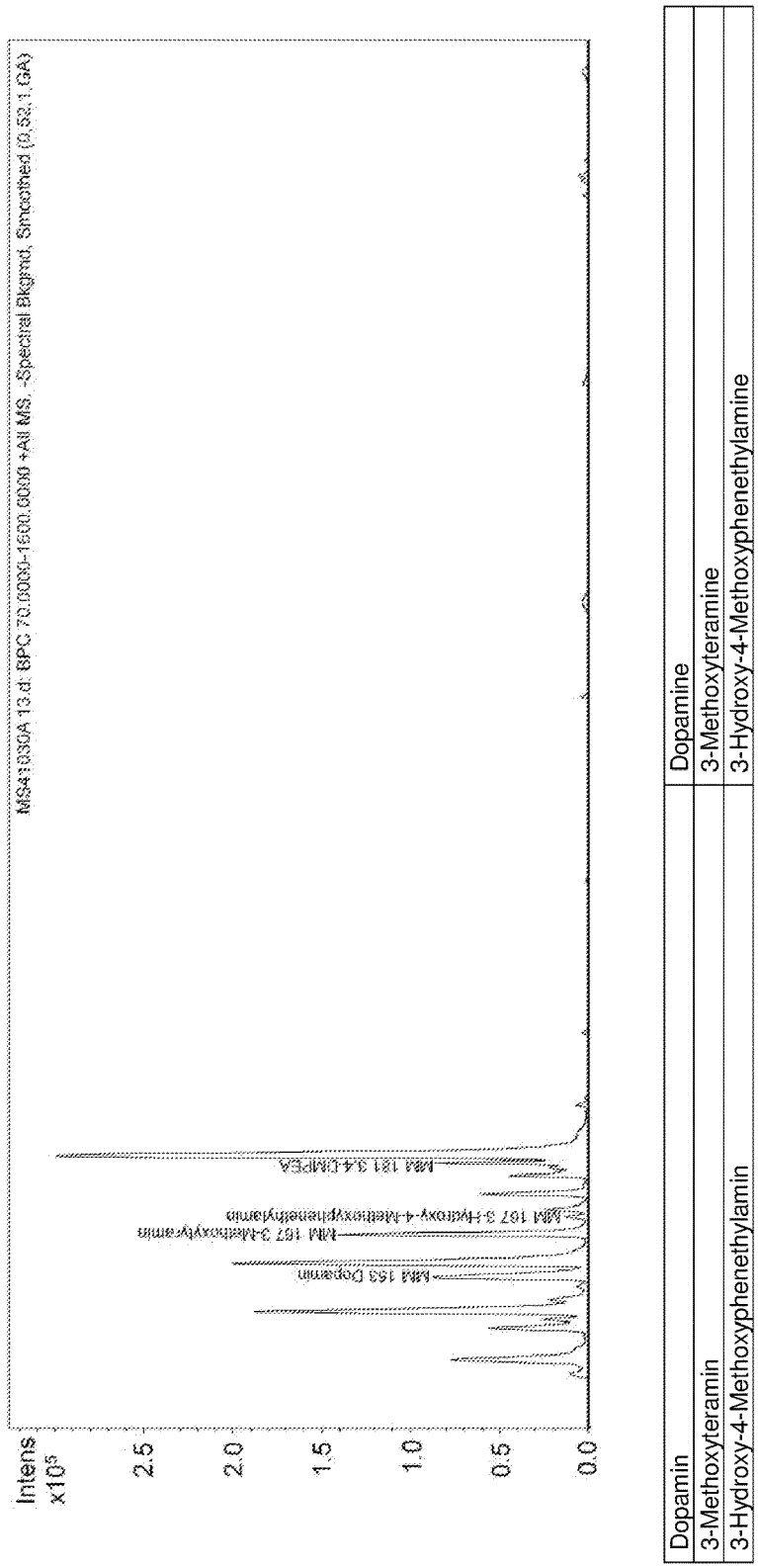
FIG. 9 shows an LC-MS chromatogram of an enzymatic conversion of dopamine 3,4-diemtoxyphentyhlamine.
Figure 10:
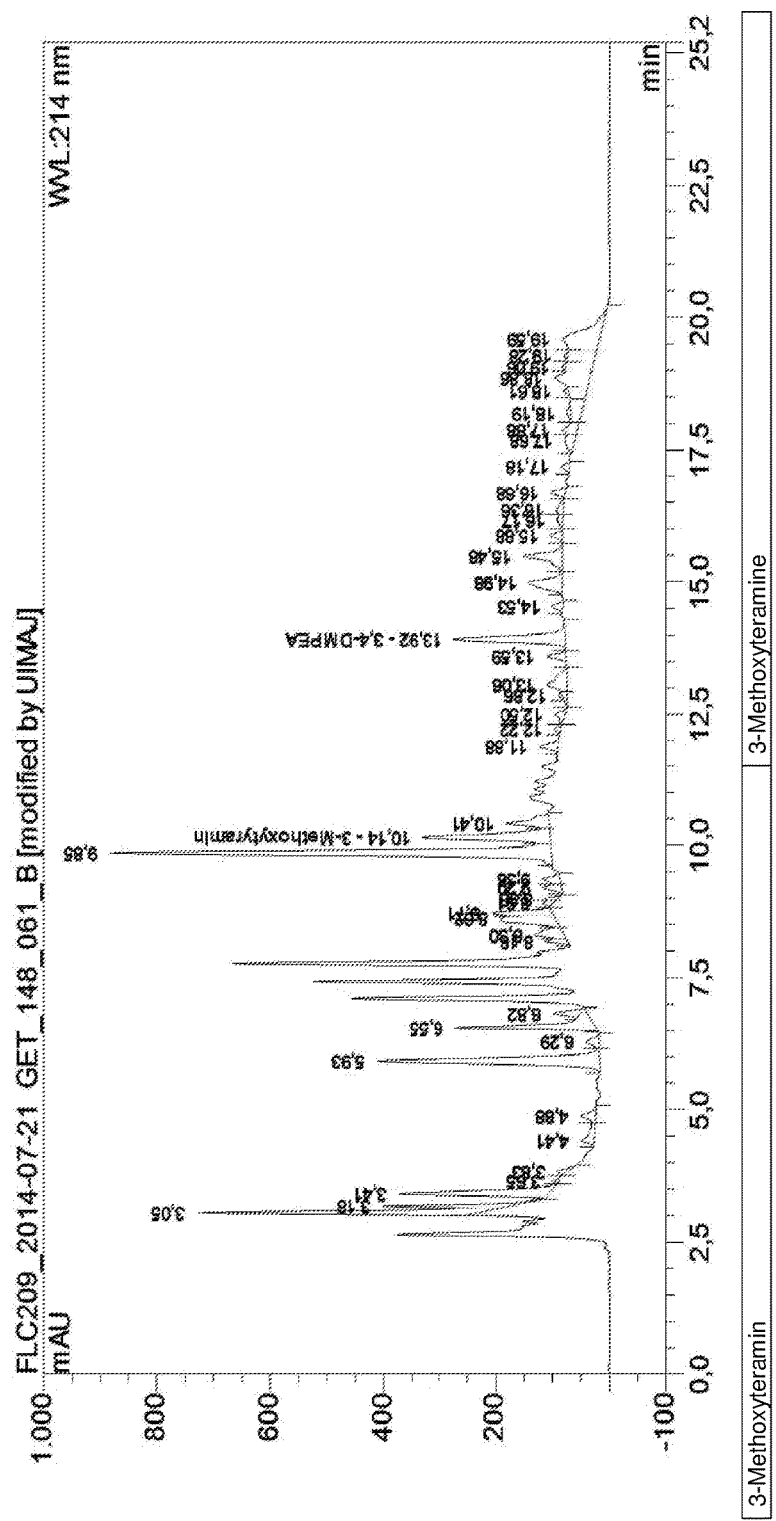
FIG. 10 shows an HPLC chromatogram of a fermentative conversion of L-DOPA to 3,4-dimethoxyphenethylamine.
Figure 11:
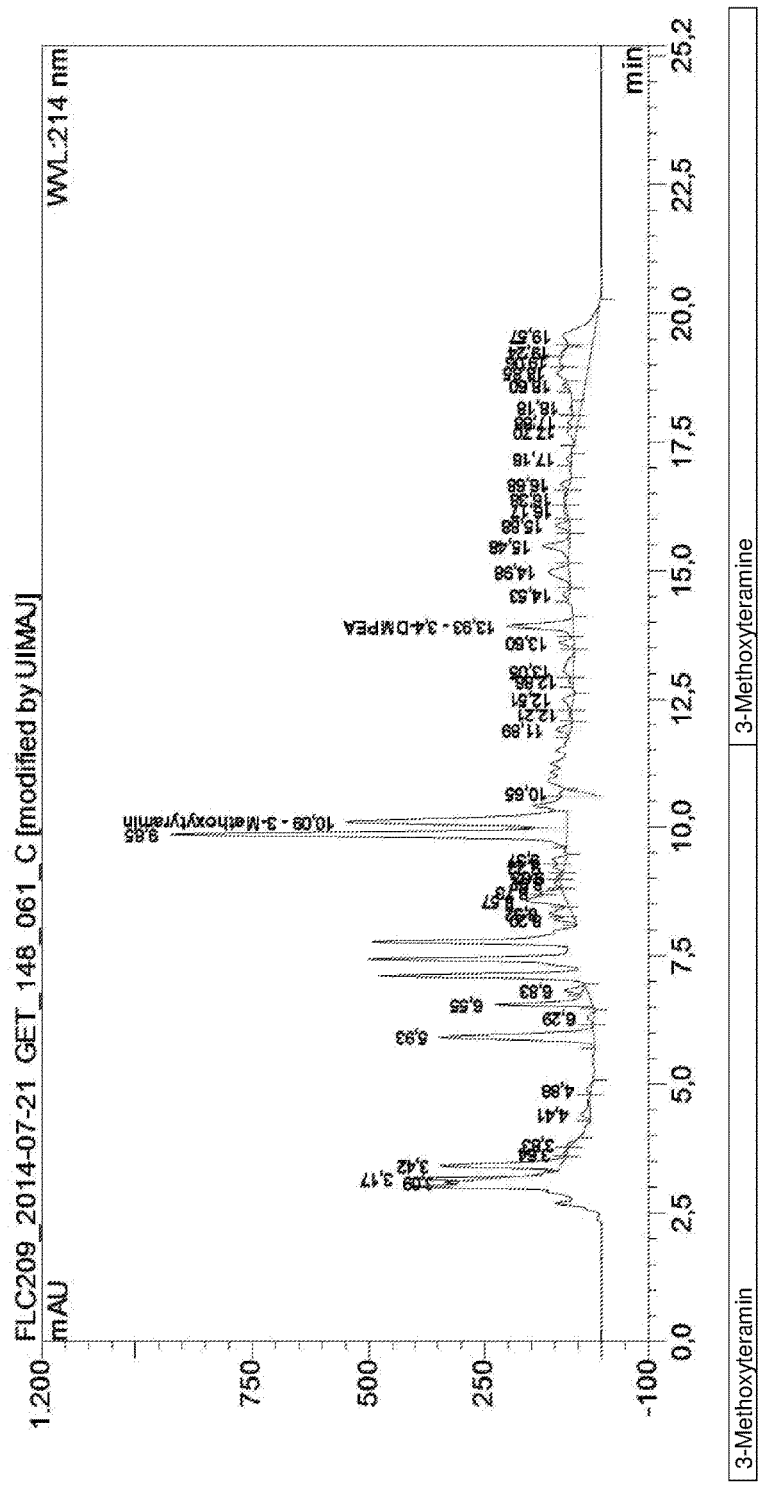
FIG. 11 shows an HPLC chromatogram of a fermentative conversion of dopamine to 3,4-dimethoxyphenethylamine.
Figure 12:
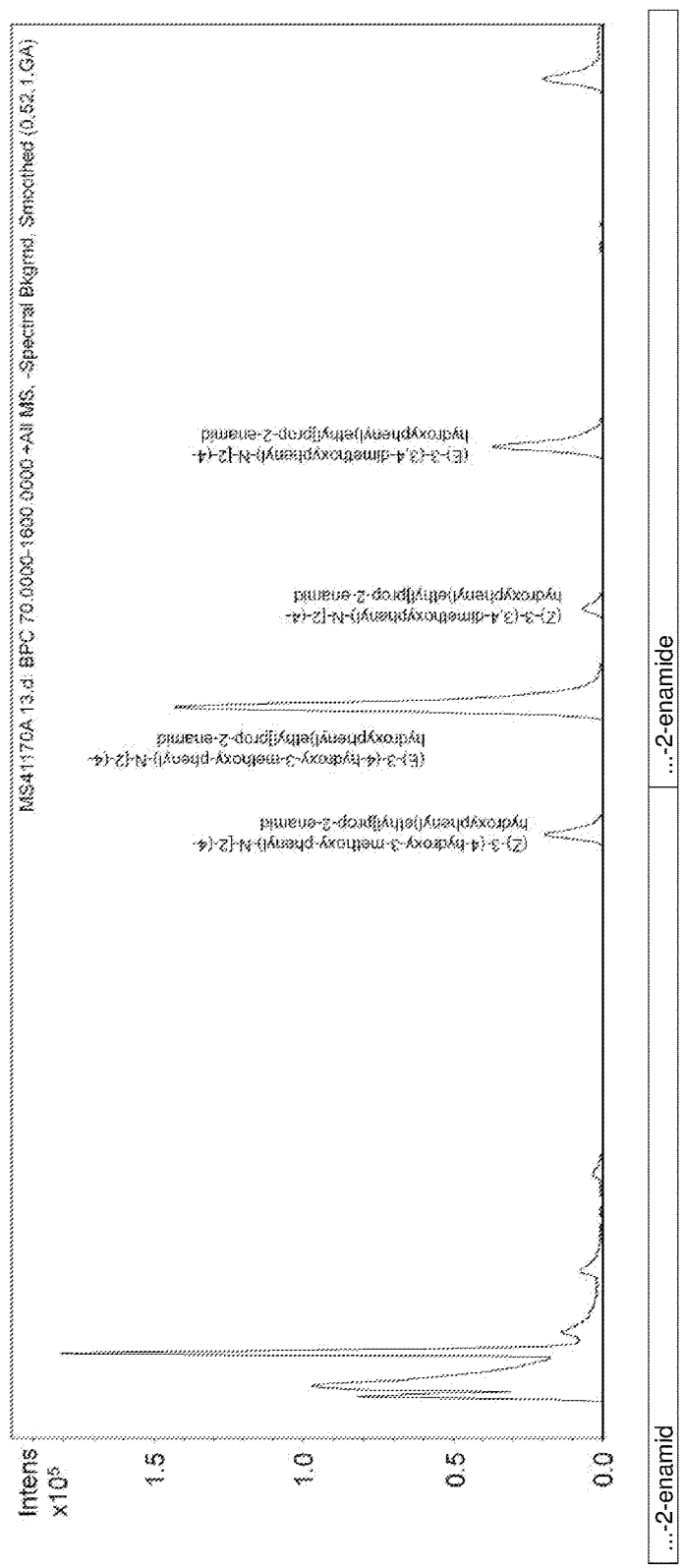
FIG. 12 shows an LC-MS chromatogram of an enzymatic conversion of (E)-3-(4-hydroxy-3-methoxy-phenyl)-N-[2-(4-hydroxyphenyl)ethyl]prop-2-enamide to (E)-3-(3,4-dimethoxyphenyl)-N-[2-(4-hydroxyphenyl)ethyl]prop-2-enamide.
Figure 13:
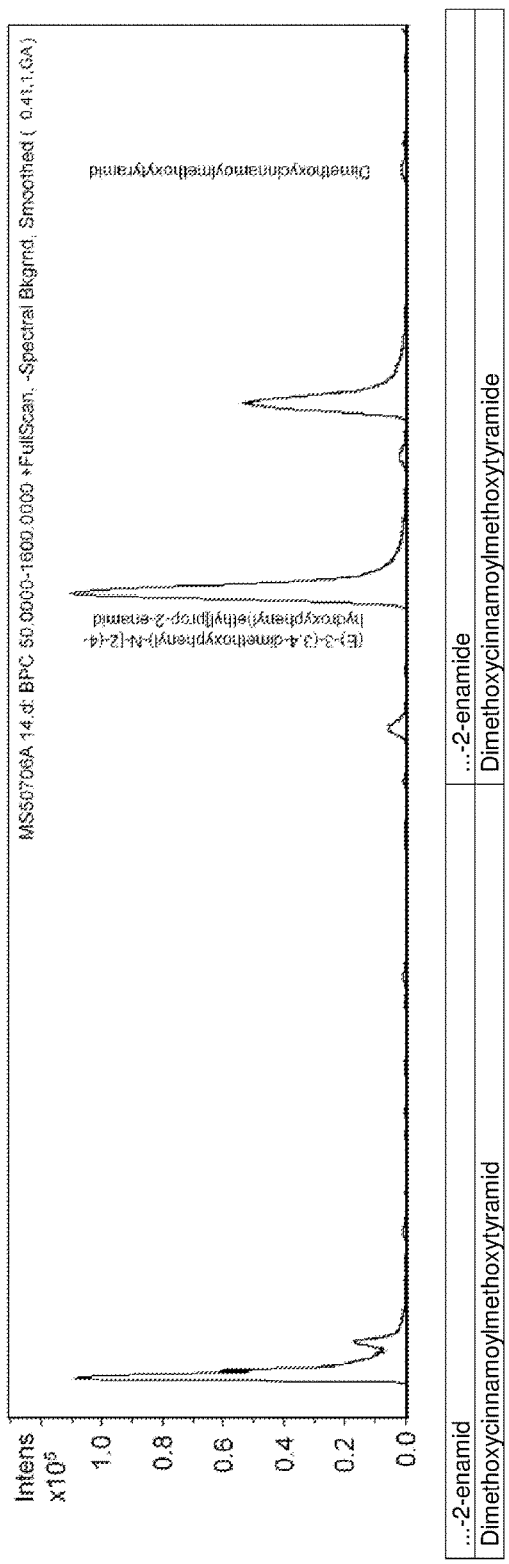
FIG. 13 shows an LC-MS chromatogram of an enzymatic conversion of (E)-3-(3,4-dimethoxyphenyl)-N-[2-(4-hydroxyphenyl)ethyl]prop-2-enamide to dimethoxycinnamoylmethoxytyramide.
Figure 14:
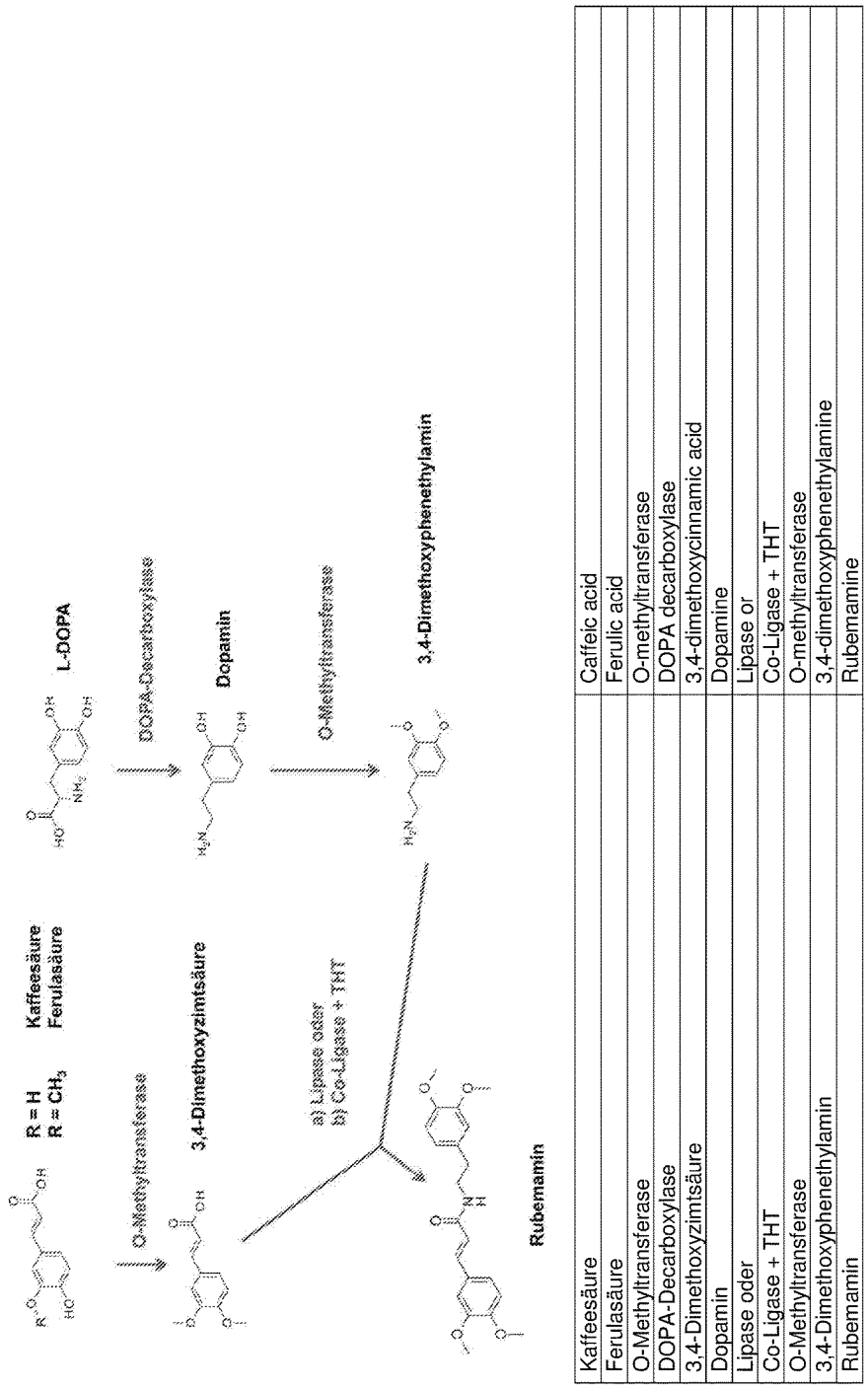
FIG. 14 shows a schematic diagram of a biosynthesis path for producing rubemamine starting with a cinnamic acid and L-DOPA. The cinnamic acid and the L-DOPA path first converge here in the last step prior to amide coupling by means of lipase or co-ligase (CL) and THT.
Figure 15:
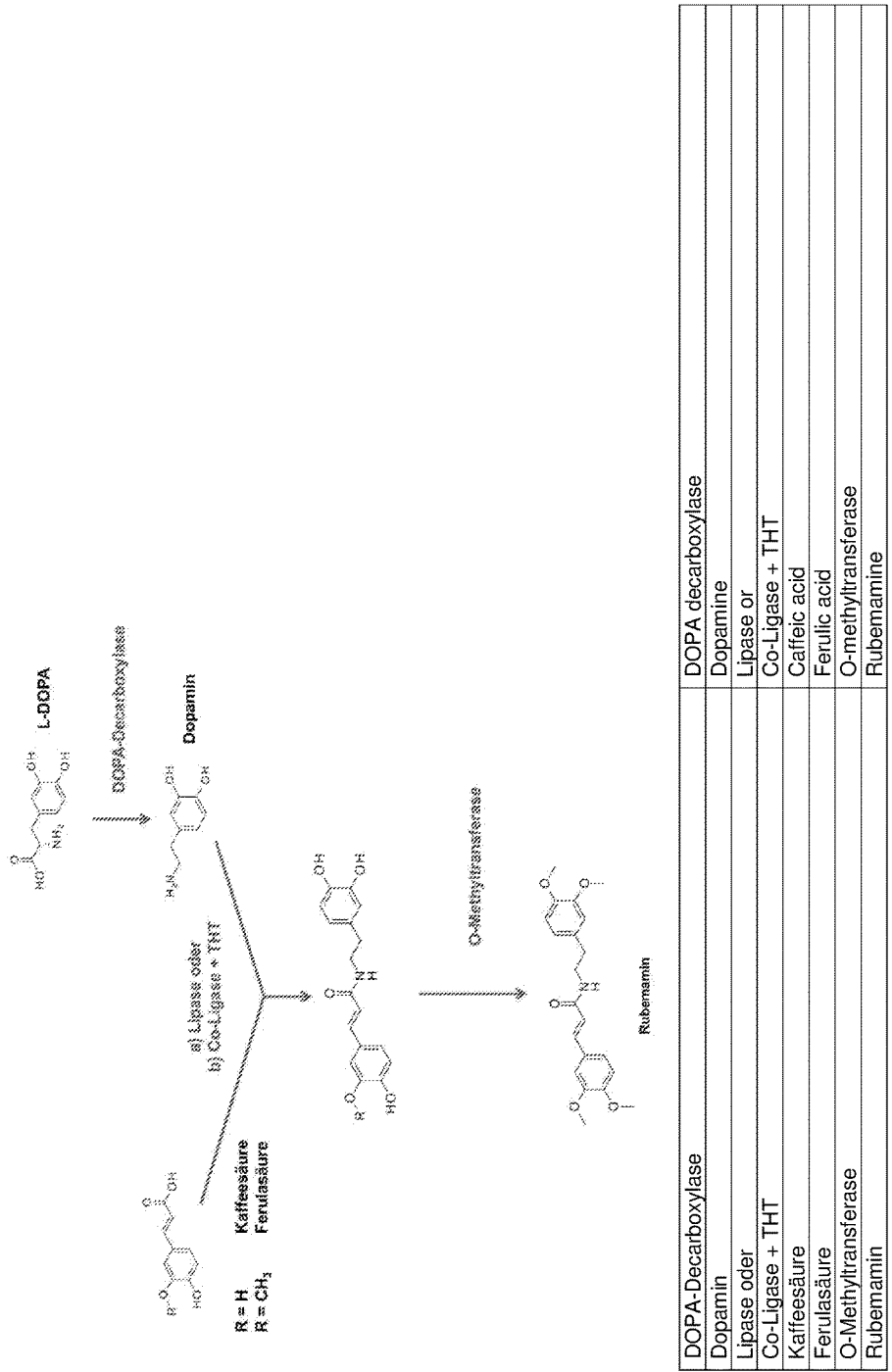
FIG. 15 shows a schematic diagram of a further synthesis path for producing rubemamine starting with a cinnamic acid and L-DOPA. Here the amide coupling and thus the combination of both starting paths in the cinnamic acid path takes place prior to activity of an OMT. Here the addition of a lipase or a co-lignase (CL) and THT takes place beforehand.
Figure 16:
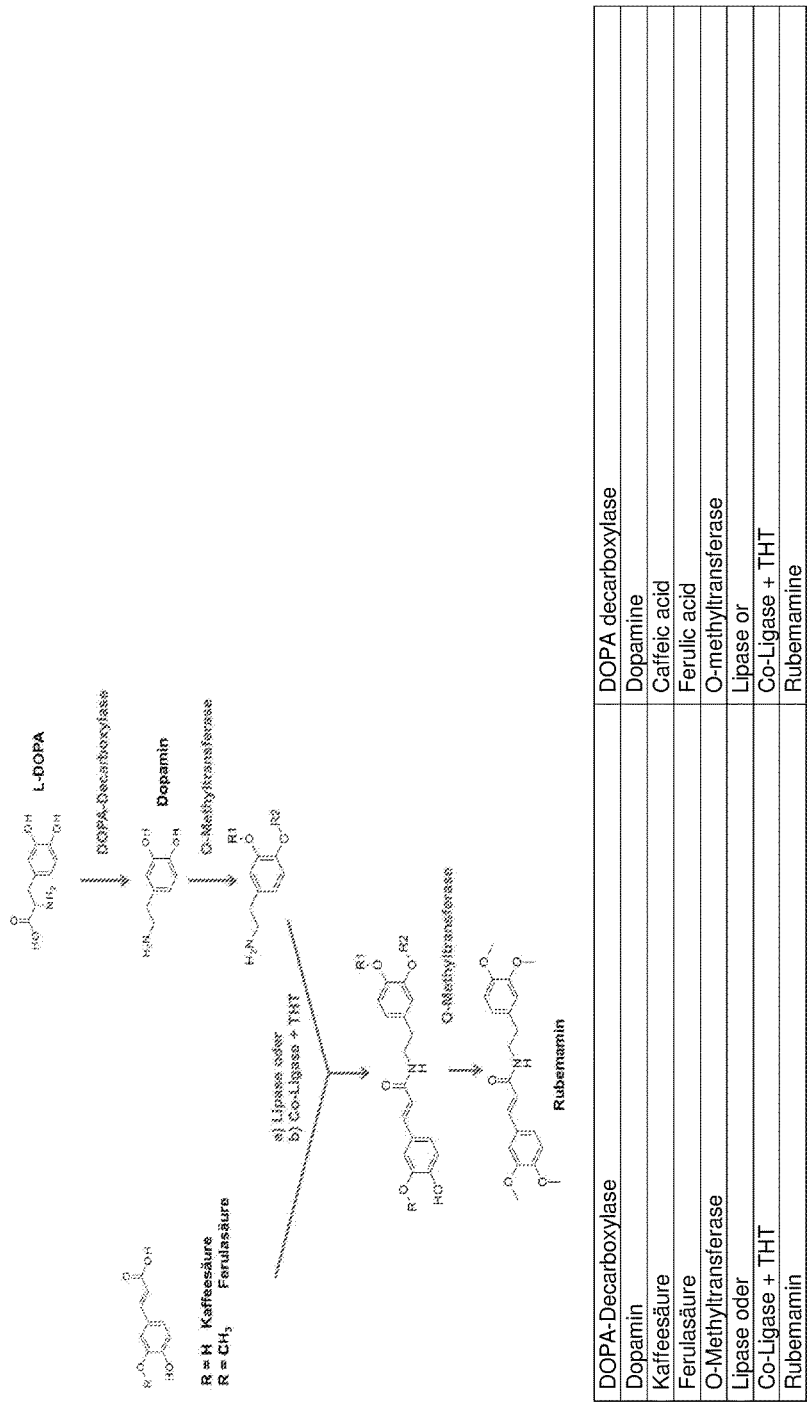
FIG. 16 shows a schematic diagram of a further synthesis path for producing rubemamine starting with a cinnamic acid and L-DOPA. Here the amide coupling and thus the combination of both starting paths takes place by adding a lipase or a co-ligase (CL) and THT prior to the methylization of the cinnamic acid components.
Figure 17:
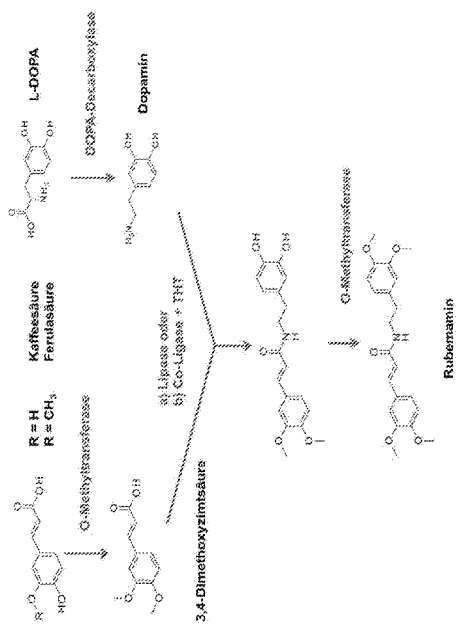
FIG. 17 shows a schematic diagram of a further synthesis path for producing rubemamine starting with a cinnamic acid and L-DOPA. Here the amide coupling and thus the combination of both starting paths takes place by adding a lipase or a co-ligase (CL) and THT after the methylization of the cinnamic acids but prior to the methylization of dopamine.

The disclosed cinnamic acids can be present either in the free form thereof or esterified on hemicelluloses such as occur as components of the plant cell wall.

The nucleic acids used according to the present invention for expressing a desired target protein can optionally be codon-optimized, that is, the codon use of a gene is adapted to the recombinant microorganism or fungus selected as the expression strain. It is known to the person skilled in the art that a desired target gene coding a protein of interest can be modified without changing the translated protein sequence in order to consider the specific species-dependent codon use. The nucleic acids of the present invention to be transformed can thus be specifically adapted to the codon use of *E. coli* or another bacterium, of *Saccharomyces* spp. or another yeast, or of *Trichoderma* spp. or another fungus.

The term offspring as used herein refers. in the context of a recombinant microorganism or fungus according to the present disclosure, to the descendants of such an organism arising from the original organism through natural reproductive processes comprising sexual and asexual processes. It is known to the person skilled in the art that in the course of reproduction by natural means, mutations can be introduced into the genome of an organism, whereby the offspring differs genomically from the parent organism, but can still be associated with the same (sub-)species. The term offspring according to the present disclosure thus also comprises such offspring modified by natural processes.

The term vector system as used herein refers to a system made of at least one or more vectors or plasmid vectors or comprising the same. A vector system can thus comprise a (plasmid) vector coding two different target genes. A vector system can also comprise a plurality of (plasmid) vectors, each in turn comprising at least one target gene according to the present disclosure. A vector system can thus comprise only one (plasmid) vector construct or a plurality of (plasmid) vector constructs, wherein the latter can be transformed stably or transiently at the same time or one after the other in the corresponding recombinant host organism, so that the target genes coded by the individual constructs can be transcribed and translated by the host organism.

The breeding and cultivation, isolation, and purification of a recombinant microorganism or fungus or a protein or enzyme coded by a nucleic acid according to the disclosure of the present invention are known to the person skilled in the art.

The terms protein, polypeptide, and enzyme are used interchangeably here due to the always enzymatic function of the gene products disclosed herein. The terms gene and nucleic acid (segment) are also used interchangeably for the purposes of the present disclosure.

Whenever the present disclosure refers to sequence homologies or sequence identities of nucleic or protein sequences in the form of percentages, these data refer to such values as can be calculated using EMBOSS Water Pairwise Sequence Alignments (Nucleotide) (http://www.ebi.ac.uk/Tools/psa/emboss_water/nucleotide.html) for nucleic acid sequences or EMBOSS Water Pairwise Sequence Alignments (Protein) (http://www.ebi.ac.uk/Tools/psa/emboss_water/) for amino acid sequences. Tools made available by the European Molecular Biology Laboratory (EMBL) European Bioinformatics Institute (EBI) for local sequence alignments use a modified Smith-Waterman algorithm (see http://www.ebi.ac.uk/Tools/psa/ and Smith, T. F. & Waterman, M. S. "Identification of common molecular subsequences" *Journal of Molecular Biology*, 1981 147 (1):195-197). Furthermore, when performing the pairwise alignment of two sequences using the modified Smith-Waterman algorithm, reference is hereby made to the default parameters currently provided by the EMBL-EBI. These are (i) for amino acid sequences: Matrix=BLOSUM62, Gap open penalty=10, and Gap extend penalty=0.5, and (ii) for nucleic acid sequences: Matrix=DNAfull, Gap open penalty=10 and Gap extend penalty=0.5.

Detailed Description

According to a first aspect of the present invention, starting with a hydroxycinnamic acid or a hydroxycinnamic acid esterified on a hemicellulose, a 3,4-methylized cinnamic acid or a 3,4-methylized cinnamic acid ester is obtained using a 4'-O-methyltransferase (4-OMT) and an S-adenosylmethionine-synthase (SAMS). Said conversion takes place by providing a recombinant microorganism or fungus comprising (a1) a nucleic acid segment comprising or made of at least one gene coding for a 4'-O-methyltransferase (4-OMT) and (a2) optionally a nucleic acid segment comprising or made of at least one gene coding for a 3'-O-Methyltransferase (3-OMT), and (b) optionally for fermentative production, a nucleic acid segment comprising or made of a gene coding for an S-adenosylmethionine synthase (SAMS), and by cultivating the recombinant microorganism or fungus under conditions allowing the expression of the nucleic acid segment(s) for obtaining the corresponding product(s) of expression; optionally isolating and optionally purifying the product(s) of expression obtained, and adding one or more hydroxycinnamic acid(s), preferably adding caffeic acid or ferulic acid, and/or one or more precursors or one or more derivatives thereof, particularly a precursor or a derivative of caffeic acid or ferulic acid esterified on a hemicellulose, to the cultivated recombinant microorganism or fungus in accordance with step (ii) for a fermentative conversion or to the product(s) of expression according to step (iii) for an enzymatic conversion; and by cultivating or incubating the recombinant microorganism or fungus or the product(s) of expression under conditions enabling the conversion of the hydroxycinnamic acid or the precursor(s) or the derivative or derivatives thereof to a 3,4-methylized cinnamic acid or a 3,4-methylized cinnamic acid ester, obtaining the corresponding 3,4-methylized cinnamic acid or 3,4-methylized cinnamic acid ester; and optionally by isolating and optionally purifying the obtained 3,4-methylized cinnamic acid or the 3,4-methylized cinnamic acid ester and further byproducts that are optionally present.

The hydroxycinnamic acid can be present in a free form or esterified. Esters of hydroxycinnamic acids are present in the plant cell wall.

Microorganisms and fungi suitable for production at an industrial scale of target proteins according to all considerations of the present invention as recombinant organisms are known to the person skilled in the art and preferably comprise, but are not limited to, *E. coli* spp., such as *E. coli* BL21, *E. coli* MG1655, *E. coli* W3110, and offspring thereof, *Bacillus* spp. such as *Bacillus licheniformis*, *Bacillus subitilis*, or *Bacillus amyloliquefaciens*, and offspring thereof, *Saccharomyces* spp., such as *S. Cerevesiae*, and offspring thereof, *Hansenula* and *Pichia* spp., such as *P. pastoris* and *H. polymorpha*, and offspring thereof, *Kluyveromyces* spp, such as *K. lactis*, and offspring thereof, *Aspergillus* spp., such as *A. oryzae*, *A. nidulans*, or *A. niger*, and offspring thereof, or *Trichoderma* spp., such as *T. reesei* or *T. harzianum*, and offspring thereof.

Methods for breeding and cultivating the recombinant microorganisms and fungi according to the present disclosure and allowing the expression of nucleic acid segments according to the present disclosure and the conversion of the reactants according to the present invention using the disclosed enzymes are known to the person skilled in the art.

4'-O-Methyltransferases (4-OMTs) for use according to all considerations of the present invention are those able, due to the substrate specificity and regional selectivity thereof, to catalyze the methylization of a 4'-O-group of a free or esterified hydroxycinnamic acid, or L-dihydroxyphenylalanine or a precursor or a derivative thereof, or coupling products of a free or esterified hydroxycinnamic acid or L-dihydroxyphenylalanine or a precursor or a derivative thereof. Preferred nucleic acids coding the 4-OMTs of the present invention comprise those selected from the group of SEQ ID NOs: 5, 6, 7, 8, 9, 15, 17, 18, and 85, and sequences having at least 80%, 81%, 82%, 83%, 84%, 85%, 86%, 87%, 88%, 89%, 90%, 91%, 92%, 93%, 94%, 95%, 96%, 97%, 98% or 99% sequence homology relative to said sequences. Preferred 4-OMT polypeptides coded by the nucleic acids according to the present invention comprise those selected from the group of SEQ ID NOs: 25, 26, 27, 28, 29, 35, 37, 38, and 86, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences and still fulfilling, despite modification, the same enzymatic function as the non-modified polypeptide having the corresponding SEQ ID NO. Said nucleic acid sequences can be codon-optimized or truncated, or can comprise targeted point mutations. A preferred point mutation is present at position 133 or 322 in relation to SEQ ID NO. 35. Preferred point mutations are L322N (see SEQ ID NOs: 8 and 28) or T133S (see SEQ ID NOs: 9 and 29) or a combination of both mutations (SEQ ID NOs:85 and 86 according to the corresponding nucleic acid or polypeptide sequence.)

3'-O-methyltransferases (3-OMTs) for use according to all considerations of the present invention are those able, due to the substrate specificity and regional selectivity thereof, to catalyze the methylization of a 3'-O-group of a free or esterified hydroxycinnamic acid, or L-dihydroxyphenylalanine or a precursor or a derivative thereof, or coupling products of a free or esterified hydroxycinnamic acid or L-dihydroxyphenylalanine or a precursor or a derivative thereof.

Preferred nucleic acids coding the 3-OMTs of the present invention comprise those selected from the group of SEQ ID NOs: 3, 4, 16, 19, and 20, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences. Preferred 3-OMT polypeptides coded by the nucleic acids according to the present invention comprise those selected from the group of SEQ ID NOs: 23, 24, 36, 39, and 40, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences, under the condition that a sequence having a corresponding degree of homology as the SEQ ID NOs listed still fulfills the same enzymatic function as the non-modified polypeptide having the corresponding SEQ ID NO. Said nucleic acid sequences can be codon-optimized or truncated, or can comprise targeted point mutations.

The use of a 3-OMT according to the method of the present invention is optional for such methods wherein the 3'-methylization is already present in the reactant.

S-adenosylmethionine synthases (SAMSs) for use according to all considerations of the present invention are those able, due to the substrate specificity and regional selectivity thereof, to catalyze the conversion of ATP and methionine to S-adenosylmethionine. Preferred nucleic acids coding the SAMSs of the present invention comprise those selected from the group of SEQ ID NOs: 10, 65, 67, 69, and 71, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences. Preferred SAMS polypeptides coded by the nucleic acids according to the present invention comprise those selected from the group of SEQ ID NOs: 30, 66, 68, 70, and 72, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences, under the condition that a sequence having a corresponding degree of homology as the SEQ ID NOs listed still fulfills the same enzymatic function as the non-modified polypeptide having the corresponding SEQ ID NO. Said nucleic acid sequences can be codon-optimized or truncated, or can comprise targeted point mutations.

The addition of a gene coding for an S-adenosylmethionine synthase (SAMS) leads to improved provision of S-adenosylmethionine in said consideration and in all further considerations of the present invention and can increase the yield of the corresponding process.

In one embodiment of said consideration and all further considerations of the present invention the conversion can be purely fermentative. According to said embodiment, the nucleic acid(s) of interest are expressed in a recombinant microorganism or fungus and the conversion of the products occurs in vivo in the recombinant microorganism or fungus.

In a further embodiment of said consideration and all further considerations of the present invention the final conversion of the reactants is enzymatic. The nucleic acid(s) of interest are thereby first expressed in a recombinant microorganism or fungus. The protein(s) thus obtained are then optionally purified and the resulting purified protein(s) are combined in vitro under reaction conditions ensuring the activity of the protein(s), for a period of time sufficient for obtaining maximum conversion, for converting a selected reactant according to any arbitrary consideration of the present invention, optionally using further substances or enzymes in a suitable buffer allowing the conversion of the products and optionally using further additives required for the conversion.

Suitable reaction conditions such as buffers, additives, temperature and pH conditions, and optionally further proteins can easily be determined by a person skilled in the art with knowledge of the biosynthesis path disclosed herein and the enzymes required therefor, said enzymes also determining the selection of the reaction conditions, according to any arbitrary consideration of the present disclosure.

In the second consideration of the present invention, starting with dopamine and/or L-dihydroxyphenylalanine (L-DOPA) or a precursor or a derivative thereof, 3,4-dimethoxyphenethylamine is obtained using a 4-OMT and a 3'-O-methyltransferase (3-OMT). Said conversion is performed by providing a recombinant microorganism or fungus comprising (a1) a nucleic acid segment comprising or made of at least one gene coding for a 4'-O-methyltransferase, and (a2) a nucleic acid segment comprising or made of at least one gene coding for a 3'-O-Methyltransferase, and (b) optionally a nucleic acid segment comprising or made of a gene coding for an S-adenosylmethionine synthase (SAMS), and (c) optionally a nucleic acid segment comprising or made of a gene coding for a DOPA-decarboxylase (DDC), and by cultivating the recombinant microorganism under conditions allowing the expression of the nucleic acid segments for obtaining the corresponding products of expression; and optionally by isolating and optionally purifying the products of expression obtained; adding dopamine and/or L-dihydroxyphenylalanine and/or one or more precursors or one or more derivatives thereof, particularly a precursor or a derivative thereof, to the cultivated recombinant microorganism according to step (ii) for a fermentative conversion or to the products of expression according to step (iii) for an enzymatic conversions, wherein for the case of enzymatic conversion S-adenosylmethionine is also preferably added; and by cultivating or incubating the recombinant microorganism or the products of expression under conditions enabling the conversion of dopamine or L-dihydroxyphenylalanine and/or the precursor(s) or the derivative or derivatives thereof to 3,4-dimethoxyphenethylamine for obtaining 3,4-dimethoxyphenethylamine; and optionally by isolating and optionally purifying the obtained 3,4-dimethoxypnenethylamine and further byproducts that are optionally present.

Preferred precursors or derivatives of dopamine are selected from L-dihydroxyphenylalanine (L-DOPA), tyrosine, or phenylalanine.

In one embodiment of said consideration the implementation can be purely fermentative. In a further embodiment, the final implementation of the reactants is enzymatic.

The steps of methylization by means of the 4-OMT and the 3-OMT can take place simultaneously or one after another in an arbitrary sequence.

In one embodiment, in addition to the 4-OMT and the 3-OMT, a nucleic acid segment coding a SAMS is also transcribed and translated by the recombinant microorganism or fungus.

In a further embodiment, starting with L-DOPA or a precursor or a derivative thereof, a nucleic acid segment coding a DDC is also transcribed and translated by the recombinant microorganism.

In the case of enzymatic conversion according to consideration two of the present invention, S-Adenosylmethionine is further preferably added to the preparation.

Preferred nucleic acids coding the DOPA-decarboxylases (DDCs) of the present invention comprise those selected from the group of SEQ ID NOs: 1 (DmDDC, codon-optimized), 2 (AmDDC, codon-optimized), 59, 61, and 63, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences. Preferred 3-OMT polypeptides coded by the nucleic acids according to the present invention comprise those selected from the group of SEQ ID NOs: 21, 22, 60, 62, and 64, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences, under the condition that a sequence having a corresponding degree of homology as the SEQ ID NOs listed still fulfills the same enzymatic function as the non-modified polypeptide having the corresponding SEQ ID NO. Said nucleic acid sequences can be codon-optimized or truncated, or can comprise targeted point mutations.

Just as for the first consideration of the present invention, here again it is essential that the specific function of a 4-OMT is linked in a targeted manner to a further enzyme, here a 3-OMT and optionally a SAMS and/or a DCC, whereby the biosynthesis path provided by the present invention can be performed for obtaining the target products.

In a third consideration of the present invention, starting with a hydroxycinnamic acid or a hydroxycinnamic acid esterified on a hemicellulose and with dopamine and/or L-dihydroxyphenylalanine or a precursor or a derivative thereof, a 4-methylized cinnamic acid amide is obtained using a 4-OMT, a SAMS, and a 3-OMT. This is done by providing a recombinant microorganism or fungus as defined for the first consideration of the present invention, additionally comprising: (d) a nucleic acid segment comprising or made of at least one gene coding for a 4-coumarat:CoA-ligase (CL), and (e) a nucleic acid segment comprising or made of at least one gene coding for a tyramine-N-hydroxycinnamoyltransferase (THT), and (f) optionally a nucleic acid segment comprising or made of at least one gene coding for a DOPA-decarboxylase (DDC), and by cultivating the recombinant microorganism or fungus under conditions allowing the expression of the nucleic acid segments for obtaining the corresponding products of expression; and optionally by isolating and optionally purifying the products of expression obtained; by adding dopamine and/or L-dihydroxyphenylalanine and a hydroxycinnamic acid, preferably caffeic acid or ferulic acid, to the cultivated recombinant microorganism or fungus according to step (ii) for a fermentative conversion, or a phenethylamine, particularly dopamine, 3-methoxytyramine, 3-hydroxy-4-methoxyphenethylamine, 3,4-dimethoxyphenethylamine, and a cinnamic acid ester, particularly esters of caffeic acid, ferulic acid, isoferulic acid, or 3,4-dimethoxycinnamic acid to the products of expression according to step (iii) for an enzymatic conversion, wherein for the case of enzymatic conversion S-adenosylmethionine is preferably also added; and by cultivating or incubating the recombinant microorganism or fungus or the products of expression, optionally adding a lipase under conditions enabling the conversion of dopamine and/or L-dihydroxyphenylalanine and of a hydroxycinnamic acid to a 4-methylized cinnamic acid amide; and optionally by isolating and optionally purifying the obtained 4-methylized cinnamic acid amide and further byproducts that are optionally present.

In one embodiment of said consideration the implementation can be entirely fermentative. In a further embodiment, the final implementation of the reactants is enzymatic.

In the case of enzymatic conversion according to consideration three of the present invention, coenzyme A and adenosine triphosphate (ATP) are further preferably added to the preparation.

Preferred nucleic acids coding the coumarat:CoA-ligases (CLs) of the present invention comprise those selected from the group of SEQ ID NOs: 11, 12, 73, 75, and 77, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences. Preferred CL polypeptides coded by the nucleic acids according to the present invention comprise those selected from the group of SEQ ID NOs: 31, 32, 74, 76, and 78, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences, under the condition that a sequence having a corresponding degree of homology as the SEQ ID Nos listed still fulfills the same enzymatic function as the non-modified polypeptide having the corresponding SEQ ID NO. Said nucleic acid sequences can be codon-optimized or truncated, or can comprise targeted point mutations.

Preferred nucleic acids coding the tyramine-N-hydroxycinnamoyltransferases (THTs) of the present invention comprise those selected from the group of SEQ ID NOs: 13, 14, 79, and 81, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences. Preferred THT polypeptides coded by the nucleic acids according to the present invention comprise those selected from the group of SEQ ID NOs: 33, 34, 80, and 82, and sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences, under the condition that a sequence having a corresponding degree of homology as the SEQ ID Nos listed still fulfills the same enzymatic function as the non-modified polypeptide having the corresponding SEQ ID NO. Said nucleic acid sequences can be codon-optimized or truncated, or can comprise targeted point mutations.

A further preferred embodiment according to any arbitrary consideration of the present invention also relates to the use of nucleic acid sequences coding for polypeptides and serving the purpose of cleaning, secreting, detecting, or localizing the decarboxylase and/or the 3'-O-methyltransferase and/or the 4'-O-methyltransferase and/or the S-adenosylmethionine synthase and/or the 4-coumarat:CoA-ligase and/or the tyramine-N-hydroxycinnamoyltransferase. Said nucleic acid segments are also referred to as tag sequences and can precede (N-terminal) and/or succeed (C-terminal) the nucleic acid segments coding for decarboxylase and/or 3'-O-methyltransferase and/or 4'-O-methyltransferase and/or S-adenosylmethionine synthase and/or 4-coumarat:CoA-ligase and/or tyramine-N-hydroxycinnamoyltransferase. Tag sequences selected from the following list are particularly preferred: polyhistidine (His) tag, glutathione-S-transferase (GST) tag, thioredoxine tag, FLAG tag, green fluorescent protein (GFP) tag, streptavidin tag, maltose bindeprotein (MBP) tag, chloroplastentransitpeptide, mitochondrientransitpeptide, and/or a secretion tag.

In a preferred embodiment of the present invention, the lipase used is a lipase B. The lipase can be immobilized. In a more preferred embodiment, the lipase is a lipase B from *Candida antarctica*. A nucleic acid or polypeptide sequence of a lipase B from *Candida antarctica* is shown in SEQ ID NOs: 83 and 84. In a further embodiment, sequences having at least 80%, 81%, 82%, 83%, 84%, 85%, 86%, 87%, 88%, 89%, 90%, 91%, 92%, 93%, 94%, 95%, 96%, 97%, 98%, or 99% sequence homology relative to said sequences are included in the present disclosure, under the condition that a sequence having a corresponding degree of homology as the SEQ ID NOs listed still fulfills the same enzymatic function as the non-modified polypeptide having the SEQ ID NO.: 84. In one embodiment, the lipase B from *Candida antarctica* can be present in immobilized form. Suitable lipases for use according to the present invention are commercially available (for example from Roche, Mannheim).

In one embodiment of said consideration, the amide coupling for fermentative implementation can take place using a 4-coumarat:CoA-ligase (CL) and a tyramine-N-hydroxycinnamoyltransferase (THT). In a further embodiment the amide coupling takes place for enzymatic implementation by means of a lipase. The enzymatic step of the amide coupling can thereby be catalyzed by a lipase.

In a further embodiment of said aspect, the amide coupling takes place in an arbitrary sequence relative to the reaction steps of the 4'-O-methylization and the optional 3'-methylization.

In one embodiment, the 4-methylized cinnamic acid amide according to consideration three is selected from the group of rubemamine [(2E)-3-(3,4-dimethoxyphenyl)-N-[2-(3,4-dimethoxyphenyl)ethyl]prop-2-enamide], feruloyl-3-methoxytyramide [(2E)-3-(4-hydroxy-3-methoxyyphenyl)-N-[2-(4-hydroxy-3-methoxyphenyl)ethyl]prop-2-enamide], (2E)-3-(3,4-dimethoxyphenyl)-N-[2-(4-hydroxy-3-methoxy-phenyl)ethyl]prop-2-enamide], and 3,4-dimethoxycinnamoylmethoxytyramide [(2E)-3-(3,4-dimethoxyphenyl)-N-[2-(4-methoxyphenyl)ethyl]prop-2-enamide].

Said third consideration of the present invention combines two metabolic paths while continuing the first and the second consideration. While intermediate products are provided by novel biotechnological methods in the first and second consideration, the combination and extension of both paths according to the method from consideration three leads to further, more complex synthesis products. For all three considerations of the present invention, this is achieved in a biotechnological manner using targeted linking of metabolic paths and using a recombinant microorganism or fungus and a 4-OMT.

The present invention further relates to vector systems comprising or made of the nucleic acid segments or vectors according to one of the considerations of the present invention.

In one embodiment a vector system, particularly a plasmid vector system is disclosed, comprising or made of one or more vectors or plasmid vectors comprising (a1) a nucleic acid segment comprising or made of at least one gene coding for a 4'-O-methyltransferase, and (a2) optionally a nucleic acid segment comprising or made of at least one gene coding for a 3'-O-methyltransferase, and (b) optionally a nucleic acid segment comprising or made of a gene coding for an S-adenosylmethionine synthase, wherein the nucleic acid segments are provided on the same vector or two or more separate vectors in the presence of a nucleic acid segment (a2) and/or a nucleic acid segment (b).

In a different embodiment a vector system, particularly a plasmid vector system, comprising one or more vectors or plasmid vectors, is disclosed, comprising (a1) a nucleic acid segment comprising or made of at least one gene coding for a 4'-O-methyltransferase, and (a2) a nucleic acid segment comprising or made of at least one gene coding for a 3'-O-methyltransferase, and (b) optionally a nucleic acid segment comprising or made of a gene coding for an S-adenosylmethionine synthase, and (c) optionally a nucleic acid segment comprising or made of a gene coding for a DOPA-decarboxylase, wherein the nucleic acid segments are provided on the same vector or two or more separate vectors.

In yet another embodiment a vector system, particularly a plasmid vector system, is disclosed, comprising (a1) a nucleic acid segment comprising or made of at least one gene coding for a 4'-O-methyltransferase, and (a2) optionally a nucleic acid segment comprising or made of at least one gene coding for a 3'-O-methyltransferase, and (b) optionally a nucleic acid segment comprising or made of at least one gene coding for an S-adenosylmethionine synthase and additionally comprising one or more vectors or plasmid vectors comprising (d) a nucleic acid segment comprising or made of at least one gene coding for a 4-coumarat:CoA-ligase, and (e) a nucleic acid segment comprising or made of at least one gene coding for a tyramine-N-hydroxycinnamoyltransferase, and (f) optionally a nucleic acid segment comprising or made of at least one gene coding for DOPA-Decarboxylase, wherein the nucleic acid segments are provided on the same vector or two or more separate vectors.

Further disclosed are recombinant microorganisms and fungi bearing the vectors necessary for performing the method according to the invention or a vector system and thus coding the nucleic acids for performing the methods according to the invention according to one of the described considerations.

In one embodiment the recombinant microorganism or fungus comprises a vector system, particularly a plasmid vector system, as described herein.

Preferred recombinant microorganisms or fungi are selected from the group of *Eschericia coli* spp., preferably *E. coli* BL21, *E. coli* MG165, or *E. coli* W3110, and offspring thereof, *Bacillus* spp., preferably *Bacillus licheniformis, Bacillus subitilis*, or *Bacillus amyloliquefaciens*, and offspring thereof, *Saccharomyces* spp., preferably *S. cerevesiae*, and offspring thereof, *Hansenula* or *Pichia* spp., preferably *P. pastoris* and *H. polymorpha*, and offspring thereof, *Kluyveromyces* spp, preferably *K. lactis*, and offspring thereof, *Aspergillus* spp., preferably *A. oryzae, A. nidulans*, or *A. niger*, and offspring thereof, or *Trichoderma* spp., preferably *T. reesei* or *T. harzianum*, and offspring thereof.

The present invention further relates to nucleic acid segments and polypeptides mutated and optionally codon-optimized for use for performing the method according to the present invention. Said nucleic acid segments are selected from, but not limited to, the group of SEQ ID NOs: 8, 16, 17, 20, and 85. The polypeptides bearing a mutation are selected from, but not limited to, the group of SEQ ID NOs: 28, 36, 37, 40, and 86.

Further, a composition comprising the products of the method according to the invention according to aspect three are provided.

In one embodiment the composition comprises rubemamine and at least one further substance selected from the group of 3,4-dimethoxycinnamic acid, ferulic acid, caffeic acid, 3-methoxytyramine, 3-hydroxy-4-methoxyphenethylamine, L-DOPA, 3,4-dimethoxyphenethylamine.

In a further embodiment, the composition comprises 50-99 wt-% rubemamine, 0.1-49.9 wt-% 3,4-dimethoxycinnamic acid, and 0.1-49.9 wt-% 3,4-dimethoxyphenethylamine.

EXAMPLES

The present invention is further explained by means of the following examples, not to be seen as limiting.

Example 1: Producing Various Individual Constructs

For producing the individual constructs used, that is, a vector having a coding sequence and suitable for protein expression, the coding sequence for each of various target genes was synthesized and cloned between two restriction interfaces into the vector pET28a (Merck Chemicals GmbH, Schwalbach) or pQE30 (Qiagen, Hilden) or pCDFDuet-1 (Merck Chemicals GmbH, Schwalbach). An overview of the cloned genes and the restriction interfaces used for each cloning is summarized in Table 1. For SEQ ID Nos: 7-9, 15, 17, 5, and 18 corresponding to CbMOMT and variants L322N and T133S thereof, CbIEMT1, RcOMT, GmSOMT, and PsOMT, the codon usage of the gene on *E. coli* was adapted as one of the planned expression hosts. In addition, in SEQ ID Nos 8, 9, 16, and 17, one or more point mutation(s) bear relative to the original sequence obtained from the corresponding organism.

TABLE 1

Overview of cloned genes with vector and restriction interfaces used

| Gene | SEQ ID NO (nucleic acid/protein) | Vector used | Restriction interface used |
|---|---|---|---|
| CbIEMT1 | 15/35 | pET28a | BamHI, XhoI |
| CbMOMT (also called MOMT4 or CbMOMT4) | 7/27 | pET28a | BamHI, XhoI |
| CrOMT | 16/36 | pET28a | BamHI, XhoI |
| GmSOMT | 5/25 | pET28a | NdeI, BamHI |
| McPFOMT | 4/24 | pET28a | BamHI, HindIII |
| MxSafC | 6/26 | pET28a | BamHI, HindIII |
| RcOMT | 17/37 | pET28a | BamHI, HindIII |
| AtCOMT | 3/23 | pQE30 | BamHI, HindIII |
| PsOMT | 18/38 | pQE30 | BamHI, KpnI |
| SynOMT | 19/39 | pQE30 | BamHI, HindIII |
| TaOMT2 | 20/40 | pQE30 | SacI, KpnI |
| ScSAMS2 | 10/30 | pCDFDuet-1 | PstI, HindII |

For producing the construct pGJ3610_DmDDC, the coding sequence of the target genes (SEQ ID NO: 1, SEQ ID NO: 2) was synthesized as a GeneArt© gene synthesis under contract at Life Technologies GmbH (Darmstadt) for later use in *E. coli* in a codon-optimized variant. The coding sequence of the genes was then cut out of the gene synthesis plasmid according to a conventional practice known to the person skilled in the art by means of restriction digest using the restriction endonucleases BamHI and NcoI (New England BioLabs GmbH, Frankfurt). The restriction preparation was then separated on an agarose gel and the target fragment was elucted from the from gel at a length of 1430 base pairs by means of the NucleoSpin® Gel and PCR Clean-up-Kit (Macherey-Nagel GmbH & Co. KG, Düren). The base expression plasmid was digested using the restriction endonucleases BamHI and NcoI (New England BioLabs GmbH, Frankfurt) for producing the target expression plasmid and the DNA fragment obtained at a length of 2981 base pairs was elucted from an agarose gel by means of the NucleoSpin® Gel and PCR Clean-up-Kit (Macherey-Nagel GmbH & Co. KG, Düren) after electrophoretic separation. The production of the expression plasmid took place by means of a ligation reaction using 50 ng each of the purified DNA fragments (target fragment and expression plasmid fragment) and T4 DNA ligase (New England BioLabs GmbH, Frankfurt) according to conventional practice known to the person skilled in the art. The reaction products were introduced into competent *E. coli* XL1-blue cells by means of standard transformation methods (Maniatis et al. 1983) and the cells were drawn on selective solid medium (LB+ ampicillin (100 mg/L)+6 g/L agar) for 18 h at 37° C. Fluid medium (3 ml; LB+ampicillin (100 mg/L) was inoculated with resistant individual colonies for identifying positive clones and drawn as before. The plasmid DNA of the cells was then analyzed via restriction typing by means of the GeneJET Plasmid Miniprep Kit (Thermo Scientific) according to conventional practice known to the person skilled in the art. Verification of the cloned DNA sequences of positive clones was performed by GATC Biotech (Konstanz, Germany).

Example 2: Producing Different CbMOMT Variants by Means of Mutagenesis

Starting with the plasmid pET28a_CbMOMT, various enzyme variants were produced using the QuikChange II Site-Directed Mutagenese Kit (Agilent, Waldbronn). TarTargeted mutations were thereby introduced into the coded sequence of CbMOMT in accordance with the manufacturers instructions using specific primers. For variant 1 of CbMOMT the primers MOMT-L322N_for (SEQ ID NO:41) and MOMT-L322N_rev (SEQ ID NO:42) were used, for variant 2 the primers MOMT-T133S_for (SEQ ID NO:43) and MOMT-T133S_rev (SEQ ID NO:44). The sequences according to SEQ ID NO: 8 and 9 are thereby produced. The sequences of the corresponding translated proteins are given in SEQ ID NO: 28 and 29.

Example 3: Producing Double Constructs in Use 3.1 Producing the Plasmid pET28a_CbMOMT_ScSAMS
  (a) Producing the Construct pET28a_GG
    The plasmid pET28a_CbMOMT_ScSAMS is produced by means of Golden Gate Technologie (WO2011/154147 A1). In preparation therefor the specific nucleic acid sequence (SEQ ID NO:53) is first synthesized and then cut using the restriction enzymes BamHI and HindIII and introduced into the vector pET28a (Merck Chemicals GmbH, Schwalbach) in a ligation preparation known to the person skilled in the art, whereby the plasmid pET28a_GG is obtained.
  (b) Amplifying the CbMOMT Gene
    The gene CbMOMT was amplified from plasmid DNA of the construct pET28a_CbMOMT (see Example 1) by means of the polymerase chain reaction (PCR) using the DreamTaq-DNA-Polymerase (Thermo Fisher Scientific, Bonn) according to prevalent practice known to the person skilled in the art. The primers M_term-F (SEQ ID NO:49) and M_term-R (SEQ ID NO:49) were used thereby. The PCR preparation was then separated on a 1% agarose gel and the target fragment was eluted out of the gel at a length of 1280 base pairs by means of the QIAprep Spin Miniprep Kit (Qiagen, Hilden).
  (c) Amplifying the ScSAMS Gene
    The gene ScSAMS was amplified from plasmid DNA of the construct pCDFDuet-1_ScSAMS (see Example 1) by means of the polymerase chain reaction (PCR) using the DreamTaq-DNA-Polymerase (Thermo Fisher Scientific, Bonn) according to prevalent practice known to the person skilled in the art. The primers S_prom-F (SEQ ID NO:51) and S_prom-R (SEQ ID NO:52) were used thereby. The PCR preparation was then separated on a 1% agarose gel and the target fragment was eluted out of the gel at a length of 1425 base pairs by means of the QIAprep Spin Miniprep Kit (Qiagen, Hilden).
  (d) Cloning the Genes CbMOMT and ScSAMS in pET28a_GG
    100 ng of the plasmid pET28a_GG (see Step 3.1 a) were incubated at 37° C. for 1 h with 24 ng of the cleaned CbMOMT fragment and 25 ng of the cleaned ScSAMS fragment in a 15 µL reaction preparation with 1×NEB T4 ligase buffer (New England Biolabs, Frankfurt am Main), 0.1 mg/mL BSA (New England Biolabs, Frankfurt am Main), 20 U BsaI (New England Biolabs, Frankfurt am Main), and 100 U NEB T4 DNA ligase (New England Biolabs, Frankfurt am Main), then incubated for 5 min at 50° C. and for 5 min at 80° C. to stop the reaction.
3.2 Producing the Plasmid pET28a_McPFOMT_CbMOMT-T133S
  a) Amplifying the Fragment T7-Promotor_McPFOMT_T7-Terminator
    A nucleic acid sequence comprising the T7 promotor, the coding sequence of McPFOMT, and the T7 terminator, including detecting sequences for the restriction enzymes SphI and BglII was amplified according to prevalent practice known to the person skilled in the art using the OneTaq-Polymerase (New England Biolabs, Frankfurt am Main) in a polymerase chain reaction (PCR) from plasmid DNA of the construct pET28a_McPFOMT (see Example 1) (Primer: SEQ ID NO:54, SEQ ID NO:55). The PCR preparation was then separated on a 1% agarose gel and the target fragment was eluted out of the gel at a length of 1079 base pairs by means of the QIAprep Spin Miniprep Kit (Qiagen, Hilden).
  b) Cloning the Fragment T7-Promotor_McPFOMT_T7-Terminator into the Vector pET28a_CbMOMT
    1 µg of the DNA fragment from a) and 3 µg of the vector pET28a_CbMOMT4 (see Example 1) were cut using the restriction enzymes SphI and BglII (New England Biolabs, Frankfurt am Main) according to prevalent practice known to the person skilled in the art and then separated on a 1% agarose gel. The corresponding fragments were eluted from the gel and cleaned by means of the QIAprep Spin Miniprep Kit (Qiagen, Hilden). Then 51.5 ng of the cleaned T7-Promotor_McPFOMT_T7-Terminator fragment were mixed with 100 ng of the cleaned pET28a_CbMOMT4 vector together with 5 U ExpressLink T4 DNA ligase (Life Technologies GmbH, Darmstadt), in a 20 µL reaction preparation with 1× ExpressLink ligase buffer (Life Technologies GmbH, Darmstadt) and incubated for 5 min at room temperature.
3.3 Producing the Construct pCDFDuet_At4CL2_CaTHT
  Each of the coding sequences of the target genes (At4CL2: SEQ ID NO:11, codon-optimized for *T. reesei*; CaTHT: SEQ ID NO:14) were synthesized and then cloned between the restriction interfaces PstI and NotI (At4CL2) and KpnI and XhoI (CaTHT) into the vector pCDFDuet (Merck Chemicals GmbH, Schwalbach). For both genes the codon usage was thereby adapted to *E. coli* as a potential expression host. The corresponding translated sequences are given as SEQ ID NOs: 31 and 34.
3.4 Producing the Construct pCDFDuet_NtCL1_NtTHT
  Each of the coding sequences of the target genes (Nt4CL1: SEQ ID NO:12, codon-optimized for *A. niger*; NtTHT: SEQ ID NO:13) were synthesized and then cloned between the restriction interfaces PstI and NotI (NtCL1) and PacI and AvrII (NtTHT) into the vector pCDFDuet (Merck Chemicals GmbH, Schwalbach). For both genes the codon usage was thereby adapted to *E. coli* as a potential expression host. The corresponding translated sequences are given as SEQ ID NOs: 32 and 33.

Example 4: Producing Triple Constructs in Use

One operon made of the T7-Promotor, 3 variable ribosome bonding points (RBS1-3), 3 coding nucleotide sequences (ORF1-3), and one T7 terminator was synthesized for producing each the triple constructs in use and then cloned into the vector pMA7 (see Table 2).

TABLE 2

Overview of the constructs pMA7-1 and pMA7-2 with the RBS used for ORF1-3 (the corresponding SEQ ID NOs 56, 57, and 58 are listed in each case.)

| Construct | RBS for ORF1 | RBS for ORF2 | RBS for ORF3 | ORF1 | ORF2 | ORF3 |
|---|---|---|---|---|---|---|
| pMA7-1 | 58 | 57 | 56 | 1 | 9 | 4 |
| pMA7-2 | 58 | 58 | 58 | 1 | 4 | 10 |

Example 5: Transformation of Plasmid DNA in *Escherichia coli* Cells

A transformation of the plasmid DNA in chemically competent *E. coli* NEB5a cells (New England Biolabs, Frankfurt am Main) took place for reproducing the plasmids produced in Example 1-4. Cells aliquoted to 50 µL were incubated on ice for 5 minutes. After adding 1 µL of plasmid DNA, the suspension was mixed and incubated on ice for an additional 30 minutes. The transformation took place in that the suspension was transferred to a thermoblock for 30 s at 42° C. and then to wet ice for 2 min. Then 600 µL of Luria broth (LB) medium (Carl Roth GmbH, Karlsruhe) were added and the cells were cultivated for 1 h at 37° C. and 180 rpm. Finally 200 µL of the culture were spread onto LB agar (Carl Roth GmbH, Karlsruhe) with the associated antibiotic. The Petri dish was incubated for 16 h at 37° C.

The transformation of the corresponding plasmid DNA took place in *E. coli* BL21(DE) cells for preparing for protein expression. Chemically competent cells aliquoted to 50 µL were incubated on ice for 5 minutes. After adding 1 µL of plasmid DNA, the suspension was mixed and incubated on ice for an additional 5 minutes. The transformation took place in that the suspension was transferred to a thermoblock for 30 s at 42° C. and then to wet ice for 2 min. Then 250 µL of LB medium (Carl Roth GmbH, Karlsruhe) were added and the cells were cultivated for 1 h at 37° C. and 180 rpm. Finally 200 µL of the culture were spread onto LB agar (Carl Roth GmbH, Karlsruhe) with the associated antibiotic. The Petri dish was incubated for 16 h at 37° C.

Example 6: Protein Expression and Cleaning

In preparation for protein expression at a volume of 50 mL, a preculture of 5 mL LB medium (Carl Roth GmbH, Karlsruhe) was first treated with the corresponding antibiotic and cells of each strain were taken from the agar plate and transferred into the preculture by means of an inoculating loop The preculture was then incubated for 16 h at 37° C. and 150 rpm. The main culture was taken from the preculture and inoculated with 50 mL LB medium (Carl Roth GmbH, Karlsruhe) and the corresponding antibiotic, so that the optical density at 600 nm as 0.1. The main culture was then incubated at 37° C. and 150 rpm until an optical density of 0.4-0.8 at 600 nm was reached. At this time 1 mM of isopropyl-β-D-thiogalactopyranoside was added for inducing the protein expression and the culture was incubated at 22° C. for an additional 16 h. The main culture was then centrifuged at 10,000 rpm for 10 min in order to obtain the cell pellet and then to be able to perform the protein extraction and cleaning. To this end, the cell disruption was first performed using the B-PER protein extraction reagent (Thermo Fisher Scientific, Bonn) according to the manufacturers instructions. The cell lysate thus obtained was then either used directly or processed by means of a 1 mL HisPur Ni-NTA chromatography column (Thermo Fisher Scientific, Bonn) according to the manufacturers instructions.

Example 7: Biotechnological Production of 3,4-Dimethoxycinnamic Acid 7.1 Enzymatic Presentation of 3,4-Dimethoxycinnamic Acid 2 mM ferulic acid were dissolved in 50 mM Tris buffer, pH 7.5, and incubated together with 4 mM S-adenosylmethionine and 50 µg CbMOMT, CbMOMT-L322N, CbMOMT-T133S, CbMOMT-T133S/L322N (SEQ ID NO:86) or GmSOMT protein at a total volume of 350 µL for 6 h at 30° C. The reaction was then terminated by adding 350 µL acetonitrile. The reaction mixture obtained was then analyzed using HPLC. A Poroshell 120 SB-C 18 (2.7 µm) separation column with a diameter of 2.1 mm and length of 100 mm was used for the analysis. The separation took place at a column temperature of 40° C. by means of the gradient method shown below. The mobile phase was water with 0.1% formic acid (A) and acetonitrile (B) at a flow rate of 0.4 ml/min. Detection took place at a wavelength of 320 nm. Retention times were determined and quantitative determination took place according to the external standard method using the corresponding reference substances.

Gradient method according to Example 7.1:

| | | |
|---|---|---|
| 0.00 min | A: 95% | B: 5% |
| 0.10 min | A: 95% | B: 5% |
| 10.00 min | A: 50% | B: 50% |
| 12.00 min | A: 0% | B: 100% |
| 15.00 min | A: 0% | B: 100% |
| 15.01 min | A: 95% | B: 5% |

7.2 Fermentative Presentation of 3,4-Dimethoxycinnamic Acid

*E. coli* BL21 (DE3) cells transformed by means of pET28a_CbMOMT-L322N and pET28a_CbMOMT-L322N_ScSAMS were cultivated in TB medium (23.6 g/L yeast extract, 11.8 g/L trypton, 9.4 g/L $K_2HPO_4$, 2.2 g/L $KH_2PO_4$, 4 mL/L glycerin) to an optical density of 0.6 at 600 nm and protein production was induced by adding 0.2 mM isopropyl-β-D-thiogalactopyranoside. Immediately after adding the inductor, the cultures were diluted with 5 mM ferulic acid and incubated at 30° C. for 48 h at 130 rpm. The reaction mixture obtained was then analyzed using HPLC as described in Example 7.1.

Example 8: Biotechnological Production of 3,4-Dimethoxyphenethylamine 8.1 Enzymatic Presentation of 3,4-Dimethoxyphenethylamine Starting with L-DOPA 1 mM L-DOPA were mixed together with 50 µg McPFOMT, 50 µg CbMOMT, 50 µg DmDDC (SEQ ID NO:1, codon-optimized sequence), 140 µM magnesium chloride, 40 µM pyridoxal phosphate, and 4 mM S-adenosylmethionine in 100 mM potassium phosphate buffer, pH 7.5, and incubated for 24 h at 30° C. The reaction mixture obtained was then analyzed using HPLC. A Grom Sil ODS-4 HE (5 µm) separation column with a diameter of 4 mm and length of 250 mm was used for the analysis. The separation took place at a column temperature of 40° C. by means of the gradient method shown below. The mobile phase was 20 mM potassium phosphate buffer pH 4.0 (A) and acetonitrile (B) at a flow rate of 0.8 ml/min. Detection took place at a wavelength of 214 nm. Retention times were determined and quantitative determination took place according to the external standard method using the corresponding reference substances.

Gradient method according to Example 8.1:

| 0.00 min | A: 100% | B: 0% |
| 15.00 min | A: 80% | B: 20% |
| 16.00 min | A: 100% | B: 0% |
| 21.00 min | A: 100% | B: 0% |

8.2 Fermentative Presentation of 3,4-Dimethoxyphenethylamine Starting with L-DOPA E. coli BL21 (DE3) cells transformed by means of pSYM_DDC and pET28a_McPFOMT_CbMOMT-T133S were separately cultivated in TB medium (23.6 g/L yeast extract, 11.8 g/L trypton, 9.4 g/L $K_2HPO_4$, 2.2 g/L $KH_2PO_4$, 4 mL/L glycerin) to an optical density of 0.6 at 600 nm and then mixed so that both cultures had an optical density of 0.5 at 600 nm. Then 1 mM isopropyl-β-D-thiogalactopyranoside and 0.1% arabinose were added for inducing protein expression and 5 mM L-DOPA were added as a substrate. After incubating the cultures at 30° C. and 170 rpm for 48 h, the fermentation supernatant was analyzed by means of HPLC as described in Example 8.1.

8.3 Enzymatic Presentation of 3,4-Dimethoxyphenethylamine Starting with Dopamine 1.3 mM dopamine were mixed together with 50 µg McPFOMT, 50 µg CbMOMT, 50 µg DmDDC (SEQ ID NO:1, codon-optimized sequence), 140 µM magnesium chloride, 40 µM pyridoxal phosphate, and 5.2 mM S-adenosylmethionine in 100 mM potassium phosphate buffer, pH 7.5, and incubated for 24 h at 30° C. The reaction mixture obtained was then analyzed using HPLC as described in Example 8.1.

8.4 Fermentative Presentation of 3,4-Dimethoxyphenethylamine Starting with Dopamine E. coli BL21 (DE3) cells transformed by means of pET28a_McPFOMT_CbMOMT-T133S were cultivated in TB medium (23.6 g/L yeast extract, 11.8 g/L trypton, 9.4 g/L $K_2HPO_4$, 2.2 g/L $KH_2PO_4$, 4 mL/L glycerin) to an optical density of 1.1 at 600 nm. Then 0.2 mM isopropyl-β-D-thiogalactopyranoside were added for inducing protein expression and 5 mM dopamine were added as a substrate. After incubating the cultures at 30° C. and 150 rpm for 48 h, the fermentation supernatant was analyzed by means of HPLC as described in Example 8.1.

Example 9: Biotechnological Production of Rubemamine

E. coli BL21 (DE3) cells transformed by means of pCDFDuet_At4CL2_CaTHT, pMA7-1, and pET28a_CbMOMT-L322N_ScSAMS were separately cultivated in TB medium (23.6 g/L yeast extract, 11.8 g/L trypton, 9.4 g/L $K_2HPO_4$, 2.2 g/L $KH_2PO_4$, 4 mL/L glycerin) to an optical density of 1.3 at 600 nm and then mixed so that all cultures had an optical density of 0.5 at 600 nm. Then 0.8 mM isopropyl-β-D-thiogalactopyranoside were added for inducing protein expression and 5 mM L-DOPA and 5 mM ferulic acid were added as a substrate. After incubating the cultures at 30° C. and 150 rpm for 48 h, the fermentation supernatant was analyzed by means of LC-MS. Waters Acquity UPLC was used with a Bruker micrOTOF Q-II detector for the analysis. The sample was separated by means of a Phenomenex Kinetex C18 (1.7 µm) separation column with a diameter of 2.1 mm and a length of 100 mm at a column temperature of 50° C. by means of the gradient method shown below. The mobile phase was water with 0.1% formic acid (A) and acetonitrile with 0.09% formic acid (B) at a flow rate of 0.3 ml/min. Retention times were determined and quantitative determination took place according to the external standard method using the corresponding reference substances.

Gradient method according to Example 9:

| 0.00 min | A: 90% | B: 10% |
| 25.00 min | A: 65% | B: 35% |
| 26.00 min | A: 0% | B: 100% |
| 30.00 min | A: 0% | B: 100% |

Example 10: Biotechnological Production of Feruloyl-3-Methoxytyramide

E. coli BL21 (DE3) cells transformed by means of pCDFDuet_Nt4CL1_NtTHT and pMA7-2 were separately cultivated in TB medium (23.6 g/L yeast extract, 11.8 g/L trypton, 9.4 g/L $K_2HPO_4$, 2.2 g/L $KH_2PO_4$, 4 mL/L glycerin) to an optical density of 1.0 at 600 nm and then mixed so that both cultures had an optical density of 0.5 at 600 nm. Then 1 mM isopropyl-R-D-thiogalactopyranoside were added for inducing protein expression and 5 mM L-DOPA and 5 mM ferulic acid were added as a substrate. After incubating the cultures at 30° C. and 150 rpm for 48 h, the fermentation supernatant was analyzed by means of LC-MS as described in Example 9.

Example 11: Enzymatic presentation of (E)-3-(3,4-dimethoxyphenyl)-N-[2-(4-hydroxyphenyl)ethyl]prop-2-enamide starting with (E)-3-(4-hydroxy-3-methoxy-phenyl)-N-[2-(4-hydroxyphenyl)ethyl]prop-2-enamide 0.64 mM (E)-3-(4-hydroxy-3-methoxy-phenyl)-N-[2-(4-hydroxyphenyl)ethyl]prop-2-enamide were mixed with 50 µg CbMOMT and 1.3 mM S-adenosylmethionine in 50 mM Tris buffer, pH 7.5, and incubated for 24 h at 30° C. The reaction mixture obtained was then analyzed using LC-MS as described in Example 9.

Example 12: Enzymatic presentation of dimethoxycinnamoylmethoxytyramide starting with (E)-3-(3,4-dimethoxyphenyl)-N-[2-(4-hydroxyphenyl)ethyl]prop-2-enamide 1.22 mM (E)-3-(3,4-dimethoxyphenyl)-N-[2-(4-hydroxyphenyl)ethyl]prop-2-enamide were mixed together with 1 mg CbMOMT lysate, 1 mg TaOMT2 lysate, or 1 mg GmSOMT lysate and 4.88 mM S-adenosylmethionine in 50 mM Tris buffer, pH 7.5, and incubated for 24 h at 30° C. The reaction mixture obtained was then analyzed using LC-MS as described in Example 9.

Example 13: Analysis of the Conversion of Cinnamic Acids, Phenethylamines, and Cinnamic Acid Amides Using Various Methyltransferases 200 ppm of the substrate to be analyzed were mixed together with double the molar amount of S-adenosylmethionine relative to the substrate and 50 µg enzyme in each buffer (see Table 3) and incubated for 24 h at 30° C. The reaction mixture obtained was then analyzed using LC-MS. The reaction mixtures comprising cinnamic acids or cinnamic acid amides were thereby analyzed as shown in Example 9. Waters Acquity UPLC was used with a Bruker micrOTOF Q-II detector for analyzing the phenethylamine. The sample was separated by means of an Acquity HSS T3 (1.8 µm) separation column with a diameter of 2.1 mm and a length of 150 mm at a column temperature of 50° C. by means of the gradient method shown below. The mobile phase was water with 0.1% formic acid (A) and acetonitrile with 0.09% formic acid (B) at a flow rate of 0.35 ml/min. Retention times were determined and quantitative determination took place according to the external standard method using the corresponding reference substances.

Gradient method according to Example 13:

| | | |
|---|---|---|
| 0.00 min | A: 100% | B: 0% |
| 22.00 min | A: 5% | B: 95% |
| 27.00 min | A: 5% | B: 95% |
| 30.00 min | A: 0% | B: 100% |

TABLE 3

List of buffers used in Example 13

| Protein | Buffer |
|---|---|
| AtCOMT [SEQ ID NO: 23] | 50 mM Tris-HCl, pH 8.8 with 2 mM MgCl$_2$ |
| CbIEMT1 [SEQ ID NO: 35] | 50 mM Tris-HCl, pH 7.5 |
| CbMOMT [SEQ ID NO: 27] | 50 mM Tris-HCl, pH 7.5 |
| CrOMT [SEQ ID NO: 36] | 50 mM Tris-HCl, pH 7.5 |
| GmSOMT [SEQ ID NO: 25] | 50 mM Tris-HCl, pH 7.5 |
| McPFOMT [SEQ ID NO: 24] | 100 mM KPi pH 7.5 with 140 µM MgCl$_2$ |
| MxSafC [SEQ ID NO: 26] | 10 mM HEPES, pH 7.2 with 100 µM MgCl2 |
| PsOMT [SEQ ID NO: 38] | 100 mM HEPES pH 7.7 |
| RcOMT [SEQ ID NO: 37] | 50 mM NaH2PO4 pH 8.0 with 300 mM NaCl |
| SynOMT [SEQ ID NO: 39] | 100 mM KPi pH 7.5 |
| TaOMT2 [SEQ ID NO: 40] | 50 mM Tris-HCl, pH 7.6 |

Example 14: Enzymatic Conversion of Cinnamic Acid Esters and Phenethylamines to the Corresponding Cinnamic Acid Amides 0.1 mmol of the cinnamic acid ester are dissolved with 0.1 mmol of the phenethylamine in 5 mL triethylamine and stirred together with 50 mg immobilized lipase B from *Candida antarctica* (Roche, Mannheim) at 70° C. for 24 h with backflow. The immobilized enzyme is then recaptured by means of filtration. The filtrate was analyzed by means of LC-MS.

Example 15: Producing the Plasmid pD1214_CbMOMT

For the cloning of CbMOMT (SEQ ID NO:7) into a modified pD1214 shuttle vector (provided by DNA2.0, USA), the coding sequence of the gene was amplified using OneTaq polymerase (New England Biolabs, Frankfurt am Main) in a conventional practice known to the person skilled in the art by means of a polymerase chain reaction (PCR). Interfaces for BsaI where thereby generated at the 5'- and 3'-ends of the fragment by means of specific primers (SEQ ID NO:45, SEQ ID NO:46). The PCR preparation was then separated on a 1% agarose gel and the target fragment was elucted out of the gel at a length of 1143 base pairs by means of the QIAprep Spin Miniprep Kit (Qiagen, Hilden). 100 ng of the vector were then incubated at 37° C. for 1 h with 20 ng of the cleaned PCR fragment in a 15 µL reaction preparation with 1×NEB T4 ligase buffer (New England Biolabs, Frankfurt am Main), 0.1 mg/mL BSA (New England Biolabs, Frankfurt am Main), 20 U BsaI (New England Biolabs, Frankfurt am Main), and 100 U NEB T4 DNA ligase (New England Biolabs, Frankfurt am Main), then incubated for 5 min at 50° C. and for 5 min at 80° C. to stop the reaction.

Example 16: Producing the Plasmid pD1214_CbMOMT_SAMS

For cloning SAMS into the shuttle vector pD1214_CbMOMT (see Example 15), the coding sequence of the gene, including the detection sequences for the restriction enzymes BamHI and BglII were amplified in a PCR (Primer: SEQ ID NO:47, SEQ ID NO:48) using OneTaq polymerase (New England Biolabs, Frankfurt am Main) according to prevalent practice known to the person skilled in the art. The PCR preparation was then separated on a 1% agarose gel and the target fragment was elucted out of the gel at a length of 1175 base pairs by means of the QIAprep Spin Miniprep Kit (Qiagen, Hilden). In parallel thereto, 3 µg of the vector pD1214_CbMOMT were incubated for 4 h at 37° C. with 10 U BamHI and 5 U BglII (both from New England Biolabs, Frankfurt am Main) in a 30 µL reaction preparation with 1×NEB buffer 3 (New England Biolabs, Frankfurt am Main). After subsequently adding 1 U Calf Intestine Alkaline Phosphatase (Life Technologies GmbH, Darmstadt), the preparation was incubated for 1 h at 37° C. The preparation was then chromatographically separated on a 1% agarose gel and the linearized vector was elucted from the gel by means of the QIAprep Spin Miniprep Kit (Qiagen, Hilden). For the ligation, 30 fmol of the elucted vector with 90 fmol of the cleaned PCR fragment were mixed together with 5 U ExpressLink T4 DNA ligase (Life Technologies GmbH, Darmstadt) in a 20 µL reaction preparation with 1× ExpressLink ligase buffer (Life Technologies GmbH, Darmstadt) and incubated for 5 min at room temperature.

Example 17: Reproduction of Shuttle Vectors

For reproducing the plasmids produced analogously to Examples 15 and 16, 5 µL of each of the reaction preparations were added to 50 µL each of chemically competent *E. coli* XL1 blue cells, after said cells had been first incubated on ice for 5 minutes. The preparation was then incubated on ice for an additional 30 minutes. The transformation took place in that the suspension was transferred to a thermoblock for 30 s at 42° C. and then to wet ice for 2 min. Then 600

μL LB medium (Carl Roth GmbH, Karlsruhe) were added and the cells were incubated for 1 h at 37° C. and 180 rpm. Finally 200 μL of the culture were spread onto LB agar (Carl Roth GmbH, Karlsruhe) with the associated antibiotic and the Petri dishes were incubated for 16 h at 37° C.

Example 18: Transformation in S. cerevisiae

For the transformation of the plasmid DNA from Example 15 or 16, a main culture was first inoculated with 150 mL YPD medium (Formedium, Great Britain) from an overnight culture of the S. cerevisiae strain BY4741. After reaching an $OD_{600\ nm}$ of ~0.2, the culture was centrifuged, the supernatant discarded, and the resulting pellet resuspended in 1.5 mL 1×TE/1×LiAc buffer (10 mM Tris-HCl, 1 mM EDTA, 0.1 M lithium acetate, pH 7.5). In parallel thereto, 10 μL aliquotes of a 10 mg/mL herring sperm DNA solution (Life Technologies GmbH, Darmstadt) for each plasmid DNA to be transformed were denatured for 5 min at 95° C. and then cooled in a refrigerator. 100 ng of plasmid DNA and 100 μL of the S. Cerevisiae cells resuspended in 1×TE/1×LiAc buffer (10 mM Tris-HCl, 1 mM EDTA, 0.1 M lithium acetate, pH 7.5) are then added to said aliquotes. After adding 600 μL sterile PEG/LiAc solution (40% PEG 4000, 10 mM Tris-HCl, 1 mM EDTA, 0.1 M lithium acetate, pH 7.5), the samples were vortexed for 10 s and then incubated for 30 min at 30° C. and 200 rpm. After adding 70 μL DMSO, a 15-minute incubation at 42° C. took place, followed by cooling on wet ice for 2 min. Then the cells were briefly centrifuged, the supernatant discarded, and the resulting pellet placed in 500 μL 1×TE buffer (10 mM Tris-HCl, 1 mM EDTA, pH 7.5). From this suspension, 100 μL were plated onto corresponding selection media and incubated for 48 h at 30° C.

Example 19: Fermentative Presentation of 3,4-Dimethoxycinnamic Acid Using Saccharomyces cerevisiae Cells S. cerevisiae cells transformed by means of pD1214_CbMOMT or pD1214_CbMOMT_SAMS were cultivated at 30° C. in $SD_{Glu}$-Ura medium (1.9 g/L Yeast Nitrogen Base [Formedium, Great Britain], 0.77 g/L Complete Supplement Mixture without Uracil [Formedium, Great Britain], 20 g/L glucose, 5 g/L ammonium sulfate) to an optical density of 0.2 at 600 nm. For conversion using pD1214_CbMOMT, 1 mM ferulic acid were added to the medium immediately upon reaching the OD, and the preparation was incubated for 48 h at 30° C. and 200 rpm. The reaction mixture obtained was then analyzed using HPLC. For conversion using pD1214_CbMOMT_SAMS the cells were first centrifuged after reaching the OD, the supernatant was discarded, and the resulting pellet was placed in $SD_{Gal}$-Ura medium (1.9 g/L Yeast Nitrogen Base [Formedium, Great Britain], 0.77 g/L Complete Supplement Mixture without Uracil [Formedium, Great Britain], 20 g/L galactose, 5 g/L ammonium sulfate). Then 1 mM ferulic acid was added and the preparation was incubated for 48 h at 30° C. and 200 rpm. The reaction mixture obtained was also analyzed using HPLC as described in Example 7.1.

The invention claimed is:

1. A method for producing a 4-methylized cinnamic acid amide using a recombinant microorganism or fungus and comprising the following steps:
   (i) providing a first recombinant microorganism or fungus comprising:
      (a1) a nucleic acid segment comprising or made of at least one gene coding for a 4'-O-methyltransferase,
      (a2) optionally a nucleic acid segment comprising or made of at least one gene coding for a 3'-O-Methyltransferase,
      (a3) optionally a nucleic acid segment comprising or made of a gene coding for a DOPA-decarboxylase, and
   (b) optionally for fermentative production, a nucleic acid segment comprising or made of a gene coding for an S-adenosylmethionine synthase (SAMS), and
   (ii) providing a second recombinant microorganism or fungus comprising:
      (c) a nucleic acid segment comprising or made of at least one gene coding for a 4-coumarat:CoA-ligase,
      (d) a nucleic acid segment comprising or made of at least one gene coding for a tyramine-N-hydroxycinnamoyltransferase, and
      (e) optionally a nucleic acid segment comprising or made of a gene coding for a DOPA-decarboxylase,
   (iii) cultivating the recombinant microorganisms or fungi according to steps (i) and (ii) under conditions allowing the expression of the nucleic acid segments of (a1)-(e) to produce the corresponding polypeptide products;
   (iv) optionally isolating and optionally purifying the polypeptide products obtained;
   (v) adding a hydroxycinnamic acid and dopamine and/or a dopamine precursor or derivative selected from L-dihydroxyphenylalanine, tyrosine and phenylalanine to the cultivated recombinant microorganisms or fungi according to steps (i) and (ii) for a fermentative conversion, or a phenethylamine and a cinnamic acid ester to the isolated polypeptide products according to step (iv) for an enzymatic conversion; and
   (vi) cultivating or incubating the recombinant microorganisms or fungi or the isolated polypeptide products, optionally adding a lipase, under conditions enabling the conversion of dopamine and/or L-dihydroxyphenylalanine and of a hydroxycinnamic acid to a 4-methylized cinnamic acid amide;
   (vii) optionally isolating and optionally purifying the obtained 4-methylized cinnamic acid amide and further byproducts that are optionally present.

2. The method according to claim 1, wherein the 4-methylized cinnamic acid amide is selected from the group consisting of rubemamine [(2E)-3-(3,4-dimethoxyphenyl)-N-[2-(3,4-dimethoxyphenyl)ethyl]prop-2-enamide], and 3,4-dimethoxycinnamoylmethoxytyramide [(2E)-3-(3,4-dimethoxyphenyl)-N-[2-(4-methoxyphenyl)ethyl]prop-2-enamide].

3. The method according to claim 1, wherein the 4'-O-methyltransferase, or the nucleic acid segment coding the 4'-O-methyltransferase, is selected from SEQ ID Nos: 5, 6, 7, 8, 9, 15, 17, 18, 25, 26, 27, 28, 29, 35, 37, 38, 85, and 86, and the 3'-O-methyltransferase, or the nucleic acid segment coding the 3'-O-methyltransferase, is selected from SEQ ID Nos: 3, 4, 16, 19, 20, 23, 24, 36, 39, and 40, and the S-adenosylmethionine synthase, or the nucleic acid segment coding the S-adenosylmethionine synthase is selected from SEQ ID Nos: 10, 30, and 65 through 72, and the DOPA-decarboxylase, or the nucleic acid segment coding the DOPA-decarboxylase is selected from SEQ ID Nos: 1, 2, 21, 22, and 59 through 64, and the tyramine-N-hydroxycinnamoyltransferase, or the nucleic acid segment coding the tyramine-N-hydroxycinnamoyltransferase, is selected from SEQ ID Nos: 13, 14, 33, 34, and 79 through 82, and the 4-coumarat:CoA-ligase, or the nucleic acid segment coding the 4-coumarat:CoA-ligase, is selected from SEQ ID NOs: 11, 12, 31, 32, and 73 through 78, and the lipase is a lipase B selected from SEQ ID NOs:83 and 84; wherein the polypeptides and the sequences coding the polypeptides comprise sequences having at least 80% sequence homology with the corresponding SEQ ID Nos, under the condition that a polypeptide sequence thus modified and having a corresponding degree of homology still fulfills the same enzymatic function as the corresponding non-modified polypeptide having the same SEQ ID NO.

4. The method according to claim 2, wherein the 4'-O-methyltransferase, or the nucleic acid segment coding the 4'-O-methyltransferase, is selected from SEQ ID Nos: 5, 6, 7, 8, 9, 15, 17, 18, 25, 26, 27, 28, 29, 35, 37, 38, 85, and 86, and the 3'-O-methyltransferase, or the nucleic acid segment coding the 3'-O-methyltransferase, is selected from SEQ ID Nos: 3, 4, 16, 19, 20, 23, 24, 36, 39, and 40, and the S-adenosylmethionine synthase, or the nucleic acid segment coding the S-adenosylmethionine synthase is selected from SEQ ID Nos: 10, 30, and 65 through 72, and the DOPA-decarboxylase, or the nucleic acid segment coding the DOPA-decarboxylase is selected from SEQ ID NOs: 1, 2, 21, 22, and 59 through 64, and the tyramine-N-hydroxycinnamoyltransferase, or the nucleic acid segment coding the tyramine-N-hydroxycinnamoyltransferase, is selected from SEQ ID Nos: 13, 14, 33, 34, and 79 through 82, and the 4-coumarat:CoA-ligase, or the nucleic acid segment coding the 4-coumarat:CoA-ligase, is selected from SEQ ID NOs: 11, 12, 31, 32, and 73 through 78, and the lipase is a lipase B selected from SEQ ID NOs:83 and 84; wherein the polypeptides and the sequences coding the polypeptides comprise sequences having at least 80% sequence homology with the corresponding SEQ ID Nos, under the condition that a polypeptide sequence thus modified and having a corresponding degree of homology still fulfills the same enzymatic function as the corresponding non-modified polypeptide having the same SEQ ID NO.

5. The method according to claim 1, wherein the hydroxycinnamic acid of step (v) is caffeic acid or ferulic acid.

6. The method according to claim 5, wherein the caffeic acid or ferulic acid is esterified on a hemicellulose.

7. The method according to claim 1, wherein for an enzymatic conversion in step (v), S-adenosylmethionine is also added to the products of expression according to step (iv).

8. The method according to claim 1, wherein for an enzymatic conversion in step (v), the phenethylamine is selected from the group consisting of dopamine, tyrosine, phenylalanine, L-dihydroxyphenylalanine, 3-methoxytyramine, 3-hydroxy-4-methoxyphenethylamine and 3,4-dimethoxyphenethylamine.

9. The method according to claim 1, wherein the cinnamic acid ester of step (v) is selected from esters of caffeic acid, ferulic acid, isoferulic acid, and 3,4-dimethoxycinnamic acid.

10. The method according to claim 1, wherein the wherein the microorganism or fungus is selected from the group of *Eschericia coli* spp., *Bacillus* spp., *Saccharomyces* spp., *Kluyveromyces* spp, *Aspergillus* spp., and *Trichoderma* spp.

11. The method according to claim 10, wherein the microorganism or fungus is *Eschericia coli* spp. or *Saccharomyces* spp.

12. The method according to claim 3, wherein the polypeptides and the sequences coding the polypeptides comprise sequences having at least 90% sequence homology with the corresponding SEQ ID Nos, under the condition that a polypeptide sequence thus modified and having a corresponding degree of homology still fulfills the same enzymatic function as the corresponding non-modified polypeptide having the same SEQ ID NO.

13. The method according to claim 3, wherein the polypeptides and the sequences coding the polypeptides comprise sequences having at least 95% sequence homology with the corresponding SEQ ID Nos, under the condition that a polypeptide sequence thus modified and having a corresponding degree of homology still fulfills the same enzymatic function as the corresponding non-modified polypeptide having the same SEQ ID NO.

14. The method according to claim 4, wherein the polypeptides and the sequences coding the polypeptides comprise sequences having at least 90% sequence homology with the corresponding SEQ ID Nos, under the condition that a polypeptide sequence thus modified and having a corresponding degree of homology still fulfills the same enzymatic function as the corresponding non-modified polypeptide having the same SEQ ID NO.

15. The method according to claim 4, wherein the polypeptides and the sequences coding the polypeptides comprise sequences having at least 95% sequence homology with the corresponding SEQ ID Nos, under the condition that a polypeptide sequence thus modified and having a corresponding degree of homology still fulfills the same enzymatic function as the corresponding non-modified polypeptide having the same SEQ ID NO.

* * * * *

SEQUENCE LISTING

```
<160> NUMBER OF SEQ ID NOS: 86

<210> SEQ ID NO 1
<211> LENGTH: 1428
<212> TYPE: DNA
<213> ORGANISM: Drosophila melanogaster
<220> FEATURE:
<223> OTHER INFORMATION: (DmDDC)

<400> SEQUENCE: 1
atggaggcac cggaatttaa agattttgcc aaaacgatgg tggactttat cgcagaatat        60
ctggaaaata ttcgtgaacg tcgtgttctg ccggaagtta aaccgggtta tctgaaaccg       120
ctgattccgg atgcagcacc ggaaaaacct gaaaaatggc aggatgttat gcaggatatt       180
gaacgtgtta ttatgcctgg tgttacccat tggcatagcc cgaaatttca tgcatatttt       240
ccgaccgcaa atagctatcc ggcaattgtt gcagatatgc tgagcggtgc aattgcctgt       300
attggtttta cctggattgc aagtccggca tgtaccgaac tggaagttgt tatgatggat       360
tggctgggta aaatgctgga actgcctgca gaatttctgg catgtagcgg tggtaaaggt       420
ggtggtgtta ttcagggcac cgcaagcgaa agcacctgg ttgcactgct gggtgcaaaa       480
gcaaaaaaac tgaaagaagt gaaagaactg cacccggaat gggatgaaca taccattctg       540
ggtaaactgg ttggttattg tagcgatcag gcacatagca gcgttgaacg tgcaggtctg       600
ctgggaggtg ttaaactgcg tagcgttcag agcgaaaatc atcgtatgcg tggtgcagcc       660
ctggaaaaag caattgaaca ggatgttgca gaaggtctga ttccgttta tgcagttgtt       720 accctgggca ccaccaatag ctgtgcattt gattatctgg atgaatgtgg tccggtgggc       780
aataaacata atctgtggat tcatgttgat gcagcatatg caggtagcgc atttatttgt       840
ccggaatatc gtcatctgat gaaaggtatt gaaagcgcag atagctttaa cttcaatccg       900
```

```
cataaatgga tgctggtgaa ttttgattgt agcgcaatgt ggctgaaaga tccgagctgg    960
gttgttaatg catttaatgt tgatccgctg tacctgaaac atgatatgca gggtagtgca   1020
ccggattatc gccattggca gattccgctg ggtcgtcgtt ttcgtgcact gaaactgtgg   1080
tttgttctgc gtctgtatgg tgttgaaaac ctgcaggccc atattcgtcg tcattgtaat   1140
tttgcgaaac agtttggtga tctgtgtgtt gccgatagcc gttttgaact ggcagcagaa   1200
attaacatgg gtctggtttg ctttcgtctg aaaggtagca atgaacgtaa tgaagcactg   1260
ctgaaacgta ttaatggtcg cggtcatatt catctggttc cggcaaaaat caaagatgtg   1320
tatttcctgc gtatggccat ttgcagccgt tttacacaga gcaagatat ggaatatagc    1380 tggaaagaag ttagcgcagc agcagatgaa atggaacaag aacagtaa              1428
```

<210> SEQ ID NO 2
<211> LENGTH: 1614
<212> TYPE: DNA
<213> ORGANISM: Argemone mexicana
<220> FEATURE:
<223> OTHER INFORMATION: (AmDDC)

<400> SEQUENCE: 2

```
atgggtagcc tgaataccga agatgttctg gaaaacaata ccgcatttgg tgttaccaat     60
ccgctggaac cggaagaatt tcgtaaacag ggtcatatga tcatcgattt tctgccgat    120 tattatcgcg acatcgaaaa atatccggtt cgtagccagg ttgaaccggg ttatctgcgt   180
aaacgtctgc cggaaaccgc accgtataat ccggaaagca tggaaagtat tctggaagat   240
gtgcagaatg aaatcattcc gggtattacc cattggcaga gcccgaatta tttcgcatat   300
tttccgagca gcggtagcat tgcaggtttt ctgggtgaaa tgctgagcac cggttttaat   360
gttgttggct ttaattggat gagcagtccg gcagcaaccg aactggaaag cattgttatg   420
gattggctgg caaaatgct gaaactgccg aaaagctttc tgtttagcgg taatggtggt   480
ggtgttctgc agggcaccac ctgtgaagca attctgtgta ccctgaccgc agcacgtgat   540
cgtatgctga caaaattgg tcgtgaaaat attggtcgtc tggttgttta tggtagcgat   600
cagacccatt gtgcactgca gaaagcagca cagattgcag gtattaatcc gaaaaacttt   660
cgtgccgttc agacctttaa agcacatagc tttggtctga gcgcagatac cctgcgtaaa   720
gttattcgta gtgatgttga agcaggtctg attccgctgt tgtttgtcc gaccgttggt   780 acaaccagca gcaccgcagt tgatccgatt ggtccgattt gtgaagttgc caaagaatat   840
gaaatgtggg ttcatgttga tgcagcatat gcaggtagcg catgtatttg tccggaattt   900
cgtcatttta ttgacggtgt tgaaaacgcc gatagctttt cactgaatgc ccacaaatgg   960 tttttttacca ccctggattg ttgttgcctg tgggttaaag atccgagcgc actggttaaa  1020
gcactgagca ccaatccgga atatctgcgc aataaagcca ccgaaagcaa acaggttgtg  1080
gattataaag attggcagat tgcactgagc cgtcgttttc gtagcatgaa actgtggatg  1140
gttctgcgta ttatggtgt tgcaaacctg cgcaatttc tgcgtagcca tgttaaaatg   1200
gccaaacagt ttgaaggcct gattgcaagc gataaccgtt ttgaaatttg tgttccgcgt  1260
acctttgcaa tggtttgttt tcgtctgctg cctccgaaaa gcacccgtga taatcgtgtt  1320
cgtgaagaag atggtctgtt tgttagcggt gttcatgatc acgaaaataa catcaacgaa  1380
gatgaccatc tgctggtcgt tgcaaataaa ctgaatcaga tctacctgga aaaagtgaat  1440
gcaaccggta gcctgtatat gacccatgca gttgttggtg gcatttatat gattcgtttt  1500
```

-continued

| gcagttggta gcaccctgac agaagaacgt catattacac atgcctggaa agttctgcaa | 1560 |
| gaacatgcag ataccattct gggcaccttt aatctggcag attttagctg ttaa | 1614 |

<210> SEQ ID NO 3
<211> LENGTH: 1092
<212> TYPE: DNA
<213> ORGANISM: Arabidopsis thaliana
<220> FEATURE:
<223> OTHER INFORMATION: (AtCOMT)

<400> SEQUENCE: 3

| atgggttcaa cggcagagac acaattaact ccggtgcaag tcaccgacga cgaagctgcc | 60 |
| ctcttcgcca tgcaactagc cagtgcttcc gttcttccga tggctttaaa atccgcctta | 120 |
| gagcttgacc ttcttgagat tatgccaag aatggttctc ccatgtctcc taccgagatc | 180 |
| gcttctaaac ttccgaccaa aaatcctgaa gctccggtca tgctcgaccg tatcctccgt | 240 |
| cttcttacgt cttactccgt cttaacctgc tccaaccgta aactttccgg tgatggcgtt | 300 |
| gaacggattt acgggcttgg tccggtttgc aagtatttga ccaagaacga agatggtgtt | 360 |
| tccattgctg ctctttgtct tatgaaccaa gacaaggttc tcatggaaag ctggtaccat | 420 |
| ttgaaggatg caattcttga tggtgggatt ccattcaaca aggcttatgg aatgagcgcg | 480 |
| ttcgagtacc acggactga ccctagattc aacaaggtct ttaacaatgg aatgtctaac | 540 |
| cattccacaa tcaccatgaa gaagattctt gagacctata gggttttga aggattgact | 600 |
| tctttggttg atgttggtgg tggcattggt gctacactca aaatgattgt ctccaagtac | 660 |
| cctaatctta aaggcatcaa ctttgatctc ccacatgtca tcgaagatgc tccttctcat | 720 |
| cctggtattg agcatgttgg aggagatatg tttgtaagtg tccctaaagg tgatgccata | 780 |
| ttcatgaagt ggatatgtca tgactggagt gacgaacatt gcgtgaaatt cttgaagaac | 840 |
| tgctacgagt cacttccaga ggatggaaaa gtgatattag cagagtgtat acttccagag | 900 |
| acaccagact caagcctctc aaccaaacaa gtagtccatg tcgattgcat tatgttggct | 960 |
| cacaatcccg gaggcaaaga acgaaccgag aaagagtttg aggcattagc caaagcatca | 1020 |
| ggcttcaagg gcatcaaagt tgtctgcgac gcttttggtg ttaaccttat tgagttactc | 1080 |
| aagaagctct aa | 1092 |

<210> SEQ ID NO 4
<211> LENGTH: 714
<212> TYPE: DNA
<213> ORGANISM: Mesembryanthemum crystallinum
<220> FEATURE:
<223> OTHER INFORMATION: (McPFOMT)

<400> SEQUENCE: 4

| atggattttg ctgtgatgaa gcaggtcaaa aatacaggat tgctacagag tgaggagtta | 60 |
| tgccagtata ttctccgaac tagtgtctat ccgcgagaag cagggttcct caaggaactc | 120 |
| agggaagcca atgaaagtca cccagactct tatatgtcga cttcaccact tgctggacaa | 180 |
| ttgatgtcat tcgttctaaa attagtgaat gcaagaagaa ctattgaagt tggagtcttt | 240 |
| acaggatact ccctcttact cactgctctt tcaattcctg atgatggaaa gattacggca | 300 |
| attgatttcg acagagaggc atatgagatt ggcttgccat ttatcagaaa agctggtgtg | 360 |
| gagcacaaaa tcaacttcat tgaatcggat gctatgctag ctcttgacaa tcttctgcaa | 420 |
| ggacaagaga gcgaggggag ttacgacttt ggctttgttg atgcggacaa acctaactac | 480 |
| atcaagtacc atgagaggtt gatgaaacta gtcaaggtgg gtggcatagt cgcttatgac | 540 |

| aacacattat ggggtggaac tgtagcccag cctgaatccg aagtaccaga tttcatgaag | 600 |
| gaaaacagag aagctgttat tgaactcaac aagttgcttg ctgctgatcc tcgtatcgag | 660 |
| attgtacatc ttcctttggg tgatggtatc actttctgca ggcgtcttta ttga | 714 |

<210> SEQ ID NO 5
<211> LENGTH: 1077
<212> TYPE: DNA
<213> ORGANISM: Glycine max
<220> FEATURE:
<223> OTHER INFORMATION: (GmSOMT)

<400> SEQUENCE: 5

| atggcgtcac cgttgaataa tggccgcaaa gccagtgaga ttttccaggg tcaagcgttg | 60 |
| ctgtacaaac atcttttagg gtttatcgac agcaaatgtc tgaaatggat ggtgagctg | 120 |
| gatattccgg atatcattca ctcccatagc catggacagc ctattacctt ctctgaattg | 180 |
| gtttcgatcc tgcaagttcc tccgaccaaa acacgtcagg ttcagtcgtt gatgcgctat | 240 |
| cttgcgcata atggtttctt tgaaattgtg cgcattcacg ataacatcga agcctatgcg | 300 |
| ttaactgctg ccagtgaact gcttgtgaaa agctcggaat tatccttagc accaatggtg | 360 |
| gagtattttc tggaaccgaa ttgtcagggt gcgtggaatc agctgaaacg ttgggtacat | 420 |
| gaagaggatc tgacggtctt tggtgtatct ctgggcactc cattctggga tttcatcaac | 480 |
| aaagacccag catataacaa gtcctttaac gaagctatgg catgtgatag ccaaatgctc | 540 |
| aatctggcgt ttcgcgattg caattgggtc tttgaaggcc tggaatcgat tgtggatgtg | 600 |
| ggcggtggta cgggcattac agccaaaatc atttgcgaag catttccgaa gttgaaatgc | 660 |
| atggtactcg aacgtcccaa cgtagtggag aacctgtcag gcagcaacaa tctgaccttt | 720 |
| gttggtgggg acatgttcaa atgcattccg aaagcggatg cggtgcttct gaaactggtt | 780 |
| ctgcacaatt ggaacgacaa tgactgcatg aagatcctgg aaaactgcaa ggaagccatt | 840 |
| tcaggagaga gtaaaaccgg caaagtcgtc gttattgaca ccgtgattaa cgagaacaaa | 900 |
| gacgaacgcc aagttaccga actgaaactc ctgatggatg tccacatggc ctgtatcatc | 960 |
| aacggcaaag agcggaaaga agaggattgg aagaaactgt tcatggaagc tgggttccag | 1020 |
| tcttacaaga ttagcccctt tacgggctac ttaagtctca tcgaaatcta tccgtaa | 1077 |

<210> SEQ ID NO 6
<211> LENGTH: 663
<212> TYPE: DNA
<213> ORGANISM: Myxococcus xanthus
<220> FEATURE:
<223> OTHER INFORMATION: (MxSafC)

<400> SEQUENCE: 6

| atgatccacc acgtcgaatt gacacagtcc gtcctgcagt acatccgcga cagttccgtg | 60 |
| agggacaacg acatccttcg cgacctgcga gaggagacgt cgaagctccc cctgcgcacg | 120 |
| atgcagattc ctcccgagca ggggcagctc ctgagcctgc tggtgcgcct catcggcgcg | 180 |
| cgcaagacgc tcgaggtggg cgtcttcacc ggctatagca ccctgtgtgc cgcgctcgcg | 240 |
| ctgcccgccg atgggcgcgt catcgcgtgc gacctgagcg aggagtgggt ctccatcgcg | 300 |
| cgccgctact ggcagcgggc gggcgtggcg gatcgcatcg aggtccggct ggcgacgcc | 360 |
| caccattccc tggaggcgct ggtcggcagc gagcaccgcg ggacgttcga cctcgcgttc | 420 |
| atcgatgcgg acaaggagag ctacgacttc tactacgagc acgcgctgcg gctggtgcgt | 480 |

| | |
|---|---|
| cccggcgggt tgatcatcct cgacaacacg ctgtggtccg ggaaggtcgc cgacccgagc | 540 |
| gtcgtcgggg acccggagac ggactcgctg cggcgcatca acgccaagct cctgactgac | 600 |
| gaacgggtgg acctcagcat gctcccaatc gctgacggac tgaccctcgc tcgcaagcgc | 660 |
| tag | 663 |

<210> SEQ ID NO 7
<211> LENGTH: 1107
<212> TYPE: DNA
<213> ORGANISM: Clarkia breweri
<220> FEATURE:
<223> OTHER INFORMATION: (CbMOMT)

<400> SEQUENCE: 7

| | |
|---|---|
| atgggttcga caggcaatgc ggaaattcag atcattccga cacatagctc cgacgaagaa | 60 |
| gcgaatttgt ttgcgatgca actggcctca gctgcggttc tgcccatggc gctgaaagcc | 120 |
| gcgattgagc ttgatgtgtt agagattatg gccaaatccg taccaccaag cggctatatt | 180 |
| tcaccggccg aaattgctgc tcaactcccg acgactaatc ggaagcacc ggtcatgttg | 240 |
| gatcgcgttt tgcggttact ggcgagctat tcggtagtga cgtataccct gcgtgagctg | 300 |
| ccgtctggca aagtcgaacg tctgtacgga ctggcgccgg tgtgcaaatt cctgactaag | 360 |
| aatgaggatg gggtttctct cgcaccctt ctgctccttg cgacggataa agtcctgctg | 420 |
| gaaccatggt tctacctgaa agacgccatt ctggaaggcg gcattccgtt caacaaggca | 480 |
| tacggaatga acatcttcga ttactttggc actgatcacc gcatcaacaa agtattcaac | 540 |
| aaagggatgc tagcaatag taccatcacc atgaagaaaa ttctggagat gtacaatggg | 600 |
| tttgaaggcc tgaccaccat cgtggatgtt ggtggtggta caggcgcagt tgcctccatg | 660 |
| attgtgcga atatccgtc gatcaatgcc attaactttg acttacccca tgtcattcag | 720 |
| gatgcgcctg cgtttagcgg tgttgaacac ttaggtgggg acatgtttga cggtgtgcca | 780 |
| aaaggcgatg cgatctttat caaatggatc tgtcatgact ggagcgatga acactgtctg | 840 |
| aaacttctta gaactgcta tgctgccttg ccggatcatg gcaaagtgat cgttgccgaa | 900 |
| tacattctgc ctccgtcgcc tgatccgagt attgcaacca agtagtcat ccataccgac | 960 |
| gctctgatgc tcgcctataa ccctggtgga aaagagcgta cggagaaaga attccaggca | 1020 |
| ttagcaatgg cgagtggctt tcgcggtttt aaggtggcat catgcgcttt caacacctat | 1080 |
| gtgatggaat tcctgaaaac ggcctaa | 1107 |

<210> SEQ ID NO 8
<211> LENGTH: 1107
<212> TYPE: DNA
<213> ORGANISM: Clarkia breweri
<220> FEATURE:
<223> OTHER INFORMATION: (CbMOMT-L322N)

<400> SEQUENCE: 8

| | |
|---|---|
| atgggttcga caggcaatgc ggaaattcag atcattccga cacatagctc cgacgaagaa | 60 |
| gcgaatttgt ttgcgatgca actggcctca gctgcggttc tgcccatggc gctgaaagcc | 120 |
| gcgattgagc ttgatgtgtt agagattatg gccaaatccg taccaccaag cggctatatt | 180 |
| tcaccggccg aaattgctgc tcaactcccg acgactaatc ggaagcacc ggtcatgttg | 240 |
| gatcgcgttt tgcggttact ggcgagctat tcggtagtga cgtataccct gcgtgagctg | 300 |
| ccgtctggca aagtcgaacg tctgtacgga ctggcgccgg tgtgcaaatt cctgactaag | 360 |
| aatgaggatg gggtttctct cgcaccctt ctgctccttg cgacggataa agtcctgctg | 420 |

```
gaaccatggt tctacctgaa agacgccatt ctggaaggcg gcattccgtt caacaaggca    480
tacggaatga acatcttcga ttactttggc actgatcacc gcatcaacaa agtattcaac    540
aaagggatgt ctagcaatag taccatcacc atgaagaaaa ttctggagat gtacaatggg    600
tttgaaggcc tgaccaccat cgtggatgtt ggtggtggta caggcgcagt tgcctccatg    660
attgtggcga aatatccgtc gatcaatgcc attaactttg acttacccca tgtcattcag    720
gatgcgcctg cgtttagcgg tgttgaacac ttaggtgggg acatgtttga cggtgtgcca    780
aaaggcgatg cgatctttat caaatggatc tgtcatgact ggagcgatga acactgtctg    840
aaacttctta agaactgcta tgctgccttg ccggatcatg gcaaagtgat cgttgccgaa    900
tacattctgc ctccgtcgcc tgatccgagt attgcaacca agtagtcat ccataccgac     960 gctaacatgc tcgcctataa ccctggtgga aaagagcgta cggagaaaga attccaggca    1020
ttagcaatgg cgagtggctt cgcggttttt aaggtggcat catgcgcttt caacacctat    1080
gtgatggaat tcctgaaaac ggcctaa                                        1107
```

<210> SEQ ID NO 9
<211> LENGTH: 1107
<212> TYPE: DNA
<213> ORGANISM: Clarkia breweri
<220> FEATURE:
<223> OTHER INFORMATION: (CbMOMT-T133S)

<400> SEQUENCE: 9

```
atgggttcga caggcaatgc ggaaattcag atcattccga cacatagctc cgacgaagaa     60
gcgaatttgt ttgcgatgca actggcctca gctgcggttc tgcccatggc gctgaaagcc    120
gcgattgagc ttgatgtgtt agagattatg gccaaatccg taccaccaag cggctatatt    180
tcaccggccg aaattgctgc tcaactcccg acgactaatc cggaagcacc ggtcatgttg    240
gatcgcgttt gcggttact ggcgagctat tcggtagtga cgtataccct gcgtgagctg     300
ccgtctggca aagtcgaacg tctgtacgga ctggcgccgg tgtgcaaatt cctgactaag    360
aatgaggatg gggtttctct cgcaccctt ctgctctcgg cgacggataa agtcctgctg     420
gaaccatggt tctacctgaa agacgccatt ctggaaggcg gcattccgtt caacaaggca    480
tacggaatga acatcttcga ttactttggc actgatcacc gcatcaacaa agtattcaac    540
aaagggatgt ctagcaatag taccatcacc atgaagaaaa ttctggagat gtacaatggg    600
tttgaaggcc tgaccaccat cgtggatgtt ggtggtggta caggcgcagt tgcctccatg    660
attgtggcga aatatccgtc gatcaatgcc attaactttg acttacccca tgtcattcag    720
gatgcgcctg cgtttagcgg tgttgaacac ttaggtgggg acatgtttga cggtgtgcca    780
aaaggcgatg cgatctttat caaatggatc tgtcatgact ggagcgatga acactgtctg    840
aaacttctta agaactgcta tgctgccttg ccggatcatg gcaaagtgat cgttgccgaa    900
tacattctgc ctccgtcgcc tgatccgagt attgcaacca agtagtcat ccataccgac     960 gctctgatgc tcgcctataa ccctggtgga aaagagcgta cggagaaaga attccaggca    1020
ttagcaatgg cgagtggctt cgcggttttt aaggtggcat catgcgcttt caacacctat    1080
gtgatggaat tcctgaaaac ggcctaa                                        1107
```

<210> SEQ ID NO 10
<211> LENGTH: 1155
<212> TYPE: DNA
<213> ORGANISM: Saccharomyces cereviasiae
<220> FEATURE:

<223> OTHER INFORMATION: (ScSAMS)

<400> SEQUENCE: 10

```
atgtccaaga gcaaaacttt cttatttacc tctgaatccg tcggtgaagg tcacccagac        60
aagatttgtg accaagtttc tgatgctatt ttggacgctt gtttagaaca agatccattc       120
tccaaggttg cctgtgaaac agctgccaaa actggtatga ttatggtttt cggtgaaatt       180
accaccaaag ctagacttga ctaccaacaa atagtaagag ataccatcaa gaagattggt       240
tatgacgatt ctgccaaggg tttcgactac aagacatgta atgttttagt agctatcgaa       300
caacaatctc cagatatcgc tcaaggtctg cactatgaaa agagcttaga agacttaggt       360
gctggtgacc aaggtataat gtttggttac gctacagacg aaactccaga agggttacca       420
ttgaccattc ttttggctca caaattgaac atggctatgg cagatgctag aagagatggt       480
tctctcccat ggttgagacc agacacaaag actcaagtca ctgtcgaata cgaagacgac       540
aatggtagat gggttccaaa gaggatagat accgttgtta tttctgctca acatgctgat       600
gaaatttcca ccgctgactt gagaactcaa cttcaaaaag atattgttga aaaggtcata       660
ccaaaggata tgttagacga aaataccaaa tatttcatcc aaccatccgg tagattcgtc       720
atcggtggtc ctcaaggtga cgctggtttg accggtagaa agattattgt cgacgcttac       780
ggtggtgcct catccgtcgg tggtggtgcc ttctccggta aggactattc caaggtcgat       840
cgttccgctg cttacgctgc tagatgggtt gccaagtctc tagttgccgc tggtttgtgt       900
aagagagtcc aagtccaatt ttcatatgct attggtattg ctgaaccatt gtctttacat       960
gtggacacct atggtacagc tacaaaatca gatgacgaaa tcattgaaat tattaagaag      1020
aacttcgact tgagaccagg tgtgttagta aaggaattag attggctag accaatttac       1080 ttaccaaccg cttcttatgg tcacttcact aatcaagagt actcatggga aaaaccaaag      1140
aaattggaat tttaa                                                       1155
```

<210> SEQ ID NO 11
<211> LENGTH: 1671
<212> TYPE: DNA
<213> ORGANISM: Arabidopsis thaliana
<220> FEATURE:
<223> OTHER INFORMATION: (At4CL2)

<400> SEQUENCE: 11

```
atgaccacgc aagacgtgat tgtgaatgac cagaatgacc agaaacaatg cagcaatgac        60
gtgatctttc ggagtcgctt accagacatt tacattccga accatctgcc cctgcatgat       120
tatattttcg aaaacattag cgagtttgcg gccaaaccgt gtctgatcaa cgggcctaca       180
ggcgaagtat acacctatgc ggacgttcac gttacttcgc gcaaactggc cgcaggcttg       240
cataatctgg gagtcaaaca gcacgatgtg gtcatgatct tgctgcctaa ttccccggaa       300
gttgttctga cctttctggc ggcgagcttt atcggtgcga ttacgaccag tgcgaatccg       360
ttcttcactc cggccgaaat cagcaaacag gcgaaagctt cggcagcaaa gctgattgtg       420
acccaaagcc gttatgtcga taaaatcaag aaccttcaaa acgatggtgt gctgattgtc       480
acgaccgata tgatgctat cccggagaat tgccttcgct ctctgagct acacagtcg        540 gaagaaccac gcgtagattc gattccggag aagattagtc cggaagatgt tgtagcgttg       600
ccatttagct cgggcaccac aggttttacc aaaggtgtca tgctgactca caagggttta       660
gtgacttccg tagcccaaca ggtagatggc gaaaatccca acctctactt taaccgcgac       720
gatgtgattc tttgcgtttt accgatgttc cacatttatg ccctgaattc gattatgctg       780
```

```
tgttcactcc gcgttggtgc caccatcctc attatgccga aatttgagat cacgctgctg    840
ttggaacaga ttcagcgctg caaggtgacc gttgccatgg ttgttccgcc aatcgtactc    900
gcgattgcga atcccctga aactgaaaag tatgacctga gttccgtgcg tatggtcaag    960
tctggggctg ccccattagg caaagaactc gaagatgcaa tttcagcgaa attcccgaat   1020
gccaaattag ggcaaggcta tggtatgacg gaagcaggcc cggtactggc catgagttta   1080
ggctttgcca agaaccgtt tccggttaaa agcggtgcgt gtgggacagt ggtgcgtaat    1140
gctgagatga aaatcctgga tcccgatacg ggtgattctc tgccgcgtaa caaaccaggc   1200
gaaatctgta ttcgtggaaa ccagatcatg aaaggctatc tgaacgatcc tcttgctacc   1260
gcatcaacga ttgacaaaga cggatggctg cataccggag atgtgggctt catcgatgac   1320
gacgatgaac tgttcattgt cgaccgcctg aaagagttga tcaaatacaa aggttttcag   1380
gtggcgccag ccgaactgga atctctgctg atcggtcatc cggagattaa cgatgtcgct   1440
gtggtagcaa tgaaggagga agatgctggg gaagtccctg tggcattcgt tgtccgctct   1500
aaagactcaa acatcagcga ggatgaaatc aagcagtttg tctccaaaca ggttgtgttt   1560
tacaaacgca ttaacaaagt gttctttacc gatagcattc cgaaagcgcc tagcggcaaa   1620
attcttcgga aggatttgcg tgcacgtctg gcgaatggct tgatgaacta a            1671
```

<210> SEQ ID NO 12  
<211> LENGTH: 1644  
<212> TYPE: DNA  
<213> ORGANISM: Nicotiana tabacum  
<220> FEATURE:  
<223> OTHER INFORMATION: (Nt4CL1)

<400> SEQUENCE: 12

```
atgccgatgg aaacgactac agaaaccaaa caaagcggtg atctgatctt tcgctcaaaa     60
ctgccggata tctatattcc gaaacactta ccattgcact catattgctt cgagaacatc    120
tccgagttct cctctcgtcc ctgcctgatt aatggcgcga atgatcagat ttacacgtat    180
gccgaagtcg aattgacttg tcgcaaagtc gcggttggtc tgaacaaatt agggatccag    240
cagaaggata ccattatgat cttattaccc aattccccgg aatttgtgtt cgcgtttatg    300
ggcgcttctt atctgggcgc aattagtacc atggcaaatc cgctgtttac ccctgccgaa    360
gtggttaaac aagcgaaagc ctcttcagct aagattatca ttacccagag ctgctttgtc    420
ggtaaagtga aggattatgc gtcggaaaac gatgtcaaag tcatctgcat tgatagcgct    480
ccagaaggat gtctccattt ctccgagctg acacaatcgg acgaacatga gattccggaa    540
gtgaaaattc agccggacga cgttgtagcg cttccctata gctcgggtac tacgggtctg    600
ccaaaagggg tgatgttgac ccacaaaggt ctggtaacct ccgtggccca acaagtcgat    660
ggcgaaaatg cgaatctgta tatgcatagc gaggatgtcc tgatgtgcgt tctgccactc    720
tttcacattt actcgctgaa ctcgattttg tcgtgtggcc ttcgtgttgg cgctgccatc    780
ctgattatgc agaaatttga cattgccccg tttctggaat tgatccagaa gtataaagtg    840
tcaatcggcc cctttgtccc gcctattgtg ctggcgattg cgaagagccc gattgtggat    900
agctacgatt taagtagcgt acgtacggtg atgtctggtg cagccccgtt gggtaaagaa    960
ctcgaggacg ctgtgcgcac caagtttccg aacgccaaac tgggtcaggg ctatgggatg   1020
acggaagcag gccagttttt agccatgtgt ctggcatttg cgaagaacc gttcgacatc   1080 aaatcgggag cttgtggcac cgtagtacgt aacgccgaga tgaaaattgt tgatcctgat   1140
```

| | |
|---|---|
| accggatgca gtctgccgcg taatcagcct ggcgaaatct gcattcgcgg cgaccagatc | 1200 |
| atgaaagggt accttaacga tcctgaagct actacccgca cgattgacaa ggaaggttgg | 1260 |
| ctgcatacag gcgatatcgg tttcattgac gaagatgacg aactgttcat tgttgatcgg | 1320 |
| ctcaaagagc tgattaagta caagggcttt caggttgcac cggcagagat tgaagcgctc | 1380 |
| ctgctgaacc atcctaacat cagtgatgcg gcagttgtgc cgatgaaaga cgaacaagcc | 1440 |
| ggggaggtgc cagtcgcatt tgtggtacgc tctaatggaa gcgccattac ggaagatgag | 1500 |
| gtgaaagact tcatcagtaa acaggtcatc ttctacaaac gggtgaaacg cgtattcttc | 1560 |
| gttgaaacag ttccgaaaag cccaagtggc aaaatccttc gcaaagatct gcgtgcgcgc | 1620 |
| cttgcggcgg gtgtgccgaa ctaa | 1644 |

<210> SEQ ID NO 13
<211> LENGTH: 681
<212> TYPE: DNA
<213> ORGANISM: Nicotiana tabacum
<220> FEATURE:
<223> OTHER INFORMATION: (NtTHT)

<400> SEQUENCE: 13

| | |
|---|---|
| atggctacga cgaataacaa gaacctgacc attaccgaga aagtctatgt tcgtgttcgg | 60 |
| ttagcgaatg aagcggacat ttcgcacatc tacaaactct ctatcaaatc catgagtat | 120 |
| cacaattaca cccatctgta caaagccacg gaaagtagct atgcgatttt gctgttcaaa | 180 |
| gcaaatccga atccgctgtt ttacggtccg tctgttctct tgttagaagt gtcgccaact | 240 |
| cccctttgaga acaccaagaa agatgagaaa tttaagcctg tgctgaaaac ctttgatctg | 300 |
| cgtgcaacag tggaagataa agaagcggaa gaattcaaaa gcaaatcctg tggtgatgag | 360 |
| aaagaggatg tcttttatcgc tggatatgcc ttcttttatg cgaactattc ctgcttttat | 420 |
| gacaaagcag ggatctactt tgaaagcctg tatttccgcg aatcataccg caaactgggc | 480 |
| atgggtggac ttctgttcgg gactgtagcg tctattgccg ccaataacgg ctttgctagt | 540 |
| gttgaaggca ttgtagccgt gtggaacaag aaaagctacg acttctacgt gaacatgggc | 600 |
| gtcgaaattt tcgacgaatt tcgctatggc aaactggtag gtgatgcact tcagaaatat | 660 |
| gcggataaag aaaaggtgta a | 681 |

<210> SEQ ID NO 14
<211> LENGTH: 738
<212> TYPE: DNA
<213> ORGANISM: Capsicum annuum
<220> FEATURE:
<223> OTHER INFORMATION: (CaTHT)

<400> SEQUENCE: 14

| | |
|---|---|
| atggcttctg ccattagcga aacgattacg actaatggtc caagcgaaaa taacaacttg | 60 |
| accattacgg gcaaaatcca cacacgtgtc cgtctggcaa ccaaaagtga tctgcaccat | 120 |
| atctaccagc tgttctatca gatccatgcg tatcacaatt tcacgcattt atacaaggct | 180 |
| accgagtcta gtctgggaga tctcctgttt aaagagaatc ctcttccgct gttttatggc | 240 |
| ccttcagtgc tcttgttgga agtgtcccca actccgttta cccaaccgaa gaacaacaaa | 300 |
| gatgagggtt tcaaacccgt gttaaccacc ttcaatctga aatttccggt tgttgaagga | 360 |
| caagtcgaag agtttcagag caaatacgac gatggcaacg ataaacgcga tgtattcatt | 420 |
| gcaggctatg cgttcttttta tgccaactat tcgtgctttt acgacaaacc gggctttttac | 480 |
| ttcgaatcgc tgtatttccg cgaaagctat cgcaaactgg gtatgggtcg gttactgttt | 540 |

```
ggcacagttg cgtcaattgc cgcaaacaat ggctttgtgt ccgtagaagg cattgttgcg    600
gtgtggaaca agaaatcgta cgacttctac atcgatatgg gtgtcgaaat ctttgacgaa    660
tttcgttatg ggaaacttca tggggaaaat ctgcagaaat atgcggataa acagaagaac    720
gagggtggga attgttaa                                                  738

<210> SEQ ID NO 15
<211> LENGTH: 1107
<212> TYPE: DNA
<213> ORGANISM: Clarkia breweri
<220> FEATURE:
<223> OTHER INFORMATION: (CbIEMT1)

<400> SEQUENCE: 15
atgggtagca ctgggaacgc agaaatccag attattccca cccattcgtc ggacgaagaa     60
gcgaacttat ttgcgatgca gttagcctcg gctgctgtgc tgcctatggc cctgaaagct    120
gcgattgaac ttgacgtact cgaaattatg gccaaaagcg taccaccgtc tggttacatt    180
tcaccagcag aaattgctgc gcaattgccg acgacgaatc ccgaagcacc agtgatgttg    240
gatcgcgtgt tgcgtctgct ggccagttat tcagtggtga cctatacccct tcgggaactg    300 ccgtctggca agtggagcg tctgtatggg ttagcccctg tctgcaagtt tctgacgaag    360
aatgaggatg gagtttccct ggctccgttt ctccttaccg ccacagacaa agtgttgctg    420
gaaccgtggt tttacctgaa agatgccatt ctggaaggtg ggattccgtt caacaaagcg    480
tatggcatga atgagttcga ttaccatggc actgatcacc gcttcaacaa agtgttcaac    540
aaaggcatgt cgagcaattc caccatcaca atgaagaaaa tcctcgaaat gtacaacggg    600
tttgaaggcc tgacgaccat tgttgacgta ggcggaggca caggtgcagt tgcgtccatg    660
attgtcgcga atacccgag catcaatgcg atcaactttg atctgccgca tgtcatccag    720
gatgcaccgg catttagcgg tgtcgaacac ttaggtggag acatgttcga tggcgttccc    780
aaaggtgatg cgatcttcat caaatggatt tgtcacgact ggtctgatga gcactgctta    840
aaactgctca agaattgcta tgccgcactt cctgatcatg gcaaagtcat tgttgcggag    900
tatatcctgc caccgagtcc tgatccgagc attgctacga agtagtgat ccatactgac    960 gcgctgatgc tggcctataa tccgggtggt aaagagcgta ccgaaaagga atttcaagcg    1020
ctggcgatgg cgtcaggctt tcgcggcttt aagttgcaa gttgtgcctt caacacctac    1080
gttatggagt tcctgaaaac cgcctaa                                        1107

<210> SEQ ID NO 16
<211> LENGTH: 1092
<212> TYPE: DNA
<213> ORGANISM: Catharanthus roseus
<220> FEATURE:
<223> OTHER INFORMATION: (CrOMT)

<400> SEQUENCE: 16
atgggttctg caaatccaga caataaaaat tcgatgacca aggaagaaga agaggcatgt     60
ttatccgcca tggctctagc tagtgcatca gtattaccta tggttctcaa atcggccatt    120
gaacttgatc ttttggaact aattaagaaa tctggacctg tgcttatgt atctccatcg    180 gaattggctg cccaattacc cactcagaac ccagatgccc tgttatgct cgatagaatc    240 ctccgcctat tggctagcta ttccgtcctt aattgtactc ttaaggatct tccagacggt    300
ggcattgaga ggctttacag tttggcaccc gtttgtaagt ttttgaccaa aaacgaagat    360
```

```
ggtgtttcta tggcggccct attgctaatg aatcaagata aggtcctcat ggaaagctgg    420
taccacttaa aagatgcagt tcttgaagga ggaattccat taacaaggc ttatggaatg     480 actgcatttg agtaccatgg caaagatcca agattcaaca aggttttaa ccaaggaatg     540 tctaatcact caacaatcat catgaagaag attctagaaa tttaccaagg attccaaggt    600
ctcaaaactg tggttgatgt tggtggtgga acagggcta cccttaatat gatcgtctcc     660
aaatatccct caattaaggg catcaacttc gatttgcccc acgttattga agatgcccca    720
tcttatccag gcgtcgacca cgttggagga gacatgtttg tcagcgtccc taaaggggat    780
gccattttca tgaagtggat tgtcacgac tggagcgacg cacactgcct gaagtttttg     840
aagaattgcc acgaagcact ccctgaaaat gggaaggtga tacttgctga atgtcttcta    900
ccagaggccc cagactcaac actttcaact caaaacactg ttcatgtcga tgttataatg    960
ttagcacata accctggtgg caaagaaagg actgaaaaag aatttgaggc attagctaag    1020
ggtgctggtt tcagaggctt catcaaagtt tgctgtgctt acaacagttg gattatggaa    1080
ttgctcaaat aa                                                        1092

<210> SEQ ID NO 17
<211> LENGTH: 1098
<212> TYPE: DNA
<213> ORGANISM: Rosa chinensis var. spontanea
<220> FEATURE:
<223> OTHER INFORMATION: (RcOMT)

<400> SEQUENCE: 17
atgggctcta cgggcgaaac ccagatgacc ccaactcagg tatccgatga agaggcaaat    60
ctgtttgcga tgcagttagc gtcagcttcg gtgcttccca tggtccttaa agctgcgatt    120
gaactggatc tgctggagat tatggcgaaa gctgggcctg gtgcgttctt gtctcctaat    180
gatctggcct cccaactgcc gactaagaat cctgaagcac cggttatgct ggatcgtatg    240 ctgcgttttgc tggccagtta cagcatcctg acctatagct tgcgcacatt accggatggc    300
aaagtggaac gtctgtatgg tttgggccca gtctgcaaat ttctgacgaa aaacgaggat    360
ggcgtgtcga ttgcggcatt ctgtctctta gctcaggaca agtgctggt cgaaagctgg     420 taccacctga agacgccgt gttggatggt gggattccgt tcaataaagc gtatggcatg     480
accatctttg actactttgg taccgatccg cgcattaaca aagtgttcaa caaaggcatg    540
gcggatcata gcactattac catgaagaaa atcctggaaa cctacaaagg ctttgaggga    600
ctgacgtcga ttgttgatgt cggaggtggt acaggggcag tggtgaacat gattgtctcc    660
aaatacccga gcatcaaagg catcaacttt gatctcccgc atgttatcga agatgcccgg    720
caatatccgg gcgttcagca cgtaggtggc gacatgttcg tgagtgtccc caaaggtgat    780
gcgattttca tgaaatggat tgccatgac tggtctgatg agcattgcct gaaattcctc     840
aagaactgtt atgccgctct tccggacaat gggaaggtta ttctgggtga atgtatcctc    900
ccagttgcgc cagacacgag tttagccacc aaaggagtag ttcacaccga cgtgcttatg    960
ctggcctata atccgggtgg caaagaacgg acagaacagg aatttgaagc gttagccaaa    1020
ggttcagggt tcaaggcat tcgcgtagca tgcaacgcat taacacgta tgtgatcgag      1080 tttctgaaga agatctaa                                                  1098

<210> SEQ ID NO 18
<211> LENGTH: 1095
<212> TYPE: DNA
<213> ORGANISM: Pinus sylvestris
```

<220> FEATURE:
<223> OTHER INFORMATION: (PsOMT)

<400> SEQUENCE: 18

| | |
|---|---|
| atgggttctg cgtctgaatc ttctgaaatg aacgcgaaaa tcgttaacga agacgaatgg | 60 |
| ctgctgggta tggaactggg taacttctct tgcgttccga tggcgatgaa agcggcgatc | 120 |
| gaactggacg ttctgcagat catcgcgaac gcgggtaacg tgttcagct gtctccgcgt | 180 |
| cagatcgttg cgcacatccc gaccaccaac ccggacgcgg cgatcaccct ggaccgtatc | 240 |
| ctgcgtgttc tggcgtctca ctctgttctg tcttgctctg ttaccaccga cgaaaacggt | 300 |
| aaagcggaac gtctgtacgg tctgaccccg ctgtgcaaat acctggttaa aaaccaggac | 360 |
| ggtgttctc tggcgccgct ggttctgatg aaccaggaca aagttctgat ggaatcttgg | 420 |
| tactacctga aagacgcggt tctggacggt tctcagccgt tcaccaaagc gcacggtatg | 480 |
| aacgcgttcg aatacccggc gatggaccag cgtttcaacc gtgttttcaa ccgtggtatg | 540 |
| gcggaacact ctaccatgct gatgaacaaa atcctggaca cctacgaagg tttcaaagaa | 600 |
| gttcaggaac tggttgacgt tggtggtggt gttggttcta ccctgaacct gatcgtttct | 660 |
| aaatacccgc acatctctgg tatcaacttc gacatgccgc acgttgttgc ggacgcgccg | 720 |
| cactacccgg cggttaaaca cgttggtggt gacatgttcg actctgttcc gtctggtcag | 780 |
| gcgatcttca tgaaatggat tttacacgac tggtctgacg accactgcct gcgtctgctg | 840 |
| aaaaactgcc acaaagcgct gccggaaaaa ggtaaagtta tcgttgttga caccatcctg | 900 |
| ccggttgcgg cggaaacctc tccgtacgcg cgtcagggtt tccacatcga cctgctgatg | 960 |
| ctggcgtaca acccgggtgg taagaacgt accgaacagg aattccgtga cctggcgaaa | 1020 |
| gaagttggtt tcgcgggtgg tgttaaaccg gtttgctgcg ttaacggtca ctgggttatg | 1080 |
| gaattccaca aatag | 1095 |

<210> SEQ ID NO 19
<211> LENGTH: 663
<212> TYPE: DNA
<213> ORGANISM: Synechocystis sp. PCC 6803
<220> FEATURE:
<223> OTHER INFORMATION: (SynOMT)

<400> SEQUENCE: 19

| | |
|---|---|
| atgggtaagg gcatcaccgg ttttgatcct agtctttatt cctatctgca aagcattagt | 60 |
| gcagatgatt cgttctatct agcacaattg cggcgggaaa cggcccattt acccggtgcc | 120 |
| cccatgcaaa ttagcccaga gcaagcccaa tttcttggtt tgttaatcag tttaaccggg | 180 |
| gcaaaacagg tactggaaat aggtgttttt cggggttata gtgccttagc catggctttg | 240 |
| caacttcctc ccgatggtca aattattgcc tgtgaccaag accccaacgc taccgcgatc | 300 |
| gccaaaaagt attggcaaaa ggctggggtg gccgaaaaaa ttagtttaag gttggggcca | 360 |
| gcactggcaa cattagagca gttgacccag gcaaaccgt tgcctgaatt tgacttaatt | 420 |
| tttattgatg ccgataaacg gaactatccc cgctattacg aaatcggctt aaatttactg | 480 |
| cggcggggag gattgatggt tattgacaat gtgctctggc atggaaaagt gacggaagtt | 540 |
| gaccccccaag aagcccaaac ccaagtttta caacaattta accgtgaccct agcccaggat | 600 |
| gaacgggtac ggatcagtgt gattcccctg ggggacggca tgactttggc actcaaaaaa | 660 |
| tag | 663 |

<210> SEQ ID NO 20

<211> LENGTH: 1071
<212> TYPE: DNA
<213> ORGANISM: Triticum aestivum
<220> FEATURE:
<223> OTHER INFORMATION: (TaOMT2)

<400> SEQUENCE: 20

```
atggggtcga tcgccgccgg cgccgacgag gatgcgtgca tgtacgctct ccagctcgtc      60
tcgtcgtcga tcctcccgat gacgctgaag aacgccatcg agctgggggct cctcgagacc    120
ctgatggccg ccggcggcaa gttcttgact cccgctgagg tggcagccaa gctcccgtcc    180
gcggcgaatc cggaagcgcc ggacatggtg gaccgtatgc tccgtctgtt ggcctcgtac    240
aacgtggtgt cgtgcaggac ggaggagggc aaggacggcc gcctctcccg gcggtacggc    300
gccgcgcccg tgtgcaagta cctcaccccc aacgaggacg cgtgtccat gtcggcgctc    360
gcgctcatga accaggacaa ggtcctcatg gagagctggt actatctcaa ggatgcggtc    420
ctcgacggtg gcatcccgtt caacaaggcg tacgggatgt cggcgttcga gtaccacggc    480
acggacccac gcttcaaccg cgtcttcaac gaggggatga agaaccattc catcatcatc    540
accaagaagc tcctcgagtc ctacaagggc ttcgagggcc tcggcaccct cgtcgacgtg    600
ggcggtggcg tcggcgccac cgtggccgcc atcaccgctc actaccccac catcaagggc    660
atcaactttg accttcccca cgtcatcagt gaggcgccgc cgttccccgg tgtcacccac    720
gtcggcggca catgttcca gaaggtgccc tcgggcgacg ccatcctcat gaagtggatc    780
ctccacgact ggagcgacga gcactgcgcg acgctgctca gaactgcta cgacgcgttg    840
ccggcgcacg gcaaggtggt gctcgtggag tgcatcctgc ctgtgaaccc ggaggcgacg    900
cctaaggcgc aggggggtgtt ccatgtcgac atgatcatgc tcgcgcacaa cccgggtggc    960
agggagaggt acgagaggga gttcgaggcc ctggccaagg cgccgggtt cgccgccatg    1020
aagactactt acatctacgc caacgcatgg gccatcgagt tcactaagta g             1071
```

<210> SEQ ID NO 21
<211> LENGTH: 475
<212> TYPE: PRT
<213> ORGANISM: Drosophila melanogaster
<220> FEATURE:
<223> OTHER INFORMATION: (DmDDC)

<400> SEQUENCE: 21

```
Met Glu Ala Pro Glu Phe Lys Asp Phe Ala Lys Thr Met Val Asp Phe
  1               5                  10                  15

Ile Ala Glu Tyr Leu Glu Asn Ile Arg Glu Arg Arg Val Leu Pro Glu
             20                  25                  30

Val Lys Pro Gly Tyr Leu Lys Pro Leu Ile Pro Asp Ala Ala Pro Glu
         35                  40                  45

Lys Pro Glu Lys Trp Gln Asp Val Met Gln Asp Ile Glu Arg Val Ile
     50                  55                  60

Met Pro Gly Val Thr His Trp His Ser Pro Lys Phe His Ala Tyr Phe
 65                  70                  75                  80

Pro Thr Ala Asn Ser Tyr Pro Ala Ile Val Ala Asp Met Leu Ser Gly
                 85                  90                  95

Ala Ile Ala Cys Ile Gly Phe Thr Trp Ile Ala Ser Pro Ala Cys Thr
            100                 105                 110

Glu Leu Glu Val Val Met Met Asp Trp Leu Gly Lys Met Leu Glu Leu
        115                 120                 125

Pro Ala Glu Phe Leu Ala Cys Ser Gly Gly Lys Gly Gly Gly Val Ile
```

```
        130                 135                 140

Gln Gly Thr Ala Ser Glu Ser Thr Leu Val Ala Leu Leu Gly Ala Lys
145                 150                 155                 160

Ala Lys Lys Leu Lys Glu Val Lys Glu Leu His Pro Glu Trp Asp Glu
                165                 170                 175

His Thr Ile Leu Gly Lys Leu Val Gly Tyr Cys Ser Asp Gln Ala His
            180                 185                 190

Ser Ser Val Glu Arg Ala Gly Leu Leu Gly Gly Val Lys Leu Arg Ser
        195                 200                 205

Val Gln Ser Glu Asn His Arg Met Arg Gly Ala Ala Leu Glu Lys Ala
    210                 215                 220

Ile Glu Gln Asp Val Ala Glu Gly Leu Ile Pro Phe Tyr Ala Val Val
225                 230                 235                 240

Thr Leu Gly Thr Thr Asn Ser Cys Ala Phe Asp Tyr Leu Asp Glu Cys
                245                 250                 255

Gly Pro Val Gly Asn Lys His Asn Leu Trp Ile His Val Asp Ala Ala
            260                 265                 270

Tyr Ala Gly Ser Ala Phe Ile Cys Pro Glu Tyr Arg His Leu Met Lys
        275                 280                 285

Gly Ile Glu Ser Ala Asp Ser Phe Asn Phe Asn Pro His Lys Trp Met
    290                 295                 300

Leu Val Asn Phe Asp Cys Ser Ala Met Trp Leu Lys Asp Pro Ser Trp
305                 310                 315                 320

Val Val Asn Ala Phe Asn Val Asp Pro Leu Tyr Leu Lys His Asp Met
                325                 330                 335

Gln Gly Ser Ala Pro Asp Tyr Arg His Trp Gln Ile Pro Leu Gly Arg
            340                 345                 350

Arg Phe Arg Ala Leu Lys Leu Trp Phe Val Leu Arg Leu Tyr Gly Val
        355                 360                 365

Glu Asn Leu Gln Ala His Ile Arg Arg His Cys Asn Phe Ala Lys Gln
    370                 375                 380

Phe Gly Asp Leu Cys Val Ala Asp Ser Arg Phe Glu Leu Ala Ala Glu
385                 390                 395                 400

Ile Asn Met Gly Leu Val Cys Phe Arg Leu Lys Gly Ser Asn Glu Arg
                405                 410                 415

Asn Glu Ala Leu Leu Lys Arg Ile Asn Gly Arg Gly His Ile His Leu
            420                 425                 430

Val Pro Ala Lys Ile Lys Asp Val Tyr Phe Leu Arg Met Ala Ile Cys
        435                 440                 445

Ser Arg Phe Thr Gln Ser Glu Asp Met Glu Tyr Ser Trp Lys Glu Val
    450                 455                 460

Ser Ala Ala Ala Asp Glu Met Glu Gln Glu Gln
465                 470                 475

<210> SEQ ID NO 22
<211> LENGTH: 537
<212> TYPE: PRT
<213> ORGANISM: Argemone mexicana
<220> FEATURE:
<223> OTHER INFORMATION: (AmDDC)

<400> SEQUENCE: 22

Met Gly Ser Leu Asn Thr Glu Asp Val Leu Glu Asn Asn Thr Ala Phe
1               5                   10                  15

Gly Val Thr Asn Pro Leu Glu Pro Glu Glu Phe Arg Lys Gln Gly His
```

```
            20                  25                  30
Met Ile Ile Asp Phe Leu Ala Asp Tyr Tyr Arg Asp Ile Glu Lys Tyr
            35                  40                  45
Pro Val Arg Ser Gln Val Glu Pro Gly Tyr Leu Arg Lys Arg Leu Pro
    50                  55                  60
Glu Thr Ala Pro Tyr Asn Pro Glu Ser Met Glu Ser Ile Leu Glu Asp
65                  70                  75                  80
Val Gln Asn Glu Ile Ile Pro Gly Ile Thr His Trp Gln Ser Pro Asn
                85                  90                  95
Tyr Phe Ala Tyr Phe Pro Ser Ser Gly Ser Ile Ala Gly Phe Leu Gly
                100                 105                 110
Glu Met Leu Ser Thr Gly Phe Asn Val Val Gly Phe Asn Trp Met Ser
            115                 120                 125
Ser Pro Ala Ala Thr Glu Leu Glu Ser Ile Val Met Asp Trp Leu Gly
        130                 135                 140
Lys Met Leu Lys Leu Pro Lys Ser Phe Leu Phe Ser Gly Asn Gly Gly
145                 150                 155                 160
Gly Val Leu Gln Gly Thr Thr Cys Glu Ala Ile Leu Cys Thr Leu Thr
                165                 170                 175
Ala Ala Arg Asp Arg Met Leu Asn Lys Ile Gly Arg Glu Asn Ile Gly
                180                 185                 190
Arg Leu Val Val Tyr Gly Ser Asp Gln Thr His Cys Ala Leu Gln Lys
            195                 200                 205
Ala Ala Gln Ile Ala Gly Ile Asn Pro Lys Asn Phe Arg Ala Val Gln
        210                 215                 220
Thr Phe Lys Ala His Ser Phe Gly Leu Ser Ala Asp Thr Leu Arg Lys
225                 230                 235                 240
Val Ile Arg Ser Asp Val Glu Ala Gly Leu Ile Pro Leu Phe Val Cys
                245                 250                 255
Pro Thr Val Gly Thr Thr Ser Ser Thr Ala Val Asp Pro Ile Gly Pro
                260                 265                 270
Ile Cys Glu Val Ala Lys Glu Tyr Glu Met Trp Val His Val Asp Ala
            275                 280                 285
Ala Tyr Ala Gly Ser Ala Cys Ile Cys Pro Glu Phe Arg His Phe Ile
        290                 295                 300
Asp Gly Val Glu Asn Ala Asp Ser Phe Ser Leu Asn Ala His Lys Trp
305                 310                 315                 320
Phe Phe Thr Thr Leu Asp Cys Cys Cys Leu Trp Val Lys Asp Pro Ser
                325                 330                 335
Ala Leu Val Lys Ala Leu Ser Thr Asn Pro Glu Tyr Leu Arg Asn Lys
            340                 345                 350
Ala Thr Glu Ser Lys Gln Val Val Asp Tyr Lys Asp Trp Gln Ile Ala
        355                 360                 365
Leu Ser Arg Arg Phe Arg Ser Met Lys Leu Trp Met Val Leu Arg Asn
    370                 375                 380
Tyr Gly Val Ala Asn Leu Arg Asn Phe Leu Arg Ser His Val Lys Met
385                 390                 395                 400
Ala Lys Gln Phe Glu Gly Leu Ile Ala Ser Asp Asn Arg Phe Glu Ile
                405                 410                 415
Cys Val Pro Arg Thr Phe Ala Met Val Cys Phe Arg Leu Leu Pro Pro
                420                 425                 430
Lys Ser Thr Arg Asp Asn Arg Val Arg Glu Glu Asp Gly Leu Phe Val
            435                 440                 445
```

```
Ser Gly Val His Asp His Glu Asn Asn Ile Asn Glu Asp Asp His Leu
    450                 455                 460

Leu Val Val Ala Asn Lys Leu Asn Gln Ile Tyr Leu Glu Lys Val Asn
465                 470                 475                 480

Ala Thr Gly Ser Leu Tyr Met Thr His Ala Val Val Gly Gly Ile Tyr
                485                 490                 495

Met Ile Arg Phe Ala Val Gly Ser Thr Leu Thr Glu Glu Arg His Ile
            500                 505                 510

Thr His Ala Trp Lys Val Leu Gln Glu His Ala Asp Thr Ile Leu Gly
        515                 520                 525

Thr Phe Asn Leu Ala Asp Phe Ser Cys
    530                 535

<210> SEQ ID NO 23
<211> LENGTH: 363
<212> TYPE: PRT
<213> ORGANISM: Arabidopsis thaliana
<220> FEATURE:
<223> OTHER INFORMATION: (AtCOMT)

<400> SEQUENCE: 23

Met Gly Ser Thr Ala Glu Thr Gln Leu Thr Pro Val Gln Val Thr Asp
1               5                   10                  15

Asp Glu Ala Ala Leu Phe Ala Met Gln Leu Ala Ser Ala Ser Val Leu
            20                  25                  30

Pro Met Ala Leu Lys Ser Ala Leu Glu Leu Asp Leu Leu Glu Ile Met
        35                  40                  45

Ala Lys Asn Gly Ser Pro Met Ser Pro Thr Glu Ile Ala Ser Lys Leu
50                  55                  60

Pro Thr Lys Asn Pro Glu Ala Pro Val Met Leu Asp Arg Ile Leu Arg
65                  70                  75                  80

Leu Leu Thr Ser Tyr Ser Val Leu Thr Cys Ser Asn Arg Lys Leu Ser
                85                  90                  95

Gly Asp Gly Val Glu Arg Ile Tyr Gly Leu Gly Pro Val Cys Lys Tyr
            100                 105                 110

Leu Thr Lys Asn Glu Asp Gly Val Ser Ile Ala Ala Leu Cys Leu Met
        115                 120                 125

Asn Gln Asp Lys Val Leu Met Glu Ser Trp Tyr His Leu Lys Asp Ala
130                 135                 140

Ile Leu Asp Gly Gly Ile Pro Phe Asn Lys Ala Tyr Gly Met Ser Ala
145                 150                 155                 160

Phe Glu Tyr His Gly Thr Asp Pro Arg Phe Asn Lys Val Phe Asn Asn
                165                 170                 175

Gly Met Ser Asn His Ser Thr Ile Thr Met Lys Lys Ile Leu Glu Thr
            180                 185                 190

Tyr Lys Gly Phe Glu Gly Leu Thr Ser Leu Val Asp Val Gly Gly Gly
        195                 200                 205

Ile Gly Ala Thr Leu Lys Met Ile Val Ser Lys Tyr Pro Asn Leu Lys
210                 215                 220

Gly Ile Asn Phe Asp Leu Pro His Val Ile Glu Asp Ala Pro Ser His
225                 230                 235                 240

Pro Gly Ile Glu His Val Gly Gly Asp Met Phe Val Ser Val Pro Lys
                245                 250                 255

Gly Asp Ala Ile Phe Met Lys Trp Ile Cys His Asp Trp Ser Asp Glu
            260                 265                 270
```

```
His Cys Val Lys Phe Leu Lys Asn Cys Tyr Glu Ser Leu Pro Glu Asp
            275                 280                 285

Gly Lys Val Ile Leu Ala Glu Cys Ile Leu Pro Glu Thr Pro Asp Ser
            290                 295                 300

Ser Leu Ser Thr Lys Gln Val His Val Asp Cys Ile Met Leu Ala
305                 310                 315                 320

His Asn Pro Gly Gly Lys Glu Arg Thr Glu Lys Glu Phe Glu Ala Leu
                    325                 330                 335

Ala Lys Ala Ser Gly Phe Lys Gly Ile Lys Val Val Cys Asp Ala Phe
                    340                 345                 350

Gly Val Asn Leu Ile Glu Leu Leu Lys Lys Leu
                    355                 360
```

<210> SEQ ID NO 24
<211> LENGTH: 237
<212> TYPE: PRT
<213> ORGANISM: Mesembryanthemum crystallinum
<220> FEATURE:
<223> OTHER INFORMATION: (McPFOMT)

<400> SEQUENCE: 24

```
Met Asp Phe Ala Val Met Lys Gln Val Lys Asn Thr Gly Leu Leu Gln
1               5                   10                  15

Ser Glu Glu Leu Cys Gln Tyr Ile Leu Arg Thr Ser Val Tyr Pro Arg
            20                  25                  30

Glu Ala Gly Phe Leu Lys Glu Leu Arg Glu Ala Asn Glu Ser His Pro
        35                  40                  45

Asp Ser Tyr Met Ser Thr Ser Pro Leu Ala Gly Gln Leu Met Ser Phe
    50                  55                  60

Val Leu Lys Leu Val Asn Ala Lys Thr Ile Glu Val Gly Val Phe
65                  70                  75                  80

Thr Gly Tyr Ser Leu Leu Leu Thr Ala Leu Ser Ile Pro Asp Asp Gly
                85                  90                  95

Lys Ile Thr Ala Ile Asp Phe Asp Arg Glu Ala Tyr Glu Ile Gly Leu
            100                 105                 110

Pro Phe Ile Arg Lys Ala Gly Val Glu His Lys Ile Asn Phe Ile Glu
        115                 120                 125

Ser Asp Ala Met Leu Ala Leu Asp Asn Leu Leu Gln Gly Gln Glu Ser
    130                 135                 140

Glu Gly Ser Tyr Asp Phe Gly Phe Val Asp Ala Asp Lys Pro Asn Tyr
145                 150                 155                 160

Ile Lys Tyr His Glu Arg Leu Met Lys Leu Val Lys Val Gly Gly Ile
                165                 170                 175

Val Ala Tyr Asp Asn Thr Leu Trp Gly Gly Thr Val Ala Gln Pro Glu
            180                 185                 190

Ser Glu Val Pro Asp Phe Met Lys Glu Asn Arg Glu Ala Val Ile Glu
        195                 200                 205

Leu Asn Lys Leu Leu Ala Ala Asp Pro Arg Ile Glu Ile Val His Leu
    210                 215                 220

Pro Leu Gly Asp Gly Ile Thr Phe Cys Arg Arg Leu Tyr
225                 230                 235
```

<210> SEQ ID NO 25
<211> LENGTH: 358
<212> TYPE: PRT
<213> ORGANISM: Glycine max
<220> FEATURE:
<223> OTHER INFORMATION: (GmSOMT)

<400> SEQUENCE: 25

Met Ala Ser Pro Leu Asn Asn Gly Arg Lys Ala Ser Glu Ile Phe Gln
1               5                   10                  15

Gly Gln Ala Leu Leu Tyr Lys His Leu Leu Gly Phe Ile Asp Ser Lys
            20                  25                  30

Cys Leu Lys Trp Met Val Glu Leu Asp Ile Pro Asp Ile Ile His Ser
        35                  40                  45

His Ser His Gly Gln Pro Ile Thr Phe Ser Glu Leu Val Ser Ile Leu
    50                  55                  60

Gln Val Pro Pro Thr Lys Thr Arg Gln Val Gln Ser Leu Met Arg Tyr
65                  70                  75                  80

Leu Ala His Asn Gly Phe Phe Glu Ile Val Arg Ile His Asp Asn Ile
                85                  90                  95

Glu Ala Tyr Ala Leu Thr Ala Ala Ser Glu Leu Leu Val Lys Ser Ser
            100                 105                 110

Glu Leu Ser Leu Ala Pro Met Val Glu Tyr Phe Leu Glu Pro Asn Cys
        115                 120                 125

Gln Gly Ala Trp Asn Gln Leu Lys Arg Trp Val His Glu Glu Asp Leu
    130                 135                 140

Thr Val Phe Gly Val Ser Leu Gly Thr Pro Phe Trp Asp Phe Ile Asn
145                 150                 155                 160

Lys Asp Pro Ala Tyr Asn Lys Ser Phe Asn Glu Ala Met Ala Cys Asp
                165                 170                 175

Ser Gln Met Leu Asn Leu Ala Phe Arg Asp Cys Asn Trp Val Phe Glu
            180                 185                 190

Gly Leu Glu Ser Ile Val Asp Val Gly Gly Gly Thr Gly Ile Thr Ala
        195                 200                 205

Lys Ile Ile Cys Glu Ala Phe Pro Lys Leu Lys Cys Met Val Leu Glu
    210                 215                 220

Arg Pro Asn Val Val Glu Asn Leu Ser Gly Ser Asn Asn Leu Thr Phe
225                 230                 235                 240

Val Gly Gly Asp Met Phe Lys Cys Ile Pro Lys Ala Asp Ala Val Leu
                245                 250                 255

Leu Lys Leu Val Leu His Asn Trp Asn Asp Asn Asp Cys Met Lys Ile
            260                 265                 270

Leu Glu Asn Cys Lys Glu Ala Ile Ser Gly Glu Ser Lys Thr Gly Lys
        275                 280                 285

Val Val Val Ile Asp Thr Val Ile Asn Glu Asn Lys Asp Glu Arg Gln
    290                 295                 300

Val Thr Glu Leu Lys Leu Leu Met Asp Val His Met Ala Cys Ile Ile
305                 310                 315                 320

Asn Gly Lys Glu Arg Lys Glu Glu Asp Trp Lys Lys Leu Phe Met Glu
                325                 330                 335

Ala Gly Phe Gln Ser Tyr Lys Ile Ser Pro Phe Thr Gly Tyr Leu Ser
            340                 345                 350

Leu Ile Glu Ile Tyr Pro
        355

<210> SEQ ID NO 26
<211> LENGTH: 220
<212> TYPE: PRT
<213> ORGANISM: Myxococcus xanthus

```
<220> FEATURE:
<223> OTHER INFORMATION: (MxSafC)

<400> SEQUENCE: 26

Met Ile His His Val Glu Leu Thr Gln Ser Val Leu Gln Tyr Ile Arg
1               5                   10                  15

Asp Ser Ser Val Arg Asp Asn Asp Ile Leu Arg Asp Leu Arg Glu Glu
                20                  25                  30

Thr Ser Lys Leu Pro Leu Arg Thr Met Gln Ile Pro Pro Glu Gln Gly
            35                  40                  45

Gln Leu Leu Ser Leu Leu Val Arg Leu Ile Gly Ala Arg Lys Thr Leu
        50                  55                  60

Glu Val Gly Val Phe Thr Gly Tyr Ser Thr Leu Cys Ala Ala Leu Ala
65                  70                  75                  80

Leu Pro Ala Asp Gly Arg Val Ile Ala Cys Asp Leu Ser Glu Glu Trp
                85                  90                  95

Val Ser Ile Ala Arg Arg Tyr Trp Gln Arg Ala Gly Val Ala Asp Arg
            100                 105                 110

Ile Glu Val Arg Leu Gly Asp Ala His His Ser Leu Glu Ala Leu Val
        115                 120                 125

Gly Ser Glu His Arg Gly Thr Phe Asp Leu Ala Phe Ile Asp Ala Asp
130                 135                 140

Lys Glu Ser Tyr Asp Phe Tyr Glu His Ala Leu Arg Leu Val Arg
145                 150                 155                 160

Pro Gly Gly Leu Ile Ile Leu Asp Asn Thr Leu Trp Ser Gly Lys Val
                165                 170                 175

Ala Asp Pro Ser Val Val Gly Asp Pro Glu Thr Asp Ser Leu Arg Arg
            180                 185                 190

Ile Asn Ala Lys Leu Leu Thr Asp Glu Arg Val Asp Leu Ser Met Leu
        195                 200                 205

Pro Ile Ala Asp Gly Leu Thr Leu Ala Arg Lys Arg
210                 215                 220

<210> SEQ ID NO 27
<211> LENGTH: 368
<212> TYPE: PRT
<213> ORGANISM: Clarkia breweri
<220> FEATURE:
<223> OTHER INFORMATION: (CbMOMT)

<400> SEQUENCE: 27

Met Gly Ser Thr Gly Asn Ala Glu Ile Gln Ile Pro Thr His Ser
1               5                   10                  15

Ser Asp Glu Glu Ala Asn Leu Phe Ala Met Gln Leu Ala Ser Ala Ala
                20                  25                  30

Val Leu Pro Met Ala Leu Lys Ala Ala Ile Glu Leu Asp Val Leu Glu
            35                  40                  45

Ile Met Ala Lys Ser Val Pro Pro Ser Gly Tyr Ile Ser Pro Ala Glu
        50                  55                  60

Ile Ala Ala Gln Leu Pro Thr Thr Asn Pro Gly Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
            100                 105                 110

Pro Val Cys Lys Phe Leu Thr Lys Asn Glu Asp Gly Val Ser Leu Ala
```

```
                    115                 120                 125
Pro Phe Leu Leu Leu Ala Thr Asp Lys Val Leu Leu Glu Pro Trp Phe
    130                 135                 140

Tyr Leu Lys Asp Ala Ile Leu Glu Gly Gly Ile Pro Phe Asn Lys Ala
145                 150                 155                 160

Tyr Gly Met Asn Ile Phe Asp Tyr Phe Gly Thr Asp His Arg Ile Asn
                165                 170                 175

Lys Val Phe Asn Lys Gly Met Ser Ser Asn Ser Thr Ile Thr Met Lys
            180                 185                 190

Lys Ile Leu Glu Met Tyr Asn Gly Phe Glu Gly Leu Thr Thr Ile Val
        195                 200                 205

Asp Val Gly Gly Gly Thr Gly Ala Val Ala Ser Met Ile Val Ala Lys
    210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
                245                 250                 255

Asp Gly Val Pro Lys Gly Asp Ala Ile Phe Ile Lys Trp Ile Cys His
            260                 265                 270

Asp Trp Ser Asp Glu His Cys Leu Lys Leu Leu Lys Asn Cys Tyr Ala
        275                 280                 285

Ala Leu Pro Asp His Gly Lys Val Ile Val Ala Glu Tyr Ile Leu Pro
    290                 295                 300

Pro Ser Pro Asp Pro Ser Ile Ala Thr Lys Val Val Ile His Thr Asp
305                 310                 315                 320

Ala Leu Met Leu Ala Tyr Asn Pro Gly Gly Lys Glu Arg Thr Glu Lys
                325                 330                 335

Glu Phe Gln Ala Leu Ala Met Ala Ser Gly Phe Arg Gly Phe Lys Val
            340                 345                 350

Ala Ser Cys Ala Phe Asn Thr Tyr Val Met Glu Phe Leu Lys Thr Ala
        355                 360                 365

<210> SEQ ID NO 28
<211> LENGTH: 368
<212> TYPE: PRT
<213> ORGANISM: Clarkia breweri
<220> FEATURE:
<223> OTHER INFORMATION: (CbMOMT-L322N)

<400> SEQUENCE: 28

Met Gly Ser Thr Gly Asn Ala Glu Ile Gln Ile Ile Pro Thr His Ser
1               5                   10                  15

Ser Asp Glu Glu Ala Asn Leu Phe Ala Met Gln Leu Ala Ser Ala Ala
            20                  25                  30

Val Leu Pro Met Ala Leu Lys Ala Ala Ile Glu Leu Asp Val Leu Glu
        35                  40                  45

Ile Met Ala Lys Ser Val Pro Pro Ser Gly Tyr Ile Ser Pro Ala Glu
    50                  55                  60

Ile Ala Ala Gln Leu Pro Thr Thr Asn Pro Glu Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
            100                 105                 110

Pro Val Cys Lys Phe Leu Thr Lys Asn Glu Asp Gly Val Ser Leu Ala
```

```
        115                 120                 125
Pro Phe Leu Leu Leu Ala Thr Asp Lys Val Leu Leu Glu Pro Trp Phe
130                 135                 140

Tyr Leu Lys Asp Ala Ile Leu Glu Gly Gly Ile Pro Phe Asn Lys Ala
145                 150                 155                 160

Tyr Gly Met Asn Ile Phe Asp Tyr Phe Thr Asp His Arg Ile Asn
                165                 170                 175

Lys Val Phe Asn Lys Gly Met Ser Ser Asn Ser Thr Ile Thr Met Lys
                180                 185                 190

Lys Ile Leu Glu Met Tyr Asn Gly Phe Glu Gly Leu Thr Thr Ile Val
                195                 200                 205

Asp Val Gly Gly Gly Thr Gly Ala Val Ala Ser Met Ile Val Ala Lys
210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
                245                 250                 255

Asp Gly Val Pro Lys Gly Asp Ala Ile Phe Ile Lys Trp Ile Cys His
                260                 265                 270

Asp Trp Ser Asp Glu His Cys Leu Lys Leu Leu Lys Asn Cys Tyr Ala
                275                 280                 285

Ala Leu Pro Asp His Gly Lys Val Ile Val Ala Glu Tyr Ile Leu Pro
290                 295                 300

Pro Ser Pro Asp Pro Ser Ile Ala Thr Lys Val Val Ile His Thr Asp
305                 310                 315                 320

Ala Asn Met Leu Ala Tyr Asn Pro Gly Gly Lys Glu Arg Thr Glu Lys
                325                 330                 335

Glu Phe Gln Ala Leu Ala Met Ala Ser Gly Phe Arg Gly Phe Lys Val
                340                 345                 350

Ala Ser Cys Ala Phe Asn Thr Tyr Val Met Glu Phe Leu Lys Thr Ala
                355                 360                 365

<210> SEQ ID NO 29
<211> LENGTH: 368
<212> TYPE: PRT
<213> ORGANISM: Clarkia breweri
<220> FEATURE:
<223> OTHER INFORMATION: (CbMOMT4-T133S)

<400> SEQUENCE: 29

Met Gly Ser Thr Gly Asn Ala Glu Ile Gln Ile Pro Thr His Ser
1               5                   10                  15

Ser Asp Glu Glu Ala Asn Leu Phe Ala Met Gln Leu Ala Ser Ala Ala
                20                  25                  30

Val Leu Pro Met Ala Leu Lys Ala Ala Ile Glu Leu Asp Val Leu Glu
                35                  40                  45

Ile Met Ala Lys Ser Val Pro Pro Ser Gly Tyr Ile Ser Pro Ala Glu
                50                  55                  60

Ile Ala Ala Gln Leu Pro Thr Thr Asn Pro Glu Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
                100                 105                 110

Pro Val Cys Lys Phe Leu Thr Lys Asn Glu Asp Gly Val Ser Leu Ala
```

```
            115                 120                 125
Pro Phe Leu Leu Ser Ala Thr Asp Lys Val Leu Leu Glu Pro Trp Phe
    130                 135                 140

Tyr Leu Lys Asp Ala Ile Leu Glu Gly Gly Ile Pro Phe Asn Lys Ala
145                 150                 155                 160

Tyr Gly Met Asn Ile Phe Asp Tyr Phe Gly Thr Asp His Arg Ile Asn
                165                 170                 175

Lys Val Phe Asn Lys Gly Met Ser Ser Asn Ser Thr Ile Thr Met Lys
            180                 185                 190

Lys Ile Leu Glu Met Tyr Asn Gly Phe Glu Gly Leu Thr Thr Ile Val
        195                 200                 205

Asp Val Gly Gly Gly Thr Gly Ala Val Ala Ser Met Ile Val Ala Lys
    210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
                245                 250                 255

Asp Gly Val Pro Lys Gly Asp Ala Ile Phe Ile Lys Trp Ile Cys His
            260                 265                 270

Asp Trp Ser Asp Glu His Cys Leu Lys Leu Leu Lys Asn Cys Tyr Ala
        275                 280                 285

Ala Leu Pro Asp His Gly Lys Val Ile Val Ala Glu Tyr Ile Leu Pro
    290                 295                 300

Pro Ser Pro Asp Pro Ser Ile Ala Thr Lys Val Val Ile His Thr Asp
305                 310                 315                 320

Ala Leu Met Leu Ala Tyr Asn Pro Gly Gly Lys Glu Arg Thr Glu Lys
                325                 330                 335

Glu Phe Gln Ala Leu Ala Met Ala Ser Gly Phe Arg Gly Phe Lys Val
            340                 345                 350

Ala Ser Cys Ala Phe Asn Thr Tyr Val Met Glu Phe Leu Lys Thr Ala
        355                 360                 365

<210> SEQ ID NO 30
<211> LENGTH: 384
<212> TYPE: PRT
<213> ORGANISM: Saccharomyces cerevisiae
<220> FEATURE:
<223> OTHER INFORMATION: (ScSAMS)

<400> SEQUENCE: 30

Met Ser Lys Ser Lys Thr Phe Leu Phe Thr Ser Glu Ser Val Gly Glu
1               5                   10                  15

Gly His Pro Asp Lys Ile Cys Asp Gln Val Ser Asp Ala Ile Leu Asp
            20                  25                  30

Ala Cys Leu Glu Gln Asp Pro Phe Ser Lys Val Ala Cys Glu Thr Ala
        35                  40                  45

Ala Lys Thr Gly Met Ile Met Val Phe Gly Glu Ile Thr Thr Lys Ala
    50                  55                  60

Arg Leu Asp Tyr Gln Gln Ile Val Arg Asp Thr Ile Lys Lys Ile Gly
65                  70                  75                  80

Tyr Asp Asp Ser Ala Lys Gly Phe Asp Tyr Lys Thr Cys Asn Val Leu
                85                  90                  95

Val Ala Ile Glu Gln Gln Ser Pro Asp Ile Ala Gln Gly Leu His Tyr
            100                 105                 110

Glu Lys Ser Leu Glu Asp Leu Gly Ala Gly Asp Gln Gly Ile Met Phe
```

```
            115                 120                 125
Gly Tyr Ala Thr Asp Glu Thr Pro Glu Gly Leu Pro Leu Thr Ile Leu
        130                 135                 140

Leu Ala His Lys Leu Asn Met Ala Met Ala Asp Ala Arg Arg Asp Gly
145                 150                 155                 160

Ser Leu Pro Trp Leu Arg Pro Asp Thr Lys Thr Gln Val Thr Val Glu
                165                 170                 175

Tyr Glu Asp Asp Asn Gly Arg Trp Val Pro Lys Arg Ile Asp Thr Val
            180                 185                 190

Val Ile Ser Ala Gln His Ala Asp Glu Ile Ser Thr Ala Asp Leu Arg
        195                 200                 205

Thr Gln Leu Gln Lys Asp Ile Val Glu Lys Val Ile Pro Lys Asp Met
210                 215                 220

Leu Asp Glu Asn Thr Lys Tyr Phe Ile Gln Pro Ser Gly Arg Phe Val
225                 230                 235                 240

Ile Gly Gly Pro Gln Gly Asp Ala Gly Leu Thr Gly Arg Lys Ile Ile
                245                 250                 255

Val Asp Ala Tyr Gly Gly Ala Ser Ser Val Gly Gly Gly Ala Phe Ser
            260                 265                 270

Gly Lys Asp Tyr Ser Lys Val Asp Arg Ser Ala Ala Tyr Ala Ala Arg
        275                 280                 285

Trp Val Ala Lys Ser Leu Val Ala Ala Gly Leu Cys Lys Arg Val Gln
290                 295                 300

Val Gln Phe Ser Tyr Ala Ile Gly Ile Ala Glu Pro Leu Ser Leu His
305                 310                 315                 320

Val Asp Thr Tyr Gly Thr Ala Thr Lys Ser Asp Asp Glu Ile Ile Glu
                325                 330                 335

Ile Ile Lys Lys Asn Phe Asp Leu Arg Pro Gly Val Leu Val Lys Glu
            340                 345                 350

Leu Asp Leu Ala Arg Pro Ile Tyr Leu Pro Thr Ala Ser Tyr Gly His
        355                 360                 365

Phe Thr Asn Gln Glu Tyr Ser Trp Glu Lys Pro Lys Lys Leu Glu Phe
370                 375                 380

<210> SEQ ID NO 31
<211> LENGTH: 556
<212> TYPE: PRT
<213> ORGANISM: Arabidopsis thaliana
<220> FEATURE:
<223> OTHER INFORMATION: (At4CL2)

<400> SEQUENCE: 31

Met Thr Thr Gln Asp Val Ile Val Asn Asp Gln Asn Asp Gln Lys Gln
1               5                   10                  15

Cys Ser Asn Asp Val Ile Phe Arg Ser Arg Leu Pro Asp Ile Tyr Ile
            20                  25                  30

Pro Asn His Leu Pro Leu His Asp Tyr Ile Phe Glu Asn Ile Ser Glu
        35                  40                  45

Phe Ala Ala Lys Pro Cys Leu Ile Asn Gly Pro Thr Gly Glu Val Tyr
    50                  55                  60

Thr Tyr Ala Asp Val His Val Thr Ser Arg Lys Leu Ala Ala Gly Leu
65                  70                  75                  80

His Asn Leu Gly Val Lys Gln His Asp Val Val Met Ile Leu Leu Pro
                85                  90                  95

Asn Ser Pro Glu Val Val Leu Thr Phe Leu Ala Ala Ser Phe Ile Gly
```

```
                    100                 105                 110
Ala Ile Thr Thr Ser Ala Asn Pro Phe Phe Thr Pro Ala Glu Ile Ser
            115                 120                 125

Lys Gln Ala Lys Ala Ser Ala Ala Lys Leu Ile Val Thr Gln Ser Arg
130                 135                 140

Tyr Val Asp Lys Ile Lys Asn Leu Gln Asn Asp Gly Val Leu Ile Val
145                 150                 155                 160

Thr Thr Asp Ser Asp Ala Ile Pro Glu Asn Cys Leu Arg Phe Ser Glu
                165                 170                 175

Leu Thr Gln Ser Glu Glu Pro Arg Val Asp Ser Ile Pro Glu Lys Ile
            180                 185                 190

Ser Pro Glu Asp Val Val Ala Leu Pro Phe Ser Ser Gly Thr Thr Gly
    195                 200                 205

Leu Pro Lys Gly Val Met Leu Thr His Lys Gly Leu Val Thr Ser Val
    210                 215                 220

Ala Gln Gln Val Asp Gly Glu Asn Pro Asn Leu Tyr Phe Asn Arg Asp
225                 230                 235                 240

Asp Val Ile Leu Cys Val Leu Pro Met Phe His Ile Tyr Ala Leu Asn
                245                 250                 255

Ser Ile Met Leu Cys Ser Leu Arg Val Gly Ala Thr Ile Leu Ile Met
            260                 265                 270

Pro Lys Phe Glu Ile Thr Leu Leu Leu Glu Gln Ile Gln Arg Cys Lys
        275                 280                 285

Val Thr Val Ala Met Val Val Pro Pro Ile Val Leu Ala Ile Ala Lys
    290                 295                 300

Ser Pro Glu Thr Glu Lys Tyr Asp Leu Ser Ser Val Arg Met Val Lys
305                 310                 315                 320

Ser Gly Ala Ala Pro Leu Gly Lys Glu Leu Glu Asp Ala Ile Ser Ala
                325                 330                 335

Lys Phe Pro Asn Ala Lys Leu Gly Gln Gly Tyr Gly Met Thr Glu Ala
            340                 345                 350

Gly Pro Val Leu Ala Met Ser Leu Gly Phe Ala Lys Glu Pro Phe Pro
        355                 360                 365

Val Lys Ser Gly Ala Cys Gly Thr Val Val Arg Asn Ala Glu Met Lys
    370                 375                 380

Ile Leu Asp Pro Asp Thr Gly Asp Ser Leu Pro Arg Asn Lys Pro Gly
385                 390                 395                 400

Glu Ile Cys Ile Arg Gly Asn Gln Ile Met Lys Gly Tyr Leu Asn Asp
                405                 410                 415

Pro Leu Ala Thr Ala Ser Thr Ile Asp Lys Asp Gly Trp Leu His Thr
            420                 425                 430

Gly Asp Val Gly Phe Ile Asp Asp Asp Glu Leu Phe Ile Val Asp
        435                 440                 445

Arg Leu Lys Glu Leu Ile Lys Tyr Lys Gly Phe Gln Val Ala Pro Ala
    450                 455                 460

Glu Leu Glu Ser Leu Leu Ile Gly His Pro Glu Ile Asn Asp Val Ala
465                 470                 475                 480

Val Val Ala Met Lys Glu Glu Asp Ala Gly Glu Val Pro Val Ala Phe
                485                 490                 495

Val Val Arg Ser Lys Asp Ser Asn Ile Ser Glu Asp Glu Ile Lys Gln
            500                 505                 510

Phe Val Ser Lys Gln Val Val Phe Tyr Lys Arg Ile Asn Lys Val Phe
        515                 520                 525
```

Phe Thr Asp Ser Ile Pro Lys Ala Pro Ser Gly Lys Ile Leu Arg Lys
            530                 535                 540

Asp Leu Arg Ala Arg Leu Ala Asn Gly Leu Met Asn
545                 550                 555

<210> SEQ ID NO 32
<211> LENGTH: 547
<212> TYPE: PRT
<213> ORGANISM: Nicotiana tabacum
<220> FEATURE:
<223> OTHER INFORMATION: (Nt4CL1)

<400> SEQUENCE: 32

Met Pro Met Glu Thr Thr Thr Glu Thr Lys Gln Ser Gly Asp Leu Ile
1               5                   10                  15

Phe Arg Ser Lys Leu Pro Asp Ile Tyr Ile Pro Lys His Leu Pro Leu
                20                  25                  30

His Ser Tyr Cys Phe Glu Asn Ile Ser Glu Phe Ser Ser Arg Pro Cys
            35                  40                  45

Leu Ile Asn Gly Ala Asn Asp Gln Ile Tyr Thr Tyr Ala Glu Val Glu
        50                  55                  60

Leu Thr Cys Arg Lys Val Ala Val Gly Leu Asn Lys Leu Gly Ile Gln
65                  70                  75                  80

Gln Lys Asp Thr Ile Met Ile Leu Leu Pro Asn Ser Pro Glu Phe Val
                85                  90                  95

Phe Ala Phe Met Gly Ala Ser Tyr Leu Gly Ala Ile Ser Thr Met Ala
            100                 105                 110

Asn Pro Leu Phe Thr Pro Ala Glu Val Val Lys Gln Ala Lys Ala Ser
        115                 120                 125

Ser Ala Lys Ile Ile Ile Thr Gln Ser Cys Phe Val Gly Lys Val Lys
130                 135                 140

Asp Tyr Ala Ser Glu Asn Asp Val Lys Val Ile Cys Ile Asp Ser Ala
145                 150                 155                 160

Pro Glu Gly Cys Leu His Phe Ser Glu Leu Thr Gln Ser Asp Glu His
                165                 170                 175

Glu Ile Pro Glu Val Lys Ile Gln Pro Asp Asp Val Val Ala Leu Pro
            180                 185                 190

Tyr Ser Ser Gly Thr Thr Gly Leu Pro Lys Gly Val Met Leu Thr His
        195                 200                 205

Lys Gly Leu Val Thr Ser Val Ala Gln Gln Val Asp Gly Glu Asn Ala
210                 215                 220

Asn Leu Tyr Met His Ser Glu Asp Val Leu Met Cys Val Leu Pro Leu
225                 230                 235                 240

Phe His Ile Tyr Ser Leu Asn Ser Ile Leu Leu Cys Gly Leu Arg Val
                245                 250                 255

Gly Ala Ala Ile Leu Ile Met Gln Lys Phe Asp Ile Ala Pro Phe Leu
            260                 265                 270

Glu Leu Ile Gln Lys Tyr Lys Val Ser Ile Gly Pro Phe Val Pro Pro
        275                 280                 285

Ile Val Leu Ala Ile Ala Lys Ser Pro Ile Val Asp Ser Tyr Asp Leu
290                 295                 300

Ser Ser Val Arg Thr Val Met Ser Gly Ala Ala Pro Leu Gly Lys Glu
305                 310                 315                 320

Leu Glu Asp Ala Val Arg Thr Lys Phe Pro Asn Ala Lys Leu Gly Gln
                325                 330                 335

Gly Tyr Gly Met Thr Glu Ala Gly Pro Val Leu Ala Met Cys Leu Ala
            340                 345                 350

Phe Ala Lys Glu Pro Phe Asp Ile Lys Ser Gly Ala Cys Gly Thr Val
            355                 360                 365

Val Arg Asn Ala Glu Met Lys Ile Val Asp Pro Asp Thr Gly Cys Ser
370                 375                 380

Leu Pro Arg Asn Gln Pro Gly Glu Ile Cys Ile Arg Gly Asp Gln Ile
385                 390                 395                 400

Met Lys Gly Tyr Leu Asn Asp Pro Glu Ala Thr Thr Arg Thr Ile Asp
                405                 410                 415

Lys Glu Gly Trp Leu His Thr Gly Asp Ile Gly Phe Ile Asp Glu Asp
            420                 425                 430

Asp Glu Leu Phe Ile Val Asp Arg Leu Lys Glu Leu Ile Lys Tyr Lys
            435                 440                 445

Gly Phe Gln Val Ala Pro Ala Glu Ile Glu Ala Leu Leu Leu Asn His
            450                 455                 460

Pro Asn Ile Ser Asp Ala Ala Val Val Pro Met Lys Asp Glu Gln Ala
465                 470                 475                 480

Gly Glu Val Pro Val Ala Phe Val Arg Ser Asn Gly Ser Ala Ile
                485                 490                 495

Thr Glu Asp Glu Val Lys Asp Phe Ile Ser Lys Gln Val Ile Phe Tyr
            500                 505                 510

Lys Arg Val Lys Arg Val Phe Phe Val Glu Thr Val Pro Lys Ser Pro
            515                 520                 525

Ser Gly Lys Ile Leu Arg Lys Asp Leu Arg Ala Arg Leu Ala Ala Gly
            530                 535                 540

Val Pro Asn
545

<210> SEQ ID NO 33
<211> LENGTH: 226
<212> TYPE: PRT
<213> ORGANISM: Nicotiana tabacum
<220> FEATURE:
<223> OTHER INFORMATION: (NtTHT)

<400> SEQUENCE: 33

Met Ala Thr Thr Asn Asn Lys Asn Leu Thr Ile Thr Glu Lys Val Tyr
1               5                   10                  15

Val Arg Val Arg Leu Ala Asn Glu Ala Asp Ile Ser His Ile Tyr Lys
            20                  25                  30

Leu Phe Tyr Gln Ile His Glu Tyr His Asn Tyr Thr His Leu Tyr Lys
        35                  40                  45

Ala Thr Glu Ser Ser Leu Cys Asp Leu Leu Phe Lys Ala Asn Pro Asn
    50                  55                  60

Pro Leu Phe Tyr Gly Pro Ser Val Leu Leu Glu Val Ser Pro Thr
65                  70                  75                  80

Pro Phe Glu Asn Thr Lys Lys Asp Glu Lys Phe Lys Pro Val Leu Lys
                85                  90                  95

Thr Phe Asp Leu Arg Ala Thr Val Glu Asp Lys Glu Ala Glu Glu Phe
            100                 105                 110

Lys Ser Lys Ser Cys Gly Asp Glu Lys Glu Asp Val Phe Ile Ala Gly
        115                 120                 125

Tyr Ala Phe Phe Tyr Ala Asn Tyr Ser Cys Phe Tyr Asp Lys Ala Gly
    130                 135                 140

```
Ile Tyr Phe Glu Ser Leu Tyr Phe Arg Glu Ser Tyr Arg Lys Leu Gly
145                 150                 155                 160

Met Gly Gly Leu Leu Phe Gly Thr Val Ala Ser Ile Ala Ala Asn Asn
                165                 170                 175

Gly Phe Ala Ser Val Glu Gly Ile Val Ala Val Trp Asn Lys Lys Ser
            180                 185                 190

Tyr Asp Phe Tyr Val Asn Met Gly Val Glu Ile Phe Asp Glu Phe Arg
        195                 200                 205

Tyr Gly Lys Leu Val Gly Asp Ala Leu Gln Lys Tyr Ala Asp Lys Glu
    210                 215                 220

Lys Val
225

<210> SEQ ID NO 34
<211> LENGTH: 245
<212> TYPE: PRT
<213> ORGANISM: Capsicum annuum
<220> FEATURE:
<223> OTHER INFORMATION: (CaTHT)

<400> SEQUENCE: 34

Met Ala Ser Ala Ile Ser Glu Thr Ile Thr Thr Asn Gly Pro Ser Glu
1               5                   10                  15

Asn Asn Asn Leu Thr Ile Thr Gly Lys Ile His Thr Arg Val Arg Leu
            20                  25                  30

Ala Thr Lys Ser Asp Leu His His Ile Tyr Gln Leu Phe Tyr Gln Ile
        35                  40                  45

His Ala Tyr His Asn Phe Thr His Leu Tyr Lys Ala Thr Glu Ser Ser
    50                  55                  60

Leu Gly Asp Leu Leu Phe Lys Glu Asn Pro Leu Pro Leu Phe Tyr Gly
65                  70                  75                  80

Pro Ser Val Leu Leu Leu Glu Val Ser Pro Thr Pro Phe Thr Gln Pro
                85                  90                  95

Lys Asn Asn Lys Asp Glu Gly Phe Lys Pro Val Leu Thr Thr Phe Asn
            100                 105                 110

Leu Lys Phe Pro Val Val Glu Gly Gln Val Glu Glu Phe Gln Ser Lys
        115                 120                 125

Tyr Asp Asp Gly Asn Asp Lys Arg Asp Val Phe Ile Ala Gly Tyr Ala
    130                 135                 140

Phe Phe Tyr Ala Asn Tyr Ser Cys Phe Tyr Asp Lys Pro Gly Phe Tyr
145                 150                 155                 160

Phe Glu Ser Leu Tyr Phe Arg Glu Ser Tyr Arg Lys Leu Gly Met Gly
                165                 170                 175

Arg Leu Leu Phe Gly Thr Val Ala Ser Ile Ala Ala Asn Asn Gly Phe
            180                 185                 190

Val Ser Val Glu Gly Ile Val Ala Val Trp Asn Lys Lys Ser Tyr Asp
        195                 200                 205

Phe Tyr Ile Asp Met Gly Val Glu Ile Phe Asp Glu Phe Arg Tyr Gly
    210                 215                 220

Lys Leu His Gly Glu Asn Leu Gln Lys Tyr Ala Asp Lys Gln Lys Asn
225                 230                 235                 240

Glu Gly Gly Asn Cys
            245

<210> SEQ ID NO 35
```

<211> LENGTH: 368
<212> TYPE: PRT
<213> ORGANISM: Clarkia breweri
<220> FEATURE:
<223> OTHER INFORMATION: (CbIEMT)

<400> SEQUENCE: 35

```
Met Gly Ser Thr Gly Asn Ala Glu Ile Gln Ile Ile Pro Thr His Ser
1               5                   10                  15

Ser Asp Glu Glu Ala Asn Leu Phe Ala Met Gln Leu Ala Ser Ala Ala
            20                  25                  30

Val Leu Pro Met Ala Leu Lys Ala Ala Ile Glu Leu Asp Val Leu Glu
        35                  40                  45

Ile Met Ala Lys Ser Val Pro Pro Ser Gly Tyr Ile Ser Pro Ala Glu
50                  55                  60

Ile Ala Ala Gln Leu Pro Thr Thr Asn Pro Glu Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
            100                 105                 110

Pro Val Cys Lys Phe Leu Thr Lys Asn Glu Asp Gly Val Ser Leu Ala
        115                 120                 125

Pro Phe Leu Leu Thr Ala Thr Asp Lys Val Leu Leu Glu Pro Trp Phe
130                 135                 140

Tyr Leu Lys Asp Ala Ile Leu Glu Gly Gly Ile Pro Phe Asn Lys Ala
145                 150                 155                 160

Tyr Gly Met Asn Glu Phe Asp Tyr His Gly Thr Asp His Arg Phe Asn
                165                 170                 175

Lys Val Phe Asn Lys Gly Met Ser Ser Asn Ser Thr Ile Thr Met Lys
            180                 185                 190

Lys Ile Leu Glu Met Tyr Asn Gly Phe Glu Gly Leu Thr Thr Ile Val
        195                 200                 205

Asp Val Gly Gly Gly Thr Gly Ala Val Ala Ser Met Ile Val Ala Lys
210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
                245                 250                 255

Asp Gly Val Pro Lys Gly Asp Ala Ile Phe Ile Lys Trp Ile Cys His
            260                 265                 270

Asp Trp Ser Asp Glu His Cys Leu Lys Leu Leu Lys Asn Cys Tyr Ala
        275                 280                 285

Ala Leu Pro Asp His Gly Lys Val Ile Val Ala Glu Tyr Ile Leu Pro
290                 295                 300

Pro Ser Pro Asp Pro Ser Ile Ala Thr Lys Val Val Ile His Thr Asp
305                 310                 315                 320

Ala Leu Met Leu Ala Tyr Asn Pro Gly Gly Lys Glu Arg Thr Glu Lys
                325                 330                 335

Glu Phe Gln Ala Leu Ala Met Ala Ser Gly Phe Arg Gly Phe Lys Val
            340                 345                 350

Ala Ser Cys Ala Phe Asn Thr Tyr Val Met Glu Phe Leu Lys Thr Ala
        355                 360                 365
```

<210> SEQ ID NO 36

<211> LENGTH: 363
<212> TYPE: PRT
<213> ORGANISM: Catharanthus roseus
<220> FEATURE:
<223> OTHER INFORMATION: (CrOMT)

<400> SEQUENCE: 36

Met Gly Ser Ala Asn Pro Asp Asn Lys Asn Ser Met Thr Lys Glu Glu
1               5                   10                  15

Glu Glu Ala Cys Leu Ser Ala Met Ala Leu Ala Ser Ser Val Leu
            20                  25                  30

Pro Met Val Leu Lys Ser Ala Ile Glu Leu Asp Leu Leu Glu Leu Ile
            35                  40                  45

Lys Lys Ser Gly Pro Gly Ala Tyr Val Ser Pro Ser Glu Leu Ala Ala
50                  55                  60

Gln Leu Pro Thr Gln Asn Pro Asp Ala Pro Val Met Leu Asp Arg Ile
65                  70                  75                  80

Leu Arg Leu Leu Ala Ser Tyr Ser Val Leu Asn Cys Thr Leu Lys Asp
                85                  90                  95

Leu Pro Asp Gly Gly Ile Glu Arg Leu Tyr Ser Leu Ala Pro Val Cys
            100                 105                 110

Lys Phe Leu Thr Lys Asn Glu Asp Gly Val Ser Met Ala Ala Leu Leu
            115                 120                 125

Leu Met Asn Gln Asp Lys Val Leu Met Glu Ser Trp Tyr His Leu Lys
130                 135                 140

Asp Ala Val Leu Glu Gly Gly Ile Pro Phe Asn Lys Ala Tyr Gly Met
145                 150                 155                 160

Thr Ala Phe Glu Tyr His Gly Lys Asp Pro Arg Phe Asn Lys Val Phe
                165                 170                 175

Asn Gln Gly Met Ser Asn His Ser Thr Ile Ile Met Lys Lys Ile Leu
            180                 185                 190

Glu Ile Tyr Gln Gly Phe Gln Gly Leu Lys Thr Val Val Asp Val Gly
            195                 200                 205

Gly Gly Thr Gly Ala Thr Leu Asn Met Ile Val Ser Lys Tyr Pro Ser
210                 215                 220

Ile Lys Gly Ile Asn Phe Asp Leu Pro His Val Ile Glu Asp Ala Pro
225                 230                 235                 240

Ser Tyr Pro Gly Val Asp His Val Gly Gly Asp Met Phe Val Ser Val
                245                 250                 255

Pro Lys Gly Asp Ala Ile Phe Met Lys Trp Ile Cys His Asp Trp Ser
            260                 265                 270

Asp Ala His Cys Leu Lys Phe Leu Lys Asn Cys His Glu Ala Leu Pro
            275                 280                 285

Glu Asn Gly Lys Val Ile Leu Ala Glu Cys Leu Leu Pro Glu Ala Pro
290                 295                 300

Asp Ser Thr Leu Ser Thr Gln Asn Thr Val His Val Asp Val Ile Met
305                 310                 315                 320

Leu Ala His Asn Pro Gly Gly Lys Glu Arg Thr Glu Lys Glu Phe Glu
                325                 330                 335

Ala Leu Ala Lys Gly Ala Gly Phe Arg Gly Phe Ile Lys Val Cys Cys
            340                 345                 350

Ala Tyr Asn Ser Trp Ile Met Glu Leu Leu Lys
            355                 360

<210> SEQ ID NO 37

```
<211> LENGTH: 365
<212> TYPE: PRT
<213> ORGANISM: Rosea chinensis var. spontanea
<220> FEATURE:
<223> OTHER INFORMATION: (RcOMT)

<400> SEQUENCE: 37
```

Met Gly Ser Thr Gly Glu Thr Gln Met Thr Pro Thr Gln Val Ser Asp
1               5                   10                  15

Glu Glu Ala Asn Leu Phe Ala Met Gln Leu Ala Ser Ala Ser Val Leu
            20                  25                  30

Pro Met Val Leu Lys Ala Ala Ile Glu Leu Asp Leu Leu Glu Ile Met
        35                  40                  45

Ala Lys Ala Gly Pro Gly Ala Phe Leu Ser Pro Asn Asp Leu Ala Ser
50                  55                  60

Gln Leu Pro Thr Lys Asn Pro Glu Ala Pro Val Met Leu Asp Arg Met
65                  70                  75                  80

Leu Arg Leu Leu Ala Ser Tyr Ser Ile Leu Thr Tyr Ser Leu Arg Thr
                85                  90                  95

Leu Pro Asp Gly Lys Val Glu Arg Leu Tyr Gly Leu Gly Pro Val Cys
            100                 105                 110

Lys Phe Leu Thr Lys Asn Glu Asp Gly Val Ser Ile Ala Ala Phe Cys
        115                 120                 125

Leu Leu Ala Gln Asp Lys Val Leu Val Glu Ser Trp Tyr His Leu Lys
130                 135                 140

Asp Ala Val Leu Asp Gly Gly Ile Pro Phe Asn Lys Ala Tyr Gly Met
145                 150                 155                 160

Thr Ile Phe Asp Tyr Phe Gly Thr Asp Pro Arg Ile Asn Lys Val Phe
                165                 170                 175

Asn Lys Gly Met Ala Asp His Ser Thr Ile Thr Met Lys Lys Ile Leu
            180                 185                 190

Glu Thr Tyr Lys Gly Phe Glu Gly Leu Thr Ser Ile Val Asp Val Gly
        195                 200                 205

Gly Gly Thr Gly Ala Val Val Asn Met Ile Val Ser Lys Tyr Pro Ser
210                 215                 220

Ile Lys Gly Ile Asn Phe Asp Leu Pro His Val Ile Glu Asp Ala Pro
225                 230                 235                 240

Gln Tyr Pro Gly Val Gln His Val Gly Gly Asp Met Phe Val Ser Val
                245                 250                 255

Pro Lys Gly Asp Ala Ile Phe Met Lys Trp Ile Cys His Asp Trp Ser
            260                 265                 270

Asp Glu His Cys Leu Lys Phe Leu Lys Asn Cys Tyr Ala Ala Leu Pro
        275                 280                 285

Asp Asn Gly Lys Val Ile Leu Gly Glu Cys Ile Leu Pro Val Ala Pro
290                 295                 300

Asp Thr Ser Leu Ala Thr Lys Gly Val Val His Thr Asp Val Leu Met
305                 310                 315                 320

Leu Ala Tyr Asn Pro Gly Gly Lys Glu Arg Thr Glu Gln Glu Phe Glu
                325                 330                 335

Ala Leu Ala Lys Gly Ser Gly Phe Gln Gly Ile Arg Val Ala Cys Asn
            340                 345                 350

Ala Phe Asn Thr Tyr Val Ile Glu Phe Leu Lys Lys Ile
        355                 360                 365

```
<210> SEQ ID NO 38
```

```
<211> LENGTH: 364
<212> TYPE: PRT
<213> ORGANISM: Pinus sylvestris
<220> FEATURE:
<223> OTHER INFORMATION: (PsOMT)

<400> SEQUENCE: 38
```

Met Gly Ser Ala Ser Glu Ser Glu Met Asn Ala Lys Ile Val Asn
1               5                   10                  15

Glu Asp Glu Trp Leu Leu Gly Met Glu Leu Gly Asn Phe Ser Cys Val
            20                  25                  30

Pro Met Ala Met Lys Ala Ala Ile Glu Leu Asp Val Leu Gln Ile Ile
                35                  40                  45

Ala Asn Ala Gly Asn Gly Val Gln Leu Ser Pro Arg Gln Ile Val Ala
50                  55                  60

His Ile Pro Thr Thr Asn Pro Asp Ala Ala Ile Thr Leu Asp Arg Ile
65                  70                  75                  80

Leu Arg Val Leu Ala Ser His Ser Val Leu Ser Cys Ser Val Thr Thr
                85                  90                  95

Asp Glu Asn Gly Lys Ala Glu Arg Leu Tyr Gly Leu Thr Pro Leu Cys
                100                 105                 110

Lys Tyr Leu Val Lys Asn Gln Asp Gly Val Ser Leu Ala Pro Leu Val
            115                 120                 125

Leu Met Asn Gln Asp Lys Val Leu Met Glu Ser Trp Tyr Tyr Leu Lys
130                 135                 140

Asp Ala Val Leu Asp Gly Ser Gln Pro Phe Thr Lys Ala His Gly Met
145                 150                 155                 160

Asn Ala Phe Glu Tyr Pro Ala Met Asp Gln Arg Phe Asn Arg Val Phe
                165                 170                 175

Asn Arg Gly Met Ala Glu His Ser Thr Met Leu Met Asn Lys Ile Leu
            180                 185                 190

Asp Thr Tyr Glu Gly Phe Lys Glu Val Gln Glu Leu Val Asp Val Gly
            195                 200                 205

Gly Gly Val Gly Ser Thr Leu Asn Leu Ile Val Ser Lys Tyr Pro His
210                 215                 220

Ile Ser Gly Ile Asn Phe Asp Met Pro His Val Val Ala Asp Ala Pro
225                 230                 235                 240

His Tyr Pro Ala Val Lys His Val Gly Gly Asp Met Phe Asp Ser Val
                245                 250                 255

Pro Ser Gly Gln Ala Ile Phe Met Lys Trp Ile Leu His Asp Trp Ser
            260                 265                 270

Asp Asp His Cys Leu Arg Leu Leu Lys Asn Cys His Lys Ala Leu Pro
            275                 280                 285

Glu Lys Gly Lys Val Ile Val Val Asp Thr Ile Leu Pro Val Ala Ala
290                 295                 300

Glu Thr Ser Pro Tyr Ala Arg Gln Gly Phe His Ile Asp Leu Leu Met
305                 310                 315                 320

Leu Ala Tyr Asn Pro Gly Gly Lys Glu Arg Thr Glu Gln Glu Phe Arg
                325                 330                 335

Asp Leu Ala Lys Glu Val Gly Phe Ala Gly Val Lys Pro Val Cys
            340                 345                 350

Cys Val Asn Gly His Trp Val Met Glu Phe His Lys
            355                 360

```
<210> SEQ ID NO 39
```

```
<211> LENGTH: 220
<212> TYPE: PRT
<213> ORGANISM: Synechocystis sp. PCC 6830
<220> FEATURE:
<223> OTHER INFORMATION: (SynOMT)

<400> SEQUENCE: 39

Met Gly Lys Gly Ile Thr Gly Phe Asp Pro Ser Leu Tyr Ser Tyr Leu
1               5                   10                  15

Gln Ser Ile Ser Ala Asp Asp Ser Phe Tyr Leu Ala Gln Leu Arg Arg
            20                  25                  30

Glu Thr Ala His Leu Pro Gly Ala Pro Met Gln Ile Ser Pro Glu Gln
        35                  40                  45

Ala Gln Phe Leu Gly Leu Leu Ile Ser Leu Thr Gly Ala Lys Gln Val
    50                  55                  60

Leu Glu Ile Gly Val Phe Arg Gly Tyr Ser Ala Leu Ala Met Ala Leu
65                  70                  75                  80

Gln Leu Pro Pro Asp Gly Gln Ile Ile Ala Cys Asp Gln Asp Pro Asn
                85                  90                  95

Ala Thr Ala Ile Ala Lys Lys Tyr Trp Gln Lys Ala Gly Val Ala Glu
            100                 105                 110

Lys Ile Ser Leu Arg Leu Gly Pro Ala Leu Ala Thr Leu Glu Gln Leu
        115                 120                 125

Thr Gln Gly Lys Pro Leu Pro Glu Phe Asp Leu Ile Phe Ile Asp Ala
    130                 135                 140

Asp Lys Arg Asn Tyr Pro Arg Tyr Tyr Glu Ile Gly Leu Asn Leu Leu
145                 150                 155                 160

Arg Arg Gly Gly Leu Met Val Ile Asp Asn Val Leu Trp His Gly Lys
                165                 170                 175

Val Thr Glu Val Asp Pro Gln Glu Ala Gln Thr Gln Val Leu Gln Gln
            180                 185                 190

Phe Asn Arg Asp Leu Ala Gln Asp Glu Arg Val Arg Ile Ser Val Ile
        195                 200                 205

Pro Leu Gly Asp Gly Met Thr Leu Ala Leu Lys Lys
    210                 215                 220

<210> SEQ ID NO 40
<211> LENGTH: 356
<212> TYPE: PRT
<213> ORGANISM: Triticum aestivum
<220> FEATURE:
<223> OTHER INFORMATION: (TaOMT2)

<400> SEQUENCE: 40

Met Gly Ser Ile Ala Ala Gly Ala Asp Glu Asp Ala Cys Met Tyr Ala
1               5                   10                  15

Leu Gln Leu Val Ser Ser Ser Ile Leu Pro Met Thr Leu Lys Asn Ala
            20                  25                  30

Ile Glu Leu Gly Leu Leu Glu Thr Leu Met Ala Ala Gly Gly Lys Phe
        35                  40                  45

Leu Thr Pro Ala Glu Val Ala Ala Lys Leu Pro Ser Ala Ala Asn Pro
    50                  55                  60

Glu Ala Pro Asp Met Val Asp Arg Met Leu Arg Leu Leu Ala Ser Tyr
65                  70                  75                  80

Asn Val Val Ser Cys Arg Thr Glu Glu Gly Lys Asp Gly Arg Leu Ser
                85                  90                  95

Arg Arg Tyr Gly Ala Ala Pro Val Cys Lys Tyr Leu Thr Pro Asn Glu
```

```
            100                 105                 110
Asp Gly Val Ser Met Ser Ala Leu Ala Leu Met Asn Gln Asp Lys Val
        115                 120                 125
Leu Met Glu Ser Trp Tyr Tyr Leu Lys Asp Ala Val Leu Asp Gly Gly
    130                 135                 140
Ile Pro Phe Asn Lys Ala Tyr Gly Met Ser Ala Phe Glu Tyr His Gly
145                 150                 155                 160
Thr Asp Pro Arg Phe Asn Arg Val Phe Asn Glu Gly Met Lys Asn His
                165                 170                 175
Ser Ile Ile Ile Thr Lys Lys Leu Leu Glu Ser Tyr Lys Gly Phe Glu
            180                 185                 190
Gly Leu Gly Thr Leu Val Asp Val Gly Gly Val Gly Ala Thr Val
        195                 200                 205
Ala Ala Ile Thr Ala His Tyr Pro Thr Ile Lys Gly Ile Asn Phe Asp
    210                 215                 220
Leu Pro His Val Ile Ser Glu Ala Pro Pro Phe Pro Gly Val Thr His
225                 230                 235                 240
Val Gly Gly Asp Met Phe Gln Lys Val Pro Ser Gly Asp Ala Ile Leu
                245                 250                 255
Met Lys Trp Ile Leu His Asp Trp Ser Asp Glu His Cys Ala Thr Leu
            260                 265                 270
Leu Lys Asn Cys Tyr Asp Ala Leu Pro Ala His Gly Lys Val Val Leu
        275                 280                 285
Val Glu Cys Ile Leu Pro Val Asn Pro Glu Ala Thr Pro Lys Ala Gln
    290                 295                 300
Gly Val Phe His Val Asp Met Ile Met Leu Ala His Asn Pro Gly Gly
305                 310                 315                 320
Arg Glu Arg Tyr Glu Arg Glu Phe Glu Ala Leu Ala Lys Gly Ala Gly
                325                 330                 335
Phe Ala Ala Met Lys Thr Thr Tyr Ile Tyr Ala Asn Ala Trp Ala Ile
            340                 345                 350
Glu Phe Thr Lys
        355

<210> SEQ ID NO 41
<211> LENGTH: 40
<212> TYPE: DNA
<213> ORGANISM: Artificial Sequence
<220> FEATURE:
<223> OTHER INFORMATION: Artificial DNA primer sequence
      (MOMT4-L322N_for)

<400> SEQUENCE: 41
gtcatccata ccgacgctaa catgctcgcc tataaccctg                           40

<210> SEQ ID NO 42
<211> LENGTH: 40
<212> TYPE: DNA
<213> ORGANISM: Artificial sequence
<220> FEATURE:
<223> OTHER INFORMATION: Artificial DNA primer sequence
      (MOMT4-L322N_rev)

<400> SEQUENCE: 42
cagggttata ggcgagcatg ttagcgtcgg tatggatgac                           40

<210> SEQ ID NO 43
<211> LENGTH: 39
```

<212> TYPE: DNA
<213> ORGANISM: Artificial sequence
<220> FEATURE:
<223> OTHER INFORMATION: Artificial DNA primer sequence
      (MOMT4_T133S_for)

<400> SEQUENCE: 43
ctcgcaccct ttctgctctc ggcgacggat aaagtcctg                              39

<210> SEQ ID NO 44
<211> LENGTH: 39
<212> TYPE: DNA
<213> ORGANISM: Artificial sequence
<220> FEATURE:
<223> OTHER INFORMATION: Artificial DNA primer sequence
      (MOMT4_T133S_rev)

<400> SEQUENCE: 44
caggacttta tccgtcgccg agagcagaaa gggtgcgag                              39

<210> SEQ ID NO 45
<211> LENGTH: 35
<212> TYPE: DNA
<213> ORGANISM: Artificial sequence
<220> FEATURE:
<223> OTHER INFORMATION: Artificial DNA primer sequence (pD1214_MOMT-F)

<400> SEQUENCE: 45
gcgcggtctc acgtcttatg ggttcgacag gcaat                                  35

<210> SEQ ID NO 46
<211> LENGTH: 36
<212> TYPE: DNA
<213> ORGANISM: Artificial sequence
<220> FEATURE:
<223> OTHER INFORMATION: Artificial DNA primer sequence (pD1214_MOMT-R)

<400> SEQUENCE: 46
cgcgcggtct cttgtcactt aggccgtttt caggaa                                 36

<210> SEQ ID NO 47
<211> LENGTH: 27
<212> TYPE: DNA
<213> ORGANISM: Artificial sequence
<220> FEATURE:
<223> OTHER INFORMATION: Artificial DNA primer sequence
      (pD1214_MOMT-ScSAMS-F)

<400> SEQUENCE: 47
gcgcggatcc atgtccaaga gcaaaac                                           27

<210> SEQ ID NO 48
<211> LENGTH: 31
<212> TYPE: DNA
<213> ORGANISM: Artificial sequence
<220> FEATURE:
<223> OTHER INFORMATION: Artificial DNA primer sequence
      (pD1214_MOMT-ScSAMS-R)

<400> SEQUENCE: 48
gcgcagatct ttaaaattcc aatttctttg g                                      31

<210> SEQ ID NO 49
<211> LENGTH: 38
<212> TYPE: DNA
<213> ORGANISM: Artificial sequence
<220> FEATURE:

<223> OTHER INFORMATION: Artificial DNA primer sequence (M_term-F
      (GG_MPS/MSP_P1))

<400> SEQUENCE: 49
gcgcggtctc acgtcttatg ggttcgacag gcaatgcg                          38

<210> SEQ ID NO 50
<211> LENGTH: 39
<212> TYPE: DNA
<213> ORGANISM: Artificial sequence
<220> FEATURE:
<223> OTHER INFORMATION: Artificial DNA primer sequence (M_term-R
      (SMP_jedeKombi_P2))

<400> SEQUENCE: 50
cgcgcggtct ctcaatacca aaaaacccct caagacccg                         39

<210> SEQ ID NO 51
<211> LENGTH: 36
<212> TYPE: DNA
<213> ORGANISM: Artificial sequence
<220> FEATURE:
<223> OTHER INFORMATION: Artificial DNA primer sequence (S_prom-F
      (SMP_jedeKombi_P3))

<400> SEQUENCE: 51
gcgcggtctc aattgtaata cgactcacta tagggg                            36

<210> SEQ ID NO 52
<211> LENGTH: 39
<212> TYPE: DNA
<213> ORGANISM: Artificial sequence
<220> FEATURE:
<223> OTHER INFORMATION: Artificial DNA primer sequence (S_prom-R
      (GG_PMS/MPS_P4))

<400> SEQUENCE: 52
cgcgcggtct cttgtcactt actcgcccag agcctcttt                         39

<210> SEQ ID NO 53
<211> LENGTH: 60
<212> TYPE: DNA
<213> ORGANISM: Artificial sequence
<220> FEATURE:
<223> OTHER INFORMATION: Artificial DNA sequence (BsaI-Kassette)

<400> SEQUENCE: 53
gcgcggatcc cgtcagagac ccagcagcga tcgacagcag gtctcagaca aagcttgcgc   60

<210> SEQ ID NO 54
<211> LENGTH: 31
<212> TYPE: DNA
<213> ORGANISM: Artificial sequence
<220> FEATURE:
<223> OTHER INFORMATION: Artificial DNA primer sequence
      (pET28PromSphI-F)

<400> SEQUENCE: 54
gcgcgcatgc taatacgact cactataggg g                                 31

<210> SEQ ID NO 55
<211> LENGTH: 30
<212> TYPE: DNA
<213> ORGANISM: Artificial sequence
<220> FEATURE:
<223> OTHER INFORMATION: Artificial DNA primer sequence
      (pET28TermBglII-R)

<400> SEQUENCE: 55
gcgcagatct caaaaaaccc ctcaagaccc                                       30

<210> SEQ ID NO 56
<211> LENGTH: 12
<212> TYPE: DNA
<213> ORGANISM: Artificial sequence
<220> FEATURE:
<223> OTHER INFORMATION: Artificial DNA primer sequence (RBS1)

<400> SEQUENCE: 56
aggaggtttg ga                                                          12

<210> SEQ ID NO 57
<211> LENGTH: 16
<212> TYPE: DNA
<213> ORGANISM: Artificial sequence
<220> FEATURE:
<223> OTHER INFORMATION: Artificial DNA primer sequence (RBS2)

<400> SEQUENCE: 57
aagttaagag gcaaga                                                      16

<210> SEQ ID NO 58
<211> LENGTH: 18
<212> TYPE: DNA
<213> ORGANISM: Artificial sequence
<220> FEATURE:
<223> OTHER INFORMATION: Artificial DNA primer sequence (RBS3)

<400> SEQUENCE: 58
taagcaggac cggcggcg                                                    18

<210> SEQ ID NO 59
<211> LENGTH: 1638
<212> TYPE: DNA
<213> ORGANISM: Populus trichocarpa
<220> FEATURE:
<223> OTHER INFORMATION: (PtTyDC)

<400> SEQUENCE: 59

| | | |
|---|---|---|
| atggattcag agcaactgag agagaatgca cataaaatgg tcgactttat tgctgattat | 60 |
| tacaaatcca ttgagaattt ccctgttctc agccaagttg agcctggata tctacgcgaa | 120 |
| cttctgccag attctgctcc aaatcaacct gaaacgttgc aaaatgttct tgatgatgtt | 180 |
| caagcaaaga ttttaccggg ggtgacccat tggcaaagcc cgagttattt tgcttattat | 240 |
| ccttctaaca gtagtgttgc tggattttg ggagaaatgc ttagtgctgg tattaatatg | 300 |
| gtgggtttta gctggataac atctcctgct gcaactgagc ttgaaatgat tgttctagat | 360 |
| tggcttggta aattgctcaa gctacctgaa gactttctct ctactggaca aggtggtgga | 420 |
| gtgatacagg gcactgcaag tgaagctgtt ctagttgtgc ttctggctgc tcgtgatagg | 480 |
| gtcttgagga agcttggaaa aaatgcccct tgaaaagcttg ttgtttatgc atccgatcaa | 540 |
| acacactctg ctttgcaaaa agcctgccag ataggaggga tccatccaga aaattgcaag | 600 |
| ctgctaaaaa caggctcttc aacaaattat gcccttcctc cagattact tggtaaagca | 660 |
| atttcagatg acatttccac tggattggtc cctttcttct tatgtgctac agtaggcacc | 720 |
| acatcatcaa cagctgttga cccttttgctt tctctaggaa agattgctaa gaataatgga | 780 |
| atatggtttc atgtggatgc tgcatatgct ggaagtgctt gtatttgtcc agaatatcgt | 840 |

```
tgttacattg atggtgttga agaagctgac tctttcaaca tgaatgctca taaatggttt    900
ctgacaaact ttgattgttc ggctctttgg gtaaaggata gaaatgcttt aatccagtcc    960
ctctctacga atcccgagtt cctgaagaac aaagcctctc aagcaaacat ggttgtggac   1020
tacaaagatt ggcaaattcc tcttggacgt cggtttagat cactgaaact gtggatggta   1080
ctgcggttat atggtttgga aaatctacag tgctacatca gaaatcatat caacttggct   1140
aaatattttg aagggcttgt tgctgcagat tcaagatttg aggttgtcac ccctcggata   1200
ttttcattgg tttgttttcg ccttctacct cctaacaaca atgaagatca cggaaacaat   1260
ctgaaccatg acctattaga tgctgtaaac tcaacaggga aaattttcat atcacataca   1320
gttctatcag gcaagtacat attacgtttt gctgtgggag caccattgac tgaagagagg   1380
catgttactg cagcatggaa ggttttgcaa gatgaggcct ctgctttatt aggaagtcta   1440
tagggttagt taatcctttt agtgcaatct acccgtggtt gatgaaattg actcaccaca   1500
cttcattttc cccctttcct tttgatgtat ttgattttgt tattggcatg aacacaagag   1560
gccctcatgc catacataca ttcatgcccc gcaaatgaaa tttattaaat gaaactttag   1620
tattttcaat atttcaac                                                 1638
```

<210> SEQ ID NO 60
<211> LENGTH: 480
<212> TYPE: PRT
<213> ORGANISM: Populus trichocarpa
<220> FEATURE:
<223> OTHER INFORMATION: (PtTyDC)

<400> SEQUENCE: 60

```
Met Asp Ser Glu Gln Leu Arg Glu Asn Ala His Lys Met Val Asp Phe
1               5                   10                  15

Ile Ala Asp Tyr Tyr Lys Ser Ile Glu Asn Phe Pro Val Leu Ser Gln
            20                  25                  30

Val Glu Pro Gly Tyr Leu Arg Glu Leu Pro Asp Ser Ala Pro Asn
        35                  40                  45

Gln Pro Glu Thr Leu Gln Asn Val Leu Asp Asp Val Gln Ala Lys Ile
    50                  55                  60

Leu Pro Gly Val Thr His Trp Gln Ser Pro Ser Tyr Phe Ala Tyr Tyr
65                  70                  75                  80

Pro Ser Asn Ser Ser Val Ala Gly Phe Leu Gly Glu Met Leu Ser Ala
                85                  90                  95

Gly Ile Asn Met Val Gly Phe Ser Trp Ile Thr Ser Pro Ala Ala Thr
            100                 105                 110

Glu Leu Glu Met Ile Val Leu Asp Trp Leu Gly Lys Leu Leu Lys Leu
        115                 120                 125

Pro Glu Asp Phe Leu Ser Thr Gly Gln Gly Gly Gly Val Ile Gln Gly
    130                 135                 140

Thr Ala Ser Glu Ala Val Leu Val Val Leu Ala Ala Arg Asp Arg
145                 150                 155                 160

Val Leu Arg Lys Leu Gly Lys Asn Ala Leu Glu Lys Leu Val Val Tyr
                165                 170                 175

Ala Ser Asp Gln Thr His Ser Ala Leu Gln Lys Ala Cys Gln Ile Gly
            180                 185                 190

Gly Ile His Pro Glu Asn Cys Lys Leu Leu Lys Thr Gly Ser Ser Thr
        195                 200                 205

Asn Tyr Ala Leu Ser Pro Asp Leu Leu Gly Lys Ala Ile Ser Asp Asp
    210                 215                 220
```

Ile Ser Thr Gly Leu Val Pro Phe Phe Leu Cys Ala Thr Val Gly Thr
225                 230                 235                 240

Thr Ser Ser Thr Ala Val Asp Pro Leu Leu Ser Leu Gly Lys Ile Ala
            245                 250                 255

Lys Asn Asn Gly Ile Trp Phe His Val Asp Ala Ala Tyr Ala Gly Ser
                260                 265                 270

Ala Cys Ile Cys Pro Glu Tyr Arg Cys Tyr Ile Asp Gly Val Glu Glu
            275                 280                 285

Ala Asp Ser Phe Asn Met Asn Ala His Lys Trp Phe Leu Thr Asn Phe
        290                 295                 300

Asp Cys Ser Ala Leu Trp Val Lys Asp Arg Asn Ala Leu Ile Gln Ser
305                 310                 315                 320

Leu Ser Thr Asn Pro Glu Phe Leu Lys Asn Lys Ala Ser Gln Ala Asn
                325                 330                 335

Met Val Val Asp Tyr Lys Asp Trp Gln Ile Pro Leu Gly Arg Arg Phe
            340                 345                 350

Arg Ser Leu Lys Leu Trp Met Val Leu Arg Leu Tyr Gly Leu Glu Asn
        355                 360                 365

Leu Gln Cys Tyr Ile Arg Asn His Ile Asn Leu Ala Lys Tyr Phe Glu
    370                 375                 380

Gly Leu Val Ala Ala Asp Ser Arg Phe Glu Val Val Thr Pro Arg Ile
385                 390                 395                 400

Phe Ser Leu Val Cys Phe Arg Leu Leu Pro Pro Asn Asn Glu Asp
                405                 410                 415

His Gly Asn Asn Leu Asn His Asp Leu Leu Asp Ala Val Asn Ser Thr
            420                 425                 430

Gly Lys Ile Phe Ile Ser His Thr Val Leu Ser Gly Lys Tyr Ile Leu
        435                 440                 445

Arg Phe Ala Val Gly Ala Pro Leu Thr Glu Glu Arg His Val Thr Ala
    450                 455                 460

Ala Trp Lys Val Leu Gln Asp Glu Ala Ser Ala Leu Leu Gly Ser Leu
465                 470                 475                 480

<210> SEQ ID NO 61
<211> LENGTH: 2209
<212> TYPE: DNA
<213> ORGANISM: Sorangium cellulosum
<220> FEATURE:
<223> OTHER INFORMATION: (ScDDC)

<400> SEQUENCE: 61
gatatcggac tgggcgaggc gagccgcacg atcactcggt agactcttca tcagcgtgct      60
cctgcttctg ttctgcggct ctgcatggtg tcttcgggtg gcttgtcag ctcgacgcgc      120
ccatgcagcg gcgcagccct agcggccgca ggtctgtcca cacttctttg atgaaagcga      180
gacattcggt tttcgtgccc tgtttgcccg cagccctcca gccccaggt acgggcttgt      240
cggcgggcca gatcgagtac tgctcttcgc cgttcaccac gacctggcaa cgcgtcttgc      300
tttcgtcgtc ccgattcatg attttcctcg cccttcgtca gcgctgcgcg agcatgaaac      360
gaatcgctca tcggcgcaca ggcgcgcgcc ggctgcccgg aggcactccc acgcctccct      420
cacggcaacc tcatcgctcc ggatgttccc gatggcgact cggatcgtgt acctgccgtg      480
gagacgggta tgggacaaaa ataccctgcc gacttgttg acctcgtcca gcagcgcctc      540
gttgaggcga tcgagctcgc gttcgatcga ctctctctct gcctcgtccg ccgaccgcat      600

| | | |
|---|---|---|
| gatgcaagcg agcgcggagg gcctcatgcg aaagcagacc gtactgaacg gcgtcggcgc | 660 | |
| gaggcgctcc caatcgggat cggcgtccac ccactgggcg agctgctgcc ccaatcggag | 720 | |
| gtgctcccgg atccgggccg ccagcccttc atgcccgaag tagcgcacga tcatccagag | 780 | |
| cttcagcgct cggaagcgcc gaccgagctg gataccccag tccatgtaat tcgtgacgtc | 840 | |
| gccctcggtg cggaggtatt cgggcaccag actgaacgcg cgcttcagtc ggtcggcgtc | 900 | |
| acgcacgtag agcacgctgc aatccatggg ggtgaacagc cacttgtgag ggttcactac | 960 | |
| cagcgagtcc gcccctcgc agcccgcgag cacgtccctg tgctcgggga cgatcgcggc | 1020 | |
| catccccgcg taggccgcgt ccacgtgaag ccatagcccg tgctcccggc aaacgctgac | 1080 | |
| gatggcgggg atgggtcga cgctcgtcgt ggacgtcgtg cccaccgtcg ccgcgacgca | 1140 | |
| gaagggtcgg aggccggccc cgaggtcctc cacgacggcg gcgcgcagcg cctcggggac | 1200 | |
| catgcggaag gccggatccg tggggatctt ccgcacccc tcctgcccga tgccgagggt | 1260 | |
| gatggctgcc ttctcgatgg atgagtgcgc ctgctccgac gcgtagagtc gcatgcgccg | 1320 | |
| ctgtcccgc atgccccgga gccggatggt cggctcggcc gagtcgcgcg cggccgcgat | 1380 | |
| cgcgaccatg ctggcggtcg acgcggtgtc catgatcgcg ccgtgcaagc cggcgtcgag | 1440 | |
| atccagcatc tgacgcagcc aggagaggac gagctcctcg agctcggtgg ccgccggcga | 1500 | |
| cgtgcgccat agcatcacgt tgacgttgag gcacgccgcg agcagctcgc cgaggatccc | 1560 | |
| aggaccagac gccgtgttcg cgaaatacgc gaagaatcgc ggatgattcc agtgcgtgat | 1620 | |
| ccccggcaga atgatctgct cgaaatcggt gagcacggcg tccatcggct ccggctcgac | 1680 | |
| gggcggggtc ggggccagcc tgcccttcac gtcgccgggg cggatcgcgg gaaagacggg | 1740 | |
| gtatcgatcc gggtggccga ggtaatcggc cgcccaatcg atgattctca taccgatccg | 1800 | |
| gcggaactcc tccagatcca tgtccccgag ccgttctttc cgcgggtcgc tcacgtcaac | 1860 | |
| ctcctcgccc tgccaggaca ggatcctcga ggtccctgg ctccggcggt ggaaagcgct | 1920 | |
| ccttgaacgt gaaggcccac ggggtcggtc cgtagcgccg caggtgctcg agccgatcct | 1980 | |
| gcccctcgcg gacggacggg atgtgcccgg ccgggaccca ccacagcacg aggtaatgcg | 2040 | |
| gctcgagatg ctcgaaccac cgagcgcgct gtcgcaggaa cgcggcatga tccgcggtgt | 2100 | |
| aggtgaaggc gaacaggtgc tcgatggagg tccataccga cagggtcacg aggagccgct | 2160 | |
| ggtccgggta cggacggatg gacacagagt tcccctcggc cgtctgcag | 2209 | |

<210> SEQ ID NO 62
<211> LENGTH: 512
<212> TYPE: PRT
<213> ORGANISM: Sorangium cellulosum
<220> FEATURE:
<223> OTHER INFORMATION: (ScDDC)

<400> SEQUENCE: 62

```
Met Ser Asp Pro Arg Lys Glu Arg Leu Gly Asp Met Asp Leu Glu Glu
1               5                   10                  15

Phe Arg Arg Ile Gly Met Arg Ile Ile Asp Trp Ala Ala Asp Tyr Leu
                20                  25                  30

Gly His Pro Asp Arg Tyr Pro Val Phe Pro Ala Ile Arg Pro Gly Asp
            35                  40                  45

Val Lys Gly Arg Leu Ala Pro Thr Pro Val Glu Pro Glu Pro Met
        50                  55                  60

Asp Ala Val Leu Thr Asp Phe Glu Gln Ile Ile Leu Pro Gly Ile Thr
65                  70                  75                  80
```

-continued

```
His Trp Asn His Pro Arg Phe Phe Ala Tyr Phe Ala Asn Thr Ala Ser
                 85                  90                  95
Gly Pro Gly Ile Leu Gly Glu Leu Leu Ala Ala Cys Leu Asn Val Asn
            100                 105                 110
Val Met Leu Trp Arg Thr Ser Pro Ala Ala Thr Glu Leu Glu Glu Leu
        115                 120                 125
Val Leu Ser Trp Leu Arg Gln Met Leu Asp Leu Asp Ala Gly Leu His
    130                 135                 140
Gly Ala Ile Met Asp Thr Ala Ser Thr Ala Ser Met Val Ala Ile Ala
145                 150                 155                 160
Ala Ala Arg Asp Ser Ala Glu Pro Thr Ile Arg Leu Arg Gly Met Ala
                165                 170                 175
Gly Gln Arg Arg Met Arg Leu Tyr Ala Ser Glu Gln Ala His Ser Ser
            180                 185                 190
Ile Glu Lys Ala Ala Ile Thr Leu Gly Ile Gly Gln Glu Gly Val Arg
        195                 200                 205
Lys Ile Pro Thr Asp Pro Ala Phe Arg Met Val Pro Glu Ala Leu Arg
    210                 215                 220
Ala Ala Val Val Glu Asp Leu Gly Ala Gly Leu Arg Pro Phe Cys Val
225                 230                 235                 240
Ala Ala Thr Val Gly Thr Thr Ser Thr Thr Ser Val Asp Pro Ile Pro
                245                 250                 255
Ala Ile Val Ser Val Cys Arg Glu His Gly Leu Trp Leu His Val Asp
            260                 265                 270
Ala Ala Tyr Ala Gly Met Ala Ala Ile Val Pro Glu His Arg Asp Val
        275                 280                 285
Leu Ala Gly Cys Glu Gly Ala Asp Ser Leu Val Val Asn Pro His Lys
    290                 295                 300
Trp Leu Phe Thr Pro Met Asp Cys Ser Val Leu Tyr Val Arg Asp Ala
305                 310                 315                 320
Asp Arg Leu Lys Arg Ala Phe Ser Leu Val Pro Glu Tyr Leu Arg Thr
                325                 330                 335
Glu Gly Asp Val Thr Asn Tyr Met Asp Trp Gly Ile Gln Leu Gly Arg
            340                 345                 350
Arg Phe Arg Ala Leu Lys Leu Trp Met Ile Val Arg Tyr Phe Gly His
        355                 360                 365
Glu Gly Leu Ala Ala Arg Ile Arg Glu His Leu Arg Leu Gly Gln Gln
    370                 375                 380
Leu Ala Gln Trp Val Asp Ala Asp Pro Asp Trp Glu Arg Leu Ala Pro
385                 390                 395                 400
Thr Pro Phe Ser Thr Val Cys Phe Arg Met Arg Pro Ser Ala Leu Ala
                405                 410                 415
Cys Ile Met Arg Ser Ala Asp Glu Ala Glu Arg Glu Ser Ile Glu Arg
            420                 425                 430
Glu Leu Asp Arg Leu Asn Glu Ala Leu Leu Asp Glu Val Asn Lys Ser
        435                 440                 445
Gly Arg Val Phe Leu Ser His Thr Arg Leu His Gly Arg Tyr Thr Ile
    450                 455                 460
Arg Val Ala Ile Gly Asn Ile Arg Ser Asp Glu Val Ala Val Arg Glu
465                 470                 475                 480
Ala Trp Glu Cys Leu Arg Ala Ala Gly Ala Arg Leu Cys Ala Asp Glu
                485                 490                 495
Arg Phe Val Ser Cys Ser Arg Ser Ala Asp Glu Gly Arg Gly Lys Ser
```

<210> SEQ ID NO 63
<211> LENGTH: 1341
<212> TYPE: DNA
<213> ORGANISM: Ceratitis capitata
<220> FEATURE:
<223> OTHER INFORMATION: (CcDDC)

<400> SEQUENCE: 63

| | |
|---|---|
| atggaggcgc cggagttcaa ggattttgcc aagacaatgg tcgactttat agccgaatat | 60 |
| ctggagaata tacgcgaaag gcgcgttctg ccggaagtga agcctggcta cctgaagcca | 120 |
| ttgattccgg atgctgcgcc cgagaagccg agaagtggc aggatgtgat gcaggacatc | 180 |
| gagcgagtca tcatgccggg cgtgacacac tggcacagtc ccaagttaca tgcctacttc | 240 |
| cccacggcca actcgtatcc agcgatcgtt gcggacatgc tgagtggagc gattgcctgc | 300 |
| atcggattca cgtggatcgc cagtcccgcg tgcacgcaac tcgaggtggt catgatggat | 360 |
| tggctgggca agatgctgga gctgccggca gagttcctgg cctgttcggg cggcaagggt | 420 |
| ggcggtgtca tccagggcac ggccagtggg tccacactgg tggctctgct gggagccaag | 480 |
| gccaagaagt tgaaggaggt gaaggagctc catccggagt gggatgagca caccatcctc | 540 |
| ggcaagcttg cgggctactg cagtgatcag gctcactcat ccgtggaaag agctggtttg | 600 |
| ctgggcggag tgaagcttgg atccgtgcag agtgagaacc accgtatgag aggtgctgcc | 660 |
| ttggaaaagg ccatcgagca ggatgtggcc gagggacgta ttcctttcta cgccgtggtg | 720 |
| accttgggca ccaccaacag ttgcgctttc gattatctcg atgagtgtgg gcccgtcggc | 780 |
| aataaacaca acctttggat ccatctcgat gcggcttatg ccggatccgc cttcatttgc | 840 |
| atggaatatc gtcaccctat gaagggaatc gagatggcgg acagtttcaa tttcaatcca | 900 |
| cacaaatgga tgcgtgtgaa cttcgactgc tcggccatgt ggctcaagga tccttcctgg | 960 |
| gtcgtgaatg cttttaacgc ggacccactg tacctgtacc ctaagcacga catgcagggt | 1020 |
| tcagctccgg actatcgtca ctggcaaatc ccacttggac ggcgattcag ggcactgaag | 1080 |
| ctctggttcg tcctccggct gtacggcgtc gagaatctcc aggcccacat ccgcagacac | 1140 |
| tgcaactttg ccaaacagtt cggggatctc tgcgtggcgc actccagatt tgaacctgcc | 1200 |
| gccgagatca atatgggatt ggtctgcttc cggcttacgg acacgcttgt tgtacaagaa | 1260 |
| ataataggaa gaaataaat taattttta acaaaaata caaatcaaaa aaaaaaaaa | 1320 |
| aaaaaaaaa aaaaaaaaa a | 1341 |

<210> SEQ ID NO 64
<211> LENGTH: 425
<212> TYPE: PRT
<213> ORGANISM: Ceratitis capitata
<220> FEATURE:
<223> OTHER INFORMATION: (CcDDC)

<400> SEQUENCE: 64

Met Glu Ala Pro Glu Phe Lys Asp Phe Ala Lys Thr Met Val Asp Phe
1               5                  10                  15

Ile Ala Glu Tyr Leu Glu Asn Ile Arg Glu Arg Arg Val Leu Pro Glu
            20                  25                  30

Val Lys Pro Gly Tyr Leu Lys Pro Leu Ile Pro Asp Ala Ala Pro Glu
        35                  40                  45

Lys Pro Glu Lys Trp Gln Asp Val Met Gln Asp Ile Glu Arg Val Ile
    50                  55                  60

Met Pro Gly Val Thr His Trp His Ser Pro Lys Leu His Ala Tyr Phe
 65                  70                  75                  80

Pro Thr Ala Asn Ser Tyr Pro Ala Ile Val Ala Asp Met Leu Ser Gly
             85                  90                  95

Ala Ile Ala Cys Ile Gly Phe Thr Trp Ile Ala Ser Pro Ala Cys Thr
            100                 105                 110

Gln Leu Glu Val Val Met Met Asp Trp Leu Gly Lys Met Leu Glu Leu
        115                 120                 125

Pro Ala Glu Phe Leu Ala Cys Ser Gly Gly Lys Gly Gly Gly Val Ile
130                 135                 140

Gln Gly Thr Ala Ser Gly Ser Thr Leu Val Ala Leu Leu Gly Ala Lys
145                 150                 155                 160

Ala Lys Lys Leu Lys Glu Val Lys Glu Leu His Pro Glu Trp Asp Glu
                165                 170                 175

His Thr Ile Leu Gly Lys Leu Ala Gly Tyr Cys Ser Asp Gln Ala His
            180                 185                 190

Ser Ser Val Glu Arg Ala Gly Leu Leu Gly Val Lys Leu Gly Ser
        195                 200                 205

Val Gln Ser Glu Asn His Arg Met Arg Gly Ala Ala Leu Glu Lys Ala
    210                 215                 220

Ile Glu Gln Asp Val Ala Glu Gly Arg Ile Pro Phe Tyr Ala Val Val
225                 230                 235                 240

Thr Leu Gly Thr Thr Asn Ser Cys Ala Phe Asp Tyr Leu Asp Glu Cys
                245                 250                 255

Gly Pro Val Gly Asn Lys His Asn Leu Trp Ile His Leu Asp Ala Ala
            260                 265                 270

Tyr Ala Gly Ser Ala Phe Ile Cys Met Glu Tyr Arg His Pro Met Lys
        275                 280                 285

Gly Ile Glu Met Ala Asp Ser Phe Asn Phe Asn Pro His Lys Trp Met
290                 295                 300

Arg Val Asn Phe Asp Cys Ser Ala Met Trp Leu Lys Asp Pro Ser Trp
305                 310                 315                 320

Val Val Asn Ala Phe Asn Ala Asp Pro Leu Tyr Leu Tyr Pro Lys His
                325                 330                 335

Asp Met Gln Gly Ser Ala Pro Asp Tyr Arg His Trp Gln Ile Pro Leu
            340                 345                 350

Gly Arg Arg Phe Arg Ala Leu Lys Leu Trp Phe Val Leu Arg Leu Tyr
        355                 360                 365

Gly Val Glu Asn Leu Gln Ala His Ile Arg Arg His Cys Asn Phe Ala
    370                 375                 380

Lys Gln Phe Gly Asp Leu Cys Val Ala His Ser Arg Phe Glu Pro Ala
385                 390                 395                 400

Ala Glu Ile Asn Met Gly Leu Val Cys Phe Arg Leu Thr Asp Thr Leu
                405                 410                 415

Val Val Gln Glu Ile Ile Gly Arg Lys
            420                 425

<210> SEQ ID NO 65
<211> LENGTH: 1221
<212> TYPE: DNA
<213> ORGANISM: Cryptosporidium parvum
<220> FEATURE:
<223> OTHER INFORMATION: (CpSAMS)

<400> SEQUENCE: 65

```
atggattctt cgaggtttag tggaaataaa tccacttaca ctgacttaca gactacttct      60
gaacaatttt tatttcttc agagtctgtt tgtagtggcc acccagataa attatgtgat     120
cagatttcgg atgcaatcct tgatgcgtgc ttggaacaag atccagaaag ctttgtagca    180
tgtgaaacat gcacaaaaac agggttcatt atggttttg gtgaaataac tacaaaggct     240
aatgtaaatt acgaaagagt tgtaagagaa acagtgaaag aaataggata tgactctgaa    300
gaaaagggt tagattacaa aactatggat gtgattatta agctagaaca acaaagtaat     360
caaattgctg gtgtgtaca tgtagataaa aatgtagaag atattggagc gggtgaccaa    420
ggaatgatgt ttggttatgc tacgaatgaa acaaaagaac tcatgcctct gacgcacgta    480
ttagctacat ctattacaag agagctggat tatatcagag tgaaaggagt atcttctcgg    540
gtgggttggc tgcgccctga tgaaaggcg caagtgacag tagaatataa ctgcaaacat      600
ggcgtgctca ttccaaaaag aattcacact attttagttt cggttcagca tgatgaaaac    660
atagaaaacg aggaaattag agaatttgta ctggagaatg taattaaaaa agtatgccct    720
tcagatttga tggacaaaga aactagaata ttaattaatc catctggcag gtttacaatt    780
ggtgggccag cagcagatgc tggattaaca gggcgcaaga taattgtaga tacatacgga    840
ggatggggtg ctcatggggg tggtgcattt agcgggaaag atgcaactaa agtagataga    900
tcaggtgcat atatggcaag gcttgttgca aagtcaatcg tcttttccgg cttgtgtagc    960
agatgtttgg tacaggtttc gtatggaatt ggaatagcaa ggcctttgtc actgtatatt   1020
aatacatttg gcacagcgaa agatgggtat aatgacgcaa aactactgga gatagttaat   1080
aaggtatttg attttaggcc aggaattcta attaagcagc taaaccttaa atctcctatt   1140
tttaaaaaga catcaagtgg cggacatttt ggacgatcag aagaagagtt tctttgggaa   1200
aagccaatta ttttacaata g                                             1221
```

<210> SEQ ID NO 66
<211> LENGTH: 406
<212> TYPE: PRT
<213> ORGANISM: Cryptosporidium parvum
<220> FEATURE:
<223> OTHER INFORMATION: (CpSAMS)

<400> SEQUENCE: 66

```
Met Asp Ser Ser Arg Phe Ser Gly Asn Lys Ser Thr Tyr Thr Asp Leu
1               5                   10                  15
Gln Thr Thr Ser Glu Gln Phe Leu Phe Ser Ser Glu Ser Val Cys Ser
            20                  25                  30
Gly His Pro Asp Lys Leu Cys Asp Gln Ile Ser Asp Ala Ile Leu Asp
        35                  40                  45
Ala Cys Leu Glu Gln Asp Pro Glu Ser Phe Val Ala Cys Glu Thr Cys
    50                  55                  60
Thr Lys Thr Gly Phe Ile Met Val Phe Gly Glu Ile Thr Thr Lys Ala
65                  70                  75                  80
Asn Val Asn Tyr Glu Arg Val Val Arg Glu Thr Val Lys Glu Ile Gly
                85                  90                  95
Tyr Asp Ser Glu Glu Lys Gly Leu Asp Tyr Lys Thr Met Asp Val Ile
            100                 105                 110
Ile Lys Leu Glu Gln Gln Ser Asn Gln Ile Ala Gly Cys Val His Val
        115                 120                 125
Asp Lys Asn Val Glu Asp Ile Gly Ala Gly Asp Gln Gly Met Met Phe
    130                 135                 140
```

Gly Tyr Ala Thr Asn Glu Thr Lys Glu Leu Met Pro Leu Thr His Val
145                 150                 155                 160

Leu Ala Thr Ser Ile Thr Arg Glu Leu Asp Tyr Ile Arg Val Lys Gly
                165                 170                 175

Val Ser Ser Arg Val Gly Trp Leu Arg Pro Asp Gly Lys Ala Gln Val
            180                 185                 190

Thr Val Glu Tyr Asn Cys Lys His Gly Val Leu Ile Pro Lys Arg Ile
        195                 200                 205

His Thr Ile Leu Val Ser Val Gln His Asp Glu Asn Ile Glu Asn Glu
    210                 215                 220

Glu Ile Arg Glu Phe Val Leu Glu Asn Val Ile Lys Lys Val Cys Pro
225                 230                 235                 240

Ser Asp Leu Met Asp Lys Glu Thr Arg Ile Leu Ile Asn Pro Ser Gly
                245                 250                 255

Arg Phe Thr Ile Gly Gly Pro Ala Ala Asp Ala Gly Leu Thr Gly Arg
                260                 265                 270

Lys Ile Ile Val Asp Thr Tyr Gly Gly Trp Gly Ala His Gly Gly Gly
            275                 280                 285

Ala Phe Ser Gly Lys Asp Ala Thr Lys Val Asp Arg Ser Gly Ala Tyr
        290                 295                 300

Met Ala Arg Leu Val Ala Lys Ser Ile Val Phe Ser Gly Leu Cys Ser
305                 310                 315                 320

Arg Cys Leu Val Gln Val Ser Tyr Gly Ile Gly Ile Ala Arg Pro Leu
                325                 330                 335

Ser Leu Tyr Ile Asn Thr Phe Gly Thr Ala Lys Asp Gly Tyr Asn Asp
                340                 345                 350

Ala Lys Leu Leu Glu Ile Val Asn Lys Val Phe Asp Phe Arg Pro Gly
            355                 360                 365

Ile Leu Ile Lys Gln Leu Asn Leu Lys Ser Pro Ile Phe Lys Lys Thr
        370                 375                 380

Ser Ser Gly Gly His Phe Gly Arg Ser Glu Glu Glu Phe Leu Trp Glu
385                 390                 395                 400

Lys Pro Ile Ile Leu Gln
                405

<210> SEQ ID NO 67
<211> LENGTH: 1179
<212> TYPE: DNA
<213> ORGANISM: Leishmania donovani
<220> FEATURE:
<223> OTHER INFORMATION: (LdSAMS)

<400> SEQUENCE: 67
atgtctgtcc acagcattct cttctcctcc gagcacgtga cggagggcca tccagacaag      60
ctgtgcgatc aggtatccga cgctgtgctt gacgcgtgcc tcgccggcga cccgttctcg     120
aaggttgcgt gcgagtcgtg cgcgaagacg ggcatggtga tggtgttcgg cgagatcacg     180
acaaaggcag tgctagacta ccagaagatc gtccgcaaca cgatcaagga cattggcttc     240
gattccgcgg acaagggtct ggactacgag tcgtgcaatg tgctggttgc gattgagcag     300
cagtcgccgg acatctgcca gggtctgggc aacttcgata gcgaggatct cggcgctggc     360
gaccagggca tgatgttcgg ctacgcgacg acgagacgg agacgctgat gccgctgacg     420
tacgagctgg cccgcggcct tgcgaagaag tacagcgagc ttcgccgctc cggcagcctg     480
gagtgggctc gcccggacgc gaagacgcag gtgacggtgg agtacgacta cgacacgcgc     540

-continued

```
gagggcaagc aggtgctgac gccgaagcgc gtggcggtgg tgctgatctc tgcgcagcac     600
gacgagcacg tgaccaacga taagatcagc gtggatctga tggagaaggt gatcaaggct     660
gtgatccctg cgaacatgct ggacgcggag acgaagtact ggctgaaccc atctggccgc     720
ttcgtgcgcg gtgggccgca tggcgacgcc ggtctgactg gccgaaagat catcgtagac     780
acgtacggcg gctggggcgc gcacggcggt ggcgccttct ccggtaagga cccttcgaag     840
gtggaccgct ccgccgcgta cgccgcgcga tggatcgcga agtcgatcgt tgcaggtggc     900
ctggcgcgcc gctgccttgt gcagctcgcg tacgccatcg tgtagcggga gccgctgagc     960
atgcacgtgg agacgtacgg caccggcaag tacgatgacg cgaagctgct ggagatcgtg    1020
aagcagaact tcaagctgcg cccgtacgac atcatccagg agctgaacct gcgccgcccc    1080
atctactacg atacgtcgcg cttcggccac ttcggccgta aggacgagtt gggcacgggc    1140
gggttcactt gggaggtgcc aaagaagatg gtcgagtaa                           1179
```

<210> SEQ ID NO 68
<211> LENGTH: 392
<212> TYPE: PRT
<213> ORGANISM: Leishmania donovani
<220> FEATURE:
<223> OTHER INFORMATION: (LdSAMS)

<400> SEQUENCE: 68

```
Met Ser Val His Ser Ile Leu Phe Ser Ser Glu His Val Thr Glu Gly
  1               5                  10                  15

His Pro Asp Lys Leu Cys Asp Gln Val Ser Asp Ala Val Leu Asp Ala
             20                  25                  30

Cys Leu Ala Gly Asp Pro Phe Ser Lys Val Ala Cys Glu Ser Cys Ala
         35                  40                  45

Lys Thr Gly Met Val Met Val Phe Gly Glu Ile Thr Thr Lys Ala Val
     50                  55                  60

Leu Asp Tyr Gln Lys Ile Val Arg Asn Thr Ile Lys Asp Ile Gly Phe
 65                  70                  75                  80

Asp Ser Ala Asp Lys Gly Leu Asp Tyr Glu Ser Cys Asn Val Leu Val
                 85                  90                  95

Ala Ile Glu Gln Gln Ser Pro Asp Ile Cys Gln Gly Leu Gly Asn Phe
            100                 105                 110

Asp Ser Glu Asp Leu Gly Ala Gly Asp Gln Gly Met Met Phe Gly Tyr
        115                 120                 125

Ala Thr Asp Glu Thr Glu Thr Leu Met Pro Leu Thr Tyr Glu Leu Ala
    130                 135                 140

Arg Gly Leu Ala Lys Lys Tyr Ser Glu Leu Arg Arg Ser Gly Ser Leu
145                 150                 155                 160

Glu Trp Ala Arg Pro Asp Ala Lys Thr Gln Val Thr Val Glu Tyr Asp
                165                 170                 175

Tyr Asp Thr Arg Glu Gly Lys Gln Val Leu Thr Pro Lys Arg Val Ala
            180                 185                 190

Val Val Leu Ile Ser Ala Gln His Asp Glu His Val Thr Asn Asp Lys
        195                 200                 205

Ile Ser Val Asp Leu Met Glu Lys Val Ile Lys Ala Val Ile Pro Ala
    210                 215                 220

Asn Met Leu Asp Ala Glu Thr Lys Tyr Trp Leu Asn Pro Ser Gly Arg
225                 230                 235                 240

Phe Val Arg Gly Gly Pro His Gly Asp Ala Gly Leu Thr Gly Arg Lys
```

245                 250                 255
Ile Ile Val Asp Thr Tyr Gly Gly Trp Gly Ala His Gly Gly Ala
            260                 265                 270

Phe Ser Gly Lys Asp Pro Ser Lys Val Asp Arg Ser Ala Ala Tyr Ala
            275                 280                 285

Ala Arg Trp Ile Ala Lys Ser Ile Val Ala Gly Gly Leu Ala Arg Arg
            290                 295                 300

Cys Leu Val Gln Leu Ala Tyr Ala Ile Gly Val Ala Glu Pro Leu Ser
305                 310                 315                 320

Met His Val Glu Thr Tyr Gly Thr Gly Lys Tyr Asp Asp Ala Lys Leu
                325                 330                 335

Leu Glu Ile Val Lys Gln Asn Phe Lys Leu Arg Pro Tyr Asp Ile Ile
            340                 345                 350

Gln Glu Leu Asn Leu Arg Arg Pro Ile Tyr Tyr Asp Thr Ser Arg Phe
            355                 360                 365

Gly His Phe Gly Arg Lys Asp Glu Leu Gly Thr Gly Gly Phe Thr Trp
            370                 375                 380

Glu Val Pro Lys Lys Met Val Glu
385                 390

<210> SEQ ID NO 69
<211> LENGTH: 1200
<212> TYPE: DNA
<213> ORGANISM: Mycobacterium smegmatis
<220> FEATURE:
<223> OTHER INFORMATION: (MsSAMS)

<400> SEQUENCE: 69
gtgagcaaag gtcgcctgtt taccagtgag tcggtaaccg aagggcaccc cgacaagatc    60
tgtgacgcaa tcagcgactc tgtgctcgac gcgctgctgg agcaggatcc caagtcccgc   120
gtcgccgtcg agacgctggt caccacgggc caggtgcacg tcgccggtga ggtgaccacc   180
acggcgtacg ccgacatccc caagatcgtg cgcgaccgca tcctcgacat cggctacgac   240
tcgtcgacca agggcttcga cggcgcctcg tgcggcgtca cgtggcgat cggtgcgcag    300 tcgcccgaca tcgcccaagg cgtcgacacc gcccacgaga cccgcgtcga gggcaaggcc   360
gacccgctgg acctgcaggg cgcaggcgac cagggcctga tgttcggcta cgccatcggc   420
gacacccccg aactcatgcc gctgcccatc gcgctggccc accgcctcgc gcgccgcctg   480
accgaggtgc gcaagaacgg tgtgctggac tacctgcggc ccgacggcaa gacccaggtc   540
accatccagt acgacggcac cacccccggtg cggttggaca ccgtggtgct gtccaccccag  600 cacgccgacg gcatcgacct ggagggcacc ctcacgcccg acatccgcga aggtcgtc    660 aacaccgtgc tcgccgatct cggccatgag accctcgaca cgtccgacta ccgcctgctg   720
gtcaacccga cgggcaagtt cgtcctcggc ggccccatgg gcgacgccgg cctgaccggc   780
cgcaagatca tcgtcgacac ctacggcggc tgggctcgcc acggcggcgg cgccttctcg   840
ggcaaggatc cgtcaaaggt cgaccgctcg ccgcctacg cgatgcgctg ggtcgccaag    900
aacgtcgtcg ccgctggcct ggccgagcgc gtcgaggtgc aggtcgccta cgcgatcggc   960
aaggccgccc cggtgggtct gttcgtggag accttcggca gcgagaccgt cgacccggcc  1020
aagatcgaga aggccatcgg cgaggtgttc gacctgcgtc ccgccgcgat cgtgcgcgac  1080
ctcgacctgc tgcgcccgat ctacgcgccc accgccgcgt acggacactt cggccgcacc  1140
gacatcgagc tgccgtggga gcagaccaac aaggtggacg acctgaagtc cgccatctga  1200

<210> SEQ ID NO 70
<211> LENGTH: 399
<212> TYPE: PRT
<213> ORGANISM: Mycobacterium smegmatis
<220> FEATURE:
<223> OTHER INFORMATION: (MsSAMS)

<400> SEQUENCE: 70

Met Ser Lys Gly Arg Leu Phe Thr Ser Glu Ser Val Thr Glu Gly His
1               5                   10                  15

Pro Asp Lys Ile Cys Asp Ala Ile Ser Asp Ser Val Leu Asp Ala Leu
                20                  25                  30

Leu Glu Gln Asp Pro Lys Ser Arg Val Ala Val Glu Thr Leu Val Thr
            35                  40                  45

Thr Gly Gln Val His Val Ala Gly Glu Val Thr Thr Thr Ala Tyr Ala
        50                  55                  60

Asp Ile Pro Lys Ile Val Arg Asp Arg Ile Leu Asp Ile Gly Tyr Asp
65                  70                  75                  80

Ser Ser Thr Lys Gly Phe Asp Gly Ala Ser Cys Gly Val Asn Val Ala
                85                  90                  95

Ile Gly Ala Gln Ser Pro Asp Ile Ala Gln Gly Val Asp Thr Ala His
            100                 105                 110

Glu Thr Arg Val Glu Gly Lys Ala Asp Pro Leu Asp Leu Gln Gly Ala
        115                 120                 125

Gly Asp Gln Gly Leu Met Phe Gly Tyr Ala Ile Gly Asp Thr Pro Glu
130                 135                 140

Leu Met Pro Leu Pro Ile Ala Leu Ala His Arg Leu Ala Arg Arg Leu
145                 150                 155                 160

Thr Glu Val Arg Lys Asn Gly Val Leu Asp Tyr Leu Arg Pro Asp Gly
                165                 170                 175

Lys Thr Gln Val Thr Ile Gln Tyr Asp Gly Thr Thr Pro Val Arg Leu
            180                 185                 190

Asp Thr Val Val Leu Ser Thr Gln His Ala Asp Gly Ile Asp Leu Glu
        195                 200                 205

Gly Thr Leu Thr Pro Asp Ile Arg Glu Lys Val Val Asn Thr Val Leu
210                 215                 220

Ala Asp Leu Gly His Glu Thr Leu Asp Thr Ser Asp Tyr Arg Leu Leu
225                 230                 235                 240

Val Asn Pro Thr Gly Lys Phe Val Leu Gly Gly Pro Met Gly Asp Ala
                245                 250                 255

Gly Leu Thr Gly Arg Lys Ile Ile Val Asp Thr Tyr Gly Gly Trp Ala
            260                 265                 270

Arg His Gly Gly Gly Ala Phe Ser Gly Lys Asp Pro Ser Lys Val Asp
        275                 280                 285

Arg Ser Ala Ala Tyr Ala Met Arg Trp Val Ala Lys Asn Val Val Ala
290                 295                 300

Ala Gly Leu Ala Glu Arg Val Glu Val Gln Val Ala Tyr Ala Ile Gly
305                 310                 315                 320

Lys Ala Ala Pro Val Gly Leu Phe Val Glu Thr Phe Gly Ser Glu Thr
                325                 330                 335

Val Asp Pro Ala Lys Ile Glu Lys Ala Ile Gly Glu Val Phe Asp Leu
            340                 345                 350

Arg Pro Ala Ala Ile Val Arg Asp Leu Asp Leu Leu Arg Pro Ile Tyr
        355                 360                 365

```
Ala Pro Thr Ala Ala Tyr Gly His Phe Gly Arg Thr Asp Ile Glu Leu
    370                 375                 380

Pro Trp Glu Gln Thr Asn Lys Val Asp Asp Leu Lys Ser Ala Ile
385                 390                 395

<210> SEQ ID NO 71
<211> LENGTH: 3398
<212> TYPE: DNA
<213> ORGANISM: Bos taurus
<220> FEATURE:
<223> OTHER INFORMATION: (BtSAMS)

<400> SEQUENCE: 71
gaccagtcag agggagtgac acatcgctct ccagtccctc ctcctcgccc gtccgcacct      60
ttactcacgt gctggcggac acttaggcag aagtgagccc cgtggctctg ccaaagacga     120
gcctgttggc tttaaaggag gaaaattaaa aaaaccttag gccaggtccc agcattaaaa     180
ttgttacctt gaagacgctg agtggagaag tgtgaagaga tgaatggacc agtggatggc     240
ttgtgtgatc attctctaag tgaggaagga gcattcatgt tcacatcgga atctgtagga     300
gaggggcacc cggataagat ctgtgaccag atcagtgatg cagtgctgga tgcccatctc     360
aagcaggacc ccaatgccaa ggtggcctgt gagacggtgt gtaagacggg catggtgctt     420
ctgtgcgggg agatcacctc catggccatg gtggattacc agcgtgtggt gcgggagacc     480
atccagcaca tcggctacga cgactccgcc aagggctttg actttaagac tgcaacgtg      540 ctggtggctt tggagcagca gtccccggat atcgcccagt gtgtccacct ggacagaaat     600
gaagaggatg tcggtgccgg agatcagggg ctgatgtttg gctatgccac ggatgagacg     660
gaagagtgca tgccccctcac catcatgctg gcgcacagac tcaacgcccg catggcagag     720
ctgcgacgct cagggcagct ccctggctg caacctgact ccaagacaca ggtgacagtg     780
cagtacacgc aggacaacgg tgcggtcatc cctatgcgcg tccataccgt cgtcatctcc     840
gtgcagcaca cgaagacat aacgctggag gacatgcgca gagccctgaa ggagcaggtg     900
atcagggctg ttgtgccagc acggtacctg gacgaggaca ccatctacca cctgcagccc     960
agtgggcgct ttgtcatcgg aggcccccag ggggatgccg tgtcactgg ccgaaagatc    1020 atcgtggaca cctatggcgg ctggggggca cacggcggag gcgccttctc tgggaaggac    1080
tacaccaagg tggaccgctc ggcagcgtac gctgcccgct gggtggccaa gtccctggtg    1140
aaagcagggc tctgccggag ggtgcttgtg caggtgtcct atgccattgg tgtggctgag    1200
ccactgtcta tttccatctt tacctatgga acctcccaga agacagagag agagctgctg    1260
gatgtggtca ataagaactt tgaccttcgg cctggtgtta tcgtcaggga cttggacttg    1320
aagaagccca tctaccagaa gacagcatgc tacggccact cgggaggag cgagttccct    1380 tgggaagttc ccaaaaagct tgtgttttag tgctggtggg ggccactcca gctggtgagc    1440
cctggaggct tcaggtggga cagagccatg ctcttctcct ccaggaccct gactctcaga    1500
tcacccactg ccccttcct gggcagagcc aggcccctct gacttagcag gaggaagggg    1560
gccttctggt gccagggctc agatctcctc atgaggccag tcactatgtt tcctgcctc    1620 tcccccagac caaggtgatg tgaatttagt ggaaatagca tccctgtcag aggaaacctg    1680
ctcactcccc tgcccccaca gcctggaccc tgagtggccc ctccttccct ggtgtgtgct    1740
gggaagatct tagggctcca tgagggtctg ggtgtgccgg gccacccttc acgtctgcag    1800
ccatttggtc gccgtcctga gcctgagcct tcccatgggc cctcccaggc catgcttgtg    1860
gcagggatga cagcagctag cgtgtgagag accaagctca tcactgatct catttcttct    1920
```

```
tcactgcaat acgatgaggt gacaccttgt gttacaagca tttaaggtga ggaggccgag    1980
ctaactttca cagggcccac agctgcatgg gtcagggcct agacatgcgt ctggtatctt    2040
tgaattgtga gcccatacac tttgacccct caccctcagc accgcccccc accccgatct    2100
catgctagaa acaggtctga gtgaagagat gaggctgtga cctctgtcct gaagacctga    2160
cgttgctggg agttagggga tcgagtccct tggcgacccc tgaacagtga tctacagagc    2220
caagtcagaa ccaaagggat gtttcctttg cctctgtaat tcagaagat agattagggt     2280
gtgctggata tcctggcccc tggggctgcg ctggagtttg aaattaagag gcacctatgt    2340
tatcccagcc cctgactact cagggacatg cagggttggg cccatggact cctccgatga    2400
gggtccaagg ccagtcctgt cccgtatagg gcttcctaga gcagaagcag cagcttgtcc    2460
cttaaacaag ggatagaatc ctgtgtcctc cacatgcttc tctctctctg accccttct     2520
ctctctcttg taacccctgc aatctgagtg ctgttggaat aagtgggtga gcctctcaga    2580
tcccccttcc agagaggaca gcccaaaggc ctgaattcaa atgttaaatg gtgactgaag    2640
tggcaagtct tgactcctag agggagctaa gttggctgag atgtcatgag gagatttctg    2700
cctttgccag gtggcctctg gggccagggc tacccctgag gtcttgggtg attcttggca    2760
cattaaggtc ttagaagcta tgcattctct tgctttcctt tccatggcca gtacctccct    2820
gtactccttc cccaacctgg gcctctgact gctgcactgc taccttatcc ccagctccgc    2880
agaccacagg ttcaggtagg agcccccaca ggtccccgga gaatactggg gtctggcttc    2940
ttcctgtggc actcggtgcc agctccagct gagatgcaca gctcaggaag cctcatttgg    3000
gcagcagaca gcctgcactg aactgtaggc ctgaagcaca aaaaccttg gctttctctt     3060
tccatcaggg gaaaggcagc agttcagggc agaaaaagaa gcccagatga ccataaacac    3120
ctaaagctga tgtgtgatat ggaagctcag gagtctcata gggctctggt cacttgggaa    3180
gtctcaagtt cctttcctt taggtttgca ggtggctgag ttcctctaac ttgggccata    3240
tttgaagtga aaatgcaaat ttttatactt tctgcacccc ctgggagaaa caaggttttc    3300
ttgggtcaac actgttatat gaaactcgag tcttattc taatagtgc ctgctaagcc       3360
agtgaataaa aactcgagaa gcaaaaaaaa aaaaaaaa                            3398
```

<210> SEQ ID NO 72
<211> LENGTH: 396
<212> TYPE: PRT
<213> ORGANISM: Bos taurus
<220> FEATURE:
<223> OTHER INFORMATION: (BtSAMS)

<400> SEQUENCE: 72

```
Met Asn Gly Pro Val Asp Gly Leu Cys Asp His Ser Leu Ser Glu Glu
1               5                   10                  15

Gly Ala Phe Met Phe Thr Ser Glu Ser Val Gly Glu Gly His Pro Asp
            20                  25                  30

Lys Ile Cys Asp Gln Ile Ser Asp Ala Val Leu Asp Ala His Leu Lys
        35                  40                  45

Gln Asp Pro Asn Ala Lys Val Ala Cys Glu Thr Val Cys Lys Thr Gly
    50                  55                  60

Met Val Leu Leu Cys Gly Glu Ile Thr Ser Met Ala Met Val Asp Tyr
65                  70                  75                  80

Gln Arg Val Val Arg Glu Thr Ile Gln His Ile Gly Tyr Asp Asp Ser
                85                  90                  95
```

```
Ala Lys Gly Phe Asp Phe Lys Thr Cys Asn Val Leu Val Ala Leu Glu
            100                 105                 110

Gln Gln Ser Pro Asp Ile Ala Gln Cys Val His Leu Asp Arg Asn Glu
        115                 120                 125

Glu Asp Val Gly Ala Gly Asp Gln Gly Leu Met Phe Gly Tyr Ala Thr
    130                 135                 140

Asp Glu Thr Glu Glu Cys Met Pro Leu Thr Ile Met Leu Ala His Arg
145                 150                 155                 160

Leu Asn Ala Arg Met Ala Glu Leu Arg Arg Ser Gly Gln Leu Pro Trp
                165                 170                 175

Leu Gln Pro Asp Ser Lys Thr Gln Val Thr Val Gln Tyr Thr Gln Asp
            180                 185                 190

Asn Gly Ala Val Ile Pro Met Arg Val His Thr Val Ile Ser Val
        195                 200                 205

Gln His Asn Glu Asp Ile Thr Leu Glu Asp Met Arg Arg Ala Leu Lys
    210                 215                 220

Glu Gln Val Ile Arg Ala Val Pro Ala Arg Tyr Leu Asp Glu Asp
225                 230                 235                 240

Thr Ile Tyr His Leu Gln Pro Ser Gly Arg Phe Val Ile Gly Pro
                245                 250                 255

Gln Gly Asp Ala Gly Val Thr Gly Arg Lys Ile Ile Val Asp Thr Tyr
            260                 265                 270

Gly Gly Trp Gly Ala His Gly Gly Ala Phe Ser Gly Lys Asp Tyr
                275                 280                 285

Thr Lys Val Asp Arg Ser Ala Ala Tyr Ala Ala Arg Trp Val Ala Lys
            290                 295                 300

Ser Leu Val Lys Ala Gly Leu Cys Arg Arg Val Leu Val Gln Val Ser
305                 310                 315                 320

Tyr Ala Ile Gly Val Ala Glu Pro Leu Ser Ile Ser Ile Phe Thr Tyr
                325                 330                 335

Gly Thr Ser Gln Lys Thr Glu Arg Glu Leu Leu Asp Val Val Asn Lys
            340                 345                 350

Asn Phe Asp Leu Arg Pro Gly Val Ile Val Arg Asp Leu Asp Leu Lys
            355                 360                 365

Lys Pro Ile Tyr Gln Lys Thr Ala Cys Tyr Gly His Phe Gly Arg Ser
    370                 375                 380

Glu Phe Pro Trp Glu Val Pro Lys Lys Leu Val Phe
385                 390                 395

<210> SEQ ID NO 73
<211> LENGTH: 1922
<212> TYPE: DNA
<213> ORGANISM: Populus x generosa strain H11
<220> FEATURE:
<223> OTHER INFORMATION: (Ptd4CL)

<400> SEQUENCE: 73
catttctctc tctttccaat caatggaggc caataaggat caagtacaag aattcatttt       60
caggtccaaa ctccctgaca tctatatccc aaaccacctc cctttacaca cttattgctt      120
cgaaaagctt tcccaattca agacaaaccc ttgcttgatc aatggcccta ccggtgatat      180
ctacacttat gcggatgttg agctcacatc acgcaaagtt gcctctggcc tctacaagtt      240
aggcctccaa caaggcgatg ttatattgct cttgctccaa aactcgccag aatttgtttt      300
tgcattcctt ggagcgtcgt tcattggcgc tattagctca actgcaaacc ctttctatac      360
```

-continued

```
ttcagctgag atcgcaaaac aagcaacagc atcaaaggca aagctgataa taacacatgc   420
agcgtacgcc gagaaagtgc aacagtttgc tcaagaaaat gatcatgtta agataatgac   480
catcgattct cttacagaaa actgcttgca tttctcagag ttgacaagct ctgatgagaa   540
tgaaatccct actgtcaaga ttaagcctga tgatatcatg cactcccat attcgtcagg    600
gactacaggt ctccctaaag gtgtcatgtt gactcataaa gggcttgtta ctagtgtggc   660
acaacaagtt gatggagaga accctaatct ctattttcac gagagggatg tgattctttg   720
tgtgctgcct ttgttccaca tctattcact caattccgta ttcctttgtg ggctaagagc   780
tggttcagca attttggtta tgcaaaaatt cgatacggtt tcattaatgg accttgtaca   840
gaaatataag gtgacaattg ctccactcgt gcccctatc tgtctggcaa ttgcaaaaag    900
tccagtcgtt gatcagtatg atctttcttc gatccggaca gtactgtctg cgcagcacc    960
tttggggaag gagcttgagg atacagtcag agctaagctg cctaatgcta aacttggaca  1020
gggatatgga atgacagagg cagggcccgt gatagcaatg tgcttagctt ttgcaaagga  1080
accctttgag attaaatctg cgcatgtgg gactgttgtt agaaatgcag agatgaagat   1140
tgtcgacccg gaaaccggtg agtcccagcc gcgaaataaa accggcgaga tttgcattag  1200
gggttgccaa ataatgaaag gttatctaaa tgatcctgag gcaactgaaa ggacgataga  1260
caaagatgga tggttgcaca cgggtgatat tggatacatt gatgaagatg aactctttat  1320
cgtggatcgt ttgaaagaat tgatcaaata caaaggtttc caagtagcac ctgctgagct  1380
tgaagcaatg ttgattgctc atcccaacat ctctgatgct gctgtagtac ccatgaaaga  1440
tgaagctgcc ggagaggttc cggttgcttt tgtggtgcga tcaaatggtt ccaagatcac  1500
cgaggatgaa atcaaacaat atatctcaaa acaggtgatc ttttataaga gaatcggtcg  1560
ggttttcttc acggaggcca tccccaaggc cccgtcggga aaaatcttga gaaaggacct  1620
cagagcaagg gtttctgctg gtgatcttcc atgcacatca gattcctaat atgacatata  1680
tgcaaaccag cattagtttg aagttcagag gcagaatgga tctgatgtgt ttttcaaaag  1740
ggtttcaaaa gggagaggag aatatgtaaa cttgaagatt tcagagcctt caatgttcag  1800
ttgttgctat cgacctaaac tatgatgctt ggtgaataga agaacgagat ttgtattaat  1860
taatggtggc tagcgttgca aagtcaaacc attcttgtta gcaaacctcc ttcttcagtg  1920
tg                                                                  1922
```

<210> SEQ ID NO 74
<211> LENGTH: 548
<212> TYPE: PRT
<213> ORGANISM: Populus x generosa strain H11
<220> FEATURE:
<223> OTHER INFORMATION: (Ptd4CL)

<400> SEQUENCE: 74

```
Met Glu Ala Asn Lys Asp Gln Val Gln Glu Phe Ile Phe Arg Ser Lys
1               5                   10                  15

Leu Pro Asp Ile Tyr Ile Pro Asn His Leu Pro Leu His Thr Tyr Cys
            20                  25                  30

Phe Glu Lys Leu Ser Gln Phe Lys Asp Asn Pro Cys Leu Ile Asn Gly
        35                  40                  45

Pro Thr Gly Asp Ile Tyr Thr Tyr Ala Asp Val Glu Leu Thr Ser Arg
    50                  55                  60

Lys Val Ala Ser Gly Leu Tyr Lys Leu Gly Leu Gln Gln Gly Asp Val
65                  70                  75                  80
```

```
Ile Leu Leu Leu Leu Gln Asn Ser Pro Glu Phe Val Phe Ala Phe Leu
                85                  90                  95

Gly Ala Ser Phe Ile Gly Ala Ile Ser Ser Thr Ala Asn Pro Phe Tyr
            100                 105                 110

Thr Ser Ala Glu Ile Ala Lys Gln Ala Thr Ala Ser Lys Ala Lys Leu
            115                 120                 125

Ile Ile Thr His Ala Ala Tyr Ala Glu Lys Val Gln Gln Phe Ala Gln
            130                 135                 140

Glu Asn Asp His Val Lys Ile Met Thr Ile Asp Ser Leu Thr Glu Asn
145                 150                 155                 160

Cys Leu His Phe Ser Glu Leu Thr Ser Ser Asp Glu Asn Glu Ile Pro
                165                 170                 175

Thr Val Lys Ile Lys Pro Asp Asp Ile Met Ala Leu Pro Tyr Ser Ser
            180                 185                 190

Gly Thr Thr Gly Leu Pro Lys Gly Val Met Leu Thr His Lys Gly Leu
            195                 200                 205

Val Thr Ser Val Ala Gln Gln Val Asp Gly Glu Asn Pro Asn Leu Tyr
210                 215                 220

Phe His Glu Arg Asp Val Ile Leu Cys Val Leu Pro Leu Phe His Ile
225                 230                 235                 240

Tyr Ser Leu Asn Ser Val Phe Leu Cys Gly Leu Arg Ala Gly Ser Ala
                245                 250                 255

Ile Leu Val Met Gln Lys Phe Asp Thr Val Ser Leu Met Asp Leu Val
            260                 265                 270

Gln Lys Tyr Lys Val Thr Ile Ala Pro Leu Val Pro Pro Ile Cys Leu
            275                 280                 285

Ala Ile Ala Lys Ser Pro Val Val Asp Gln Tyr Asp Leu Ser Ser Ile
            290                 295                 300

Arg Thr Val Leu Ser Gly Ala Ala Pro Leu Gly Lys Glu Leu Glu Asp
305                 310                 315                 320

Thr Val Arg Ala Lys Leu Pro Asn Ala Lys Leu Gly Gln Gly Tyr Gly
            325                 330                 335

Met Thr Glu Ala Gly Pro Val Ile Ala Met Cys Leu Ala Phe Ala Lys
            340                 345                 350

Glu Pro Phe Glu Ile Lys Ser Gly Ala Cys Gly Thr Val Val Arg Asn
            355                 360                 365

Ala Glu Met Lys Ile Val Asp Pro Glu Thr Gly Glu Ser Gln Pro Arg
            370                 375                 380

Asn Lys Thr Gly Glu Ile Cys Ile Arg Gly Cys Gln Ile Met Lys Gly
385                 390                 395                 400

Tyr Leu Asn Asp Pro Glu Ala Thr Glu Arg Thr Ile Asp Lys Asp Gly
                405                 410                 415

Trp Leu His Thr Gly Asp Ile Gly Tyr Ile Asp Glu Asp Glu Leu Phe
            420                 425                 430

Ile Val Asp Arg Leu Lys Glu Leu Ile Lys Tyr Lys Gly Phe Gln Val
            435                 440                 445

Ala Pro Ala Glu Leu Glu Ala Met Leu Ile Ala His Pro Asn Ile Ser
            450                 455                 460

Asp Ala Ala Val Val Pro Met Lys Asp Glu Ala Ala Gly Glu Val Pro
465                 470                 475                 480

Val Ala Phe Val Val Arg Ser Asn Gly Ser Lys Ile Thr Glu Asp Glu
                485                 490                 495

Ile Lys Gln Tyr Ile Ser Lys Gln Val Ile Phe Tyr Lys Arg Ile Gly
```

```
                500              505              510
Arg Val Phe Phe Thr Glu Ala Ile Pro Lys Ala Pro Ser Gly Lys Ile
            515              520              525

Leu Arg Lys Asp Leu Arg Ala Arg Val Ser Ala Gly Asp Leu Pro Cys
            530              535              540

Thr Ser Asp Ser
545

<210> SEQ ID NO 75
<211> LENGTH: 1941
<212> TYPE: DNA
<213> ORGANISM: Glycine max
<220> FEATURE:
<223> OTHER INFORMATION: (Gm4CL)

<400> SEQUENCE: 75
```

| | | | | | |
|---|---|---|---|---|---|
| acaccacaca | cgtaaacaca | ttcagacacc | accatgataa | ctctagctcc | ttctcttgat | 60 |
| actccaaaaa | ctgatcaaaa | ccaagtttct | gatccccaaa | ctagccatgt | cttcaaatca | 120 |
| aaattaccag | atatcccaat | ctccaaccac | ctccctctcc | actcctactg | cttccagaac | 180 |
| ctctcccaat | ttgcccaccg | cccttgcctc | atcgtcggac | cgcctccaa | aaccttcacc | 240 |
| tacgccgaca | cccacctcat | ttccagcaag | atcgccgccg | gattgtccaa | cctcggaatc | 300 |
| ctcaagggcg | acgtcgtcat | gatcctcctc | cagaactccg | ccgatttcgt | cttctccttc | 360 |
| ctcgccatct | ccatgattgg | cgccgtcgcc | accaccgcca | acccgttcta | caccgccccg | 420 |
| gagatcttca | gcagttcac | cgtctccaag | gcgaagttga | tcataacaca | ggcaatgtac | 480 |
| gtggacaagc | tccgcaacca | cgacggcgcg | aagctcggcg | aggacttcaa | ggtcgtaacc | 540 |
| gtcgacgatc | cgccggagaa | ttgcctccac | ttctctgtcc | tctcggaggc | gaacgagagc | 600 |
| gacgtgccag | aggtggagat | ccaccccggac | gacgcggtgc | cgatgccgtt | ctcctccggc | 660 |
| acgacgggtt | tacctaaagg | agtgattctc | acgcacaaga | gtttaaccac | gagtgtggcg | 720 |
| cagcaagttg | acggagagaa | ccctaacctc | tacctcacca | ccgaggacgt | gctcctctgc | 780 |
| gtgcttccgc | tctttcacat | attctcgctc | aacagtgtgc | tatttgtcgc | cctcagggcg | 840 |
| gggagtgcag | ttttgttgat | gcagaagttc | gagatcggga | cactgctgga | gctgatacag | 900 |
| cggcaccgag | tgtcggtggc | gatggtggtg | ccccgctgg | tgttggcgtt | ggcaaagaat | 960 |
| ccgatggtgg | cggattttga | cctgagttca | atacggttag | tgctgtccgg | agctgctccc | 1020 |
| ttggggaagg | agctcgagga | ggctctccgg | aacaggatgc | ctcaagctgt | tttgggacag | 1080 |
| ggttacggga | tgacagaagc | agggccagtg | ctgtccatgt | gcttgggctt | tgcaaagcaa | 1140 |
| cctttccaaa | caaaatcagg | ctcttgtggt | accgtagtca | gaaatgcaga | actcaaggtt | 1200 |
| gttgaccctg | aaactggtcg | ttctcttggc | tacaatcaac | ccggtgaaat | ttgcatccga | 1260 |
| gggcaacaga | tcatgaaagg | atatctgaac | gatgaggcag | cgacagcatc | gaccatagat | 1320 |
| tcagagggtt | ggcttcacac | cggtgatgtt | ggctacgtag | atgatgatga | cgaaattttc | 1380 |
| attgttgaca | gggtgaagga | actcatcaaa | tataaaggct | tccaggtgcc | cctgcagaa | 1440 |
| cttgaagggc | ttcttgtaag | ccatccctcc | attgcagatg | cagctgttgt | cccacaaaag | 1500 |
| gatgttgctg | ctggtgaagt | tcctgttgcc | ttcgttgtga | gatcaaacgg | ctttgatcta | 1560 |
| actgaagagg | ctgtaaaaga | gtttatagct | aaacaggtag | tgttttacaa | aagactgcac | 1620 |
| aaagtttatt | ttgttcatgc | tattcccaag | tctccatcag | gaaagatatt | aaggaaagac | 1680 |
| ctcagagcaa | agctagaaac | cgccgccact | cagacgcctt | aaaggctagc | tagaacctgc | 1740 |

```
ccccttttt cttggcaata ttttccttat tttttattta tattattggt ttcacacgtg   1800
taatttacgt atcaatgctt cacggcatta agccaatccg agaagcagtt gcacttacgt   1860
ataatcattg tatttttatg tccattgtcc accaccatgt ctgtattgtg gttttagatc   1920
actaattttc gagaccttgt a                                             1941
```

<210> SEQ ID NO 76
<211> LENGTH: 562
<212> TYPE: PRT
<213> ORGANISM: Glycine max
<220> FEATURE:
<223> OTHER INFORMATION: (Gm4CL)

<400> SEQUENCE: 76

```
Met Ile Thr Leu Ala Pro Ser Leu Asp Thr Pro Lys Thr Asp Gln Asn
1               5                   10                  15

Gln Val Ser Asp Pro Gln Thr Ser His Val Phe Lys Ser Lys Leu Pro
            20                  25                  30

Asp Ile Pro Ile Ser Asn His Leu Pro Leu His Ser Tyr Cys Phe Gln
        35                  40                  45

Asn Leu Ser Gln Phe Ala His Arg Pro Cys Leu Ile Val Gly Pro Ala
50                  55                  60

Ser Lys Thr Phe Thr Tyr Ala Asp Thr His Leu Ile Ser Ser Lys Ile
65                  70                  75                  80

Ala Ala Gly Leu Ser Asn Leu Gly Ile Leu Lys Gly Asp Val Val Met
                85                  90                  95

Ile Leu Leu Gln Asn Ser Ala Asp Phe Val Phe Ser Phe Leu Ala Ile
            100                 105                 110

Ser Met Ile Gly Ala Val Ala Thr Thr Ala Asn Pro Phe Tyr Thr Ala
        115                 120                 125

Pro Glu Ile Phe Lys Gln Phe Thr Val Ser Lys Ala Lys Leu Ile Ile
    130                 135                 140

Thr Gln Ala Met Tyr Val Asp Lys Leu Arg Asn His Asp Gly Ala Lys
145                 150                 155                 160

Leu Gly Glu Asp Phe Lys Val Val Thr Val Asp Asp Pro Pro Glu Asn
                165                 170                 175

Cys Leu His Phe Ser Val Leu Ser Glu Ala Asn Glu Ser Asp Val Pro
            180                 185                 190

Glu Val Glu Ile His Pro Asp Asp Ala Val Ala Met Pro Phe Ser Ser
        195                 200                 205

Gly Thr Thr Gly Leu Pro Lys Gly Val Ile Leu Thr His Lys Ser Leu
    210                 215                 220

Thr Thr Ser Val Ala Gln Gln Val Asp Gly Glu Asn Pro Asn Leu Tyr
225                 230                 235                 240

Leu Thr Thr Glu Asp Val Leu Cys Val Leu Pro Leu Phe His Ile
                245                 250                 255

Phe Ser Leu Asn Ser Val Leu Leu Cys Ala Leu Arg Ala Gly Ser Ala
            260                 265                 270

Val Leu Leu Met Gln Lys Phe Glu Ile Gly Thr Leu Leu Glu Leu Ile
        275                 280                 285

Gln Arg His Arg Val Ser Val Ala Met Val Val Pro Pro Leu Val Leu
    290                 295                 300

Ala Leu Ala Lys Asn Pro Met Val Ala Asp Phe Asp Leu Ser Ser Ile
305                 310                 315                 320

Arg Leu Val Leu Ser Gly Ala Ala Pro Leu Gly Lys Glu Leu Glu Glu
```

```
                    325               330                335
Ala Leu Arg Asn Arg Met Pro Gln Ala Val Leu Gly Gln Gly Tyr Gly
                340                 345                350

Met Thr Glu Ala Gly Pro Val Leu Ser Met Cys Leu Gly Phe Ala Lys
            355                 360                365

Gln Pro Phe Gln Thr Lys Ser Gly Ser Cys Gly Thr Val Val Arg Asn
        370                 375                380

Ala Glu Leu Lys Val Val Asp Pro Glu Thr Gly Arg Ser Leu Gly Tyr
385                 390                 395                400

Asn Gln Pro Gly Glu Ile Cys Ile Arg Gly Gln Gln Ile Met Lys Gly
                405                 410                415

Tyr Leu Asn Asp Glu Ala Ala Thr Ala Ser Thr Ile Asp Ser Glu Gly
                420                 425                430

Trp Leu His Thr Gly Asp Val Gly Tyr Val Asp Asp Asp Glu Ile
                435                 440                445

Phe Ile Val Asp Arg Val Lys Glu Leu Ile Lys Tyr Lys Gly Phe Gln
450                 455                 460

Val Pro Pro Ala Glu Leu Glu Gly Leu Leu Val Ser His Pro Ser Ile
465                 470                 475                480

Ala Asp Ala Ala Val Val Pro Gln Lys Asp Val Ala Ala Gly Glu Val
                485                 490                495

Pro Val Ala Phe Val Val Arg Ser Asn Gly Phe Asp Leu Thr Glu Glu
                500                 505                510

Ala Val Lys Glu Phe Ile Ala Lys Gln Val Val Phe Tyr Lys Arg Leu
            515                 520                525

His Lys Val Tyr Phe Val His Ala Ile Pro Lys Ser Pro Ser Gly Lys
        530                 535                540

Ile Leu Arg Lys Asp Leu Arg Ala Lys Leu Glu Thr Ala Ala Thr Gln
545                 550                 555                560

Thr Pro

<210> SEQ ID NO 77
<211> LENGTH: 4030
<212> TYPE: DNA
<213> ORGANISM: Solanum tuberosum
<220> FEATURE:
<221> NAME/KEY: misc_feature
<222> LOCATION: (3965)..(3965)
<223> OTHER INFORMATION: n is a, c, g, or t (St4CL)

<400> SEQUENCE: 77
gtcaactttg aatgtcaatt ttgaccaatt ttttcttact ttctgtccaa atttatcgaa      60
atgtaatttg actgaacacg atattttaga aatatgaaaa actttgctta gttctatagc     120
catccttaaa agttgaagag tacacttttg tcaaataagt gagatccaat tgggatagaa     180
tattgatagt atgattaaac atttatcaaa taaaaaattg tatcgttcct ttttaaaata     240
tactaaatca aaaaaaatgt atcaggtaaa ttaagaaaaa tgattactgt ttttctttta     300
aaatcccaat tatctatcat cacctaacca taagaactac tctcaccaac cacaagagac     360
tccatttttt ttatatcccc caaaaaggaa aaaaaaattg aaacaagttt ccatgaagtt     420 gccccctgaac aaccctaaat acccataaac tccctttcac ctaccacaga cttgtgtatt    480
ttttctcata tatatattca ttaatctttg cacattcatc ttcaggacac catagctaaa     540
aatctacttt tcctttttagc ttttcagtgt gctccaattt ttttcctttt ttagctctca   600
agatgccgat ggataccgaa acaaagcaat caggagattt aatctttcga ctaaactcc      660
```

```
ctgatattta catccctaaa catttgcctt tacattctta ttgctttgaa aatctatcgg      720
agtttaattc ccggccctgt ttgattgatg gtgcaaatga tcgaatctat acttatgctg      780
aagttgaact tacttcgaga aaagttgctg ttggtcttaa caaattgggg atccaacaga      840
aggatacaat catgatcctt tgcctaatt gccctgaatt tgtgtttgcg tttattggcg       900
catcgtatct aggagcaatt tcaacaatgg ctaatcctct gtttacacca gcagaggtag      960
taaagcaagc caaagcctca agtgctaaga ttgttatcac gcaagcttgt tttgcgggga     1020
aagtgaagga ctacgcaatt gaaaatgatt tgaaggtaat atgcgtcgat tcagtaccgg     1080
aaggttgtgt tcatttctcc gaattgattc aatccgacga acacgaaatt cctgatgtga     1140
aaatccagcc ggacgatgtc gtagctctgc cgtattcctc cgggactacc gggctgccga     1200
aagggggtgat gttgacacac aaaggattag taacaagcgt tgcacaacaa gttgatggag     1260
aaaatgctaa tttgtatatg cacagcgatg atgtgttgat gtgtgtgttg cctttgttcc     1320
atatttactc actcaattct gttttgctct gtgcattgag agtcggagca gcaattttga     1380
ttatgcagaa attcgacatt gctcagtttt tagagttgat accgaagcat aaagtgacaa     1440
ttggaccatt tgttccgcct attgttctcg ccattgctaa gagtccatta gttgataact     1500
acgatctttc atcagtaaga acagtcatgt ctggtgctgc accattagga aaggaacttg     1560
aagatgccgt ccgagcaaaa ttccctaacg ccaaactcgg tcaggtaaat attattttct     1620
tttgcgtgga gttagaattt aaatttatta ttaatttacc cttaaatata aggtatacgc     1680
caaagttatt gatcttttaa tcttcatgtt cttatcctga aatacatcca tgtgctgatg     1740
cgtagtttcc caaaaacaat attttaaaga gatacactga aaccccaacc ttaccaaact     1800
cagaaaaaat ttaattttag ttacagttat agttttccta attttggagt tacaaatgta     1860
ttttgcttga cctaaggaaa tattggttgg taaacgtcta ttcttaaaaa caatgtgtac     1920
aagaatacgt gcacgccttt gtggacatat tgattttgac ttttaataat aatatatttg     1980
ccttattatg gtttcttgat agtagtgact agccagccag gatacgctgt attattttat     2040
tattgttgaa taaatttcca aatttaaatt tattggctaa ttaataaatt attaaattaa     2100
aatagggtta tggaatgacg gaagccggtc ctgtgctggc gatgtgtttg gcatttgcga     2160
aagaaccgtt tgatattaaa tcaggggcat gtggtactgt tgtgaggaac gcggagatga     2220
aaattgtgga tccggatacg ggttgctctc tgccccgtaa ccaacccggt gaaatttgca     2280
ttagaggtga tcaaatcatg aaaggtatgc taaaatcttt tgcgtgaata ttcttcgtaa     2340
acttaagtta cgtgtcaaat tagtattta gttaggtgac catttacata tatttccaaa      2400
atacacgttt ttattaggta catacgtata tagataataa cacagtttgt taagaataat     2460
aaatatacca actagtggac ctagatcaag atgcattagg ggtcattcat ataccaacag     2520
agtaaaactt atgttgattt gattaatatt tcaacgccac aaaaattgat actagcatca     2580
aaagctcacc aaccactcct accaattttt ttttaaaagc caaagaattt ttttactta      2640
ttgagtgaga ggttgatatt attaatcaga agtttaaaat taaaaaaacg cgaaaaataa     2700
aaagtatatt cttttaaaag attaaaaaag aaaagtaaa acatacaagg ttgaaacaaa      2760
gtttagagta cctttcttat tacctattga aacatgtgga gccttttacc ataaagttgt     2820
ggaactattc ggtgtatatt cattcaacca cctgcccaac tacttttcga ctttggtctt     2880
aaaaatttaa gttatcgcat atttttattc atttaattat atattaataa aaacaatgat     2940
tatttctttg taggttactt gaatgatccc gaggccacag ctagaacaat agaaaaagaa     3000
```

```
ggatggttac acactggcga tattggattc attgacgatg atgatgagct tttcattgtg   3060
gaccgattga aggaattgat caaatacaaa ggatttcaag tggcgcctgc cgagcttgaa   3120
gctcttctta tcaaccaccc cgacatttct gatgctgctg ttgtcccgta agttagttat   3180 aattttgta atgtacaact ataaatgcct aacgtacgat acagctagct caaaaatgg   3240 tctaaattct gataatttat taaattgtgt tggacagaat gatagatgaa caagcgggag   3300
aagttccagt ggcttttgtt gttagatcaa atggatctac cattactgag atgaagtca   3360 aggatttcat ctccaagcag gtttgtttca tctcgaaaca attatgtgtt tgaataaaag   3420
tgcatgtaaa cattaagtga ttcatttttg atatgttttt caaaattttg caggtgatat   3480
tctataagag aataaagcgt gtattttcg tagagacggt accaaaatct ccgtcaggaa   3540
aaattctgag aaaagattta agagctagac tggctgctgg tatttcaaat tgatggaggc   3600
aataaccaaa acaagattca ccattttag agatactata tgttgtttga tttgtacctt   3660
atgttcgatc aatataattg ccagtttggc aacggacgaa tatgtctgta aattaattta   3720
taagacttct tttattcatc ttttcatatt attatgtgat gataaggtat caaaagtatt   3780
tttttgtggg aaagaaatat atcaagagtt tgtgtttaca ttttttcttt tgtattgttc   3840
ttatattata atagttaagg tcttgctatg agttgattac acaacaaaaa ggactctcgt   3900
tgatctagtg tttaatgaaa ttagttaaaa gtcacgaggt tgaatatttt aaattttatt   3960 aaantgaaa atatgaggta attttttagt ggtcgaagaa agttaaagt atagaaaatg   4020 agtcttgatc                                                         4030
```

<210> SEQ ID NO 78
<211> LENGTH: 545
<212> TYPE: PRT
<213> ORGANISM: Solanum tuberosum
<220> FEATURE:
<223> OTHER INFORMATION: (St4CL)

<400> SEQUENCE: 78

```
Met Pro Met Asp Thr Glu Thr Lys Gln Ser Gly Asp Leu Ile Phe Arg
1               5                   10                  15

Ser Lys Leu Pro Asp Ile Tyr Ile Pro Lys His Leu Pro Leu His Ser
            20                  25                  30

Tyr Cys Phe Glu Asn Leu Ser Glu Phe Asn Ser Arg Pro Cys Leu Ile
        35                  40                  45

Asp Gly Ala Asn Asp Arg Ile Tyr Thr Tyr Ala Glu Val Glu Leu Thr
    50                  55                  60

Ser Arg Lys Val Ala Val Gly Leu Asn Lys Leu Gly Ile Gln Gln Lys
65                  70                  75                  80

Asp Thr Ile Met Ile Leu Leu Pro Asn Cys Pro Glu Phe Val Phe Ala
                85                  90                  95

Phe Ile Gly Ala Ser Tyr Leu Gly Ala Ile Ser Thr Met Ala Asn Pro
            100                 105                 110

Leu Phe Thr Pro Ala Glu Val Val Lys Gln Ala Lys Ala Ser Ser Ala
        115                 120                 125

Lys Ile Val Ile Thr Gln Ala Cys Phe Ala Gly Lys Val Lys Asp Tyr
    130                 135                 140

Ala Ile Glu Asn Asp Leu Lys Val Ile Cys Val Asp Ser Val Pro Glu
145                 150                 155                 160

Gly Cys Val His Phe Ser Glu Leu Ile Gln Ser Asp Glu His Glu Ile
                165                 170                 175
```

```
Pro Asp Val Lys Ile Gln Pro Asp Val Val Ala Leu Pro Tyr Ser
            180                 185                 190

Ser Gly Thr Thr Gly Leu Pro Lys Gly Val Met Leu Thr His Lys Gly
        195                 200                 205

Leu Val Thr Ser Val Ala Gln Gln Val Asp Gly Glu Asn Ala Asn Leu
    210                 215                 220

Tyr Met His Ser Asp Val Leu Met Cys Val Leu Pro Leu Phe His
225                 230                 235                 240

Ile Tyr Ser Leu Asn Ser Val Leu Leu Cys Ala Leu Arg Val Gly Ala
                245                 250                 255

Ala Ile Leu Ile Met Gln Lys Phe Asp Ile Ala Gln Phe Leu Glu Leu
            260                 265                 270

Ile Pro Lys His Lys Val Thr Ile Gly Pro Phe Val Pro Pro Ile Val
        275                 280                 285

Leu Ala Ile Ala Lys Ser Pro Leu Val Asp Asn Tyr Asp Leu Ser Ser
    290                 295                 300

Val Arg Thr Val Met Ser Gly Ala Ala Pro Leu Gly Lys Glu Leu Glu
305                 310                 315                 320

Asp Ala Val Arg Ala Lys Phe Pro Asn Ala Lys Leu Gly Gln Gly Tyr
                325                 330                 335

Gly Met Thr Glu Ala Gly Pro Val Leu Ala Met Cys Leu Ala Phe Ala
            340                 345                 350

Lys Glu Pro Phe Asp Ile Lys Ser Gly Ala Cys Gly Thr Val Val Arg
        355                 360                 365

Asn Ala Glu Met Lys Ile Val Asp Pro Asp Thr Gly Cys Ser Leu Pro
    370                 375                 380

Arg Asn Gln Pro Gly Glu Ile Cys Ile Arg Gly Asp Gln Ile Met Lys
385                 390                 395                 400

Gly Tyr Leu Asn Asp Pro Glu Ala Thr Ala Arg Thr Ile Glu Lys Glu
                405                 410                 415

Gly Trp Leu His Thr Gly Asp Ile Gly Phe Ile Asp Asp Asp Glu
            420                 425                 430

Leu Phe Ile Val Asp Arg Leu Lys Glu Leu Ile Lys Tyr Lys Gly Phe
        435                 440                 445

Gln Val Ala Pro Ala Glu Leu Glu Ala Leu Leu Ile Asn His Pro Asp
    450                 455                 460

Ile Ser Asp Ala Ala Val Val Pro Met Ile Asp Glu Gln Ala Gly Glu
465                 470                 475                 480

Val Pro Val Ala Phe Val Val Arg Ser Asn Gly Ser Thr Ile Thr Glu
                485                 490                 495

Asp Glu Val Lys Asp Phe Ile Ser Lys Gln Val Ile Phe Tyr Lys Arg
            500                 505                 510

Ile Lys Arg Val Phe Phe Val Glu Thr Val Pro Lys Ser Pro Ser Gly
        515                 520                 525

Lys Ile Leu Arg Lys Asp Leu Arg Ala Arg Leu Ala Ala Gly Ile Ser
    530                 535                 540

Asn
545

<210> SEQ ID NO 79
<211> LENGTH: 917
<212> TYPE: DNA
<213> ORGANISM: Solanum tuberosum
<220> FEATURE:
<223> OTHER INFORMATION: (StTHT)
```

<400> SEQUENCE: 79

```
atttctttcc tctcaaactt agctaaacaa tatctcatgg ctcctgctcc tcaacaacca      60
actccatctg aaacaataat caccgatgca tcatcggaaa acaataacgt taccatcacc     120
ggaaagatat acacacgagt ccgtctcgct acaaaatctg atctgtctca tatataccaa     180
ttgttttacc aaattcatgt ctaccataat ttcactcatt tatacaaagc tacagagtcc     240
tccttagagg gcttgctttt taaagaaaat cctcttccac ttttctacgg gccatccgta     300
cttctacttg aagtctctcc aaccccttt aacgaaccta aaataccac ggacgaaggg      360
ttcaaccccg tccttacaac gttcgacctt aaattccctg tggtagaagg acaagttgag     420
gagttccggt ccaaatatga tgataagagt gatgcttaca ttgcaggata tgctttcttt     480
tacgctaatt attcatgctt caatgacaag cctggatttt attttgagag tctttacttc     540
agagagagtt atagaaaatt gggaatgggg aaattgttgt ttggaacagt ttcgtccatt     600
gctgcggaca atggattcgt atcggtggat ggaatagtag cagtttggaa taagaagtca     660
tatgattttt acataaatat gggagttgaa attttttgatg agtttaggta tggcaaattg     720
catggtgaaa atcttcaaaa gtatgctgat aaggggaaaa ttgaggaaga gacatgttag     780
tatatagtgt tgttttattc ttataataat tgtgtaattt atcaatttct tcatatttgc     840
ttttactaaa agcagttgta ttatctttgt aattgaaatt tattaaattg attatgtatt     900
aaaaaaaaaa aaaaaa                                                     917
```

<210> SEQ ID NO 80
<211> LENGTH: 247
<212> TYPE: PRT
<213> ORGANISM: Solanum tuberosum
<220> FEATURE:
<223> OTHER INFORMATION: (StTHT)

<400> SEQUENCE: 80

```
Met Ala Pro Ala Pro Gln Gln Pro Thr Pro Ser Glu Thr Ile Ile Thr
 1               5                  10                  15

Asp Ala Ser Ser Glu Asn Asn Asn Val Thr Ile Thr Gly Lys Ile Tyr
            20                  25                  30

Thr Arg Val Arg Leu Ala Thr Lys Ser Asp Leu Ser His Ile Tyr Gln
        35                  40                  45

Leu Phe Tyr Gln Ile His Val Tyr His Asn Phe Thr His Leu Tyr Lys
    50                  55                  60

Ala Thr Glu Ser Ser Leu Glu Gly Leu Phe Lys Glu Asn Pro Leu
65                  70                  75                  80

Pro Leu Phe Tyr Gly Pro Ser Val Leu Leu Glu Val Ser Pro Thr
                85                  90                  95

Pro Phe Asn Glu Pro Lys Asn Thr Thr Asp Glu Gly Phe Asn Pro Val
            100                 105                 110

Leu Thr Thr Phe Asp Leu Lys Phe Pro Val Val Glu Gly Gln Val Glu
        115                 120                 125

Glu Phe Arg Ser Lys Tyr Asp Asp Lys Ser Asp Ala Tyr Ile Ala Gly
    130                 135                 140

Tyr Ala Phe Phe Tyr Ala Asn Tyr Ser Cys Phe Asn Asp Lys Pro Gly
145                 150                 155                 160

Phe Tyr Phe Glu Ser Leu Tyr Phe Arg Glu Ser Tyr Arg Lys Leu Gly
                165                 170                 175

Met Gly Lys Leu Leu Phe Gly Thr Val Ser Ser Ile Ala Ala Asp Asn
```

```
                180             185             190
Gly Phe Val Ser Val Asp Gly Ile Val Ala Val Trp Asn Lys Lys Ser
        195                     200                     205
Tyr Asp Phe Tyr Ile Asn Met Gly Val Glu Ile Phe Asp Glu Phe Arg
    210                     215                     220
Tyr Gly Lys Leu His Gly Glu Asn Leu Gln Lys Tyr Ala Asp Lys Gly
225                     230                     235                     240
Lys Ile Glu Glu Glu Thr Cys
                245

<210> SEQ ID NO 81
<211> LENGTH: 1607
<212> TYPE: DNA
<213> ORGANISM: Lavandula angustifolia
<220> FEATURE:
<223> OTHER INFORMATION: (LaTHT)

<400> SEQUENCE: 81
gacatagttc taagttctaa ccctctctgt cttatccctc tctaagaaga atgaagatcg      60
aaatcaaaga gtcaacgatg gtgcggccgg cggcggagac gccgagcggc agcctgtggc     120
tctcgaactt ggacttgctg tcgcggcgcga actaccacac tctgagcgtg cacttctaca     180
gccacgacgg ctcggctaac ttcttcgacg cgacggcgct gaaagaggcg ctcagccgcg     240
cgctggtcga cttctacccc tacgcgggga ggctgaagct gaataaggag aaccgcctcg     300
agatcgagtg caacggtgag gggatcttgt tggtggaggc ggagtgcagc ggcgcgttgg     360
atgagctcgg cgatttcacg ccgcggccgg agctcaacct catccctaaa gttgattact     420
ccaaggggat gtccacgtac ccgcttatgc tatttcagat aactcgtttc aaatgcggcg     480
gagtagccct cggagttgca acgagcacc acttatccga cggcgtcgcc gccctccatt      540
tcatcaacac atgggcccac tattccgcg gcgtccccgc accctcccct ccccgcact      600 tcgaccgtac cgccctctcc gcgcgtaacc ctcctcagcc gcagttcagc cacgccgaat     660
accaaccccc tcccaccctg gaaaaccctc tcccagccac cgacatcgcc cattcaaaat     720
tcaaactcac ccgcgcccag ctcaactcgc tcaaagccaa atgcgccgcc ggcgactccg     780
acggccacac aaacggcacc gctaacggca atccgacgc caacgggacc gctgacggca     840
aatccgacgc caatggaacc gctaacggca atccgcggc gaaacgatac agcacgttcg     900
aggtgctcgc cggccacatc tggcggagcg tctgcaccgc ccgcggactg ccggcggagc     960
aggagacgaa gctccacatc cccttcgacg gcagatccag actcaaccta ccgcccggct    1020
acttcggcaa cgccatcttc ttcgcgacgc cgatcgccac gtgcggcgag atcgaatcga    1080
attcgctgtc gtacgccgtc cgccgcgtcg gcgacggaat cgctcgcctc gacgaggaat    1140
acctgaaatc gtcgctcgat ttcctggaat gcagccgga catcagcaaa ttggcgcagg    1200
gggctcacag cttccggtgc cctaatttgt gggtgattag ctgggtgtgg ctgccgatct    1260
acgagccgga cttcggtgg gggaaggcgg tgcatatggg gccgtgggcg cgccgtttg    1320 aagggaagag ttatctgcta ccgaatcccg agaacgacgg cagcttgttc gtatcgatta    1380
cgcttcacaa gcagcacatg gagcggtttc agaaattgtt ctacgagatc tgatttcatc    1440
cttttttttt attaattttt atttaatttc tgcgtttggt gactttgttg tatgtgttaa    1500
ttaatttaaa tttgatgagt ttgaggaata atgaatatac agtttgaatg gtaatatcga    1560
tatggaatca atcatgagtt ttaaaaacaa aaaaaaaaa aaaaaa                     1607
```

<210> SEQ ID NO 82
<211> LENGTH: 460
<212> TYPE: PRT
<213> ORGANISM: Lavandula angustifolia
<220> FEATURE:
<223> OTHER INFORMATION: (LaTHT)

<400> SEQUENCE: 82

```
Met Lys Ile Glu Ile Lys Glu Ser Thr Met Val Arg Pro Ala Ala Glu
1               5                   10                  15

Thr Pro Ser Gly Ser Leu Trp Leu Ser Asn Leu Asp Leu Leu Ser Pro
            20                  25                  30

Ala Asn Tyr His Thr Leu Ser Val His Phe Tyr Ser His Asp Gly Ser
        35                  40                  45

Ala Asn Phe Phe Asp Ala Thr Ala Leu Lys Glu Ala Leu Ser Arg Ala
    50                  55                  60

Leu Val Asp Phe Tyr Pro Tyr Ala Gly Arg Leu Lys Leu Asn Lys Glu
65                  70                  75                  80

Asn Arg Leu Glu Ile Glu Cys Asn Gly Glu Gly Ile Leu Leu Val Glu
                85                  90                  95

Ala Glu Cys Ser Gly Ala Leu Asp Glu Leu Gly Asp Phe Thr Pro Arg
            100                 105                 110

Pro Glu Leu Asn Leu Ile Pro Lys Val Asp Tyr Ser Lys Gly Met Ser
        115                 120                 125

Thr Tyr Pro Leu Met Leu Phe Gln Ile Thr Arg Phe Lys Cys Gly Gly
    130                 135                 140

Val Ala Leu Gly Val Ala Asn Glu His His Leu Ser Asp Gly Val Ala
145                 150                 155                 160

Ala Leu His Phe Ile Asn Thr Trp Ala His Tyr Ser Arg Gly Val Pro
                165                 170                 175

Ala Pro Ser Pro Pro His Phe Asp Arg Thr Ala Leu Ser Ala Arg
            180                 185                 190

Asn Pro Pro Gln Pro Gln Phe Ser His Ala Glu Tyr Gln Pro Pro
        195                 200                 205

Thr Leu Glu Asn Pro Leu Pro Ala Thr Asp Ile Ala His Ser Lys Phe
    210                 215                 220

Lys Leu Thr Arg Ala Gln Leu Asn Ser Leu Lys Ala Lys Cys Ala Ala
225                 230                 235                 240

Gly Asp Ser Asp Gly His Thr Asn Gly Thr Ala Asn Gly Lys Ser Asp
                245                 250                 255

Ala Asn Gly Thr Ala Asp Gly Lys Ser Asp Ala Asn Gly Thr Ala Asn
            260                 265                 270

Gly Lys Ser Ala Ala Lys Arg Tyr Ser Thr Phe Glu Val Leu Ala Gly
        275                 280                 285

His Ile Trp Arg Ser Val Cys Thr Ala Arg Gly Leu Pro Ala Glu Gln
    290                 295                 300

Glu Thr Lys Leu His Ile Pro Phe Asp Gly Arg Ser Arg Leu Asn Leu
305                 310                 315                 320

Pro Pro Gly Tyr Phe Gly Asn Ala Ile Phe Phe Ala Thr Pro Ile Ala
                325                 330                 335

Thr Cys Gly Glu Ile Glu Ser Asn Ser Leu Ser Tyr Ala Val Arg Arg
            340                 345                 350

Val Gly Asp Gly Ile Ala Arg Leu Asp Glu Glu Tyr Leu Lys Ser Ser
        355                 360                 365

Leu Asp Phe Leu Glu Leu Gln Pro Asp Ile Ser Lys Leu Ala Gln Gly
```

Ala His Ser Phe Arg Cys Pro Asn Leu Trp Val Ile Ser Trp Val Trp
385                 390                 395                 400

Leu Pro Ile Tyr Glu Pro Asp Phe Gly Trp Gly Lys Ala Val His Met
            405                 410                 415

Gly Pro Trp Ala Ala Pro Phe Glu Gly Lys Ser Tyr Leu Leu Pro Asn
                420                 425                 430

Pro Glu Asn Asp Gly Ser Leu Phe Val Ser Ile Thr Leu His Lys Gln
            435                 440                 445

His Met Glu Arg Phe Gln Lys Leu Phe Tyr Glu Ile
450                 455                 460

<210> SEQ ID NO 83
<211> LENGTH: 963
<212> TYPE: DNA
<213> ORGANISM: Candida antarctica
<220> FEATURE:
<223> OTHER INFORMATION: (Lipase B)

<400> SEQUENCE: 83
atggcattgc cgtcaggttc tgacccggcc tttagccagc cgaagtctgt tctggatgct    60
ggcctgacat gtcagggtgc aagcccgtcg tccgtaagca aaccaattct gcttgtacca   120
ggcacgggca ctacgggccc gcagagcttt gattctaatt ggattcccct gtctacccag   180
cttgggtaca ccccttgttg gattagcccg cctcccttca tgctgaacga tacacaagtg   240
aatactgagt acatggtcaa cgcaattacc gcccttttatg cgggaagtgg taacaataaa   300
cttcccgtgc tgacatggag tcagggggggc ctggtggcac agtggggatt gacgttttc    360 ccatcgatcc gctcgaaagt tgatcgtctg atggcatttg cgcctgatta taaaggcaca   420
gtgctcgcgg ggccattaga tgccctggct gtgtcagcac ctagtgtctg caacagacg    480 accggttccg cgctgacgac cgccctccgg aacgcaggtg gactgaccca aattgtgccg   540
acaaccaact tgtatagcgc caccgacgaa attgttcagc cgcaggtctc caattcgcct   600
ctcgattcaa gctatctgtt taacggcaaa aatgtacagg cacaggctgt ttgcgggcca   660
ttattcgtca tcgaccatgc cggtagctta acctcccagt tcagttacgt ggttggtcgc   720
tctgccctgc gtagtaccac gggccaagcg cgctcagcgg actacggtat cactgattgc   780
aatccgttac cggcgaatga cctgactccg gaacaaaagg tagcggctgc ggcttttgtta   840 gcgccggccg ctgccgcgat tgtggcaggt cctaaacaaa actgtgaacc ggatctgatg   900
ccctatgccc gtccgtttgc ggtcggcaaa cgtacttgct caggtatcgt tacgccaagc   960
tta                                                                 963

<210> SEQ ID NO 84
<211> LENGTH: 321
<212> TYPE: PRT
<213> ORGANISM: Candida antarctica
<220> FEATURE:
<223> OTHER INFORMATION: (Lipase B)

<400> SEQUENCE: 84

Met Ala Leu Pro Ser Gly Ser Asp Pro Ala Phe Ser Gln Pro Lys Ser
1               5                   10                  15

Val Leu Asp Ala Gly Leu Thr Cys Gln Gly Ala Ser Pro Ser Ser Val
            20                  25                  30

Ser Lys Pro Ile Leu Leu Val Pro Gly Thr Gly Thr Thr Gly Pro Gln
        35                  40                  45

```
Ser Phe Asp Ser Asn Trp Ile Pro Leu Ser Thr Gln Leu Gly Tyr Thr
 50                  55                  60

Pro Cys Trp Ile Ser Pro Pro Phe Met Leu Asn Asp Thr Gln Val
 65                  70                  75                  80

Asn Thr Glu Tyr Met Val Asn Ala Ile Thr Ala Leu Tyr Ala Gly Ser
                 85                  90                  95

Gly Asn Asn Lys Leu Pro Val Leu Thr Trp Ser Gln Gly Leu Val
                100                 105                 110

Ala Gln Trp Gly Leu Thr Phe Phe Pro Ser Ile Arg Ser Lys Val Asp
            115                 120                 125

Arg Leu Met Ala Phe Ala Pro Asp Tyr Lys Gly Thr Val Leu Ala Gly
        130                 135                 140

Pro Leu Asp Ala Leu Ala Val Ser Ala Pro Ser Val Trp Gln Gln Thr
145                 150                 155                 160

Thr Gly Ser Ala Leu Thr Thr Ala Leu Arg Asn Ala Gly Gly Leu Thr
                165                 170                 175

Gln Ile Val Pro Thr Thr Asn Leu Tyr Ser Ala Thr Asp Glu Ile Val
            180                 185                 190

Gln Pro Gln Val Ser Asn Ser Pro Leu Asp Ser Ser Tyr Leu Phe Asn
        195                 200                 205

Gly Lys Asn Val Gln Ala Gln Ala Val Cys Gly Pro Leu Phe Val Ile
    210                 215                 220

Asp His Ala Gly Ser Leu Thr Ser Gln Phe Ser Tyr Val Val Gly Arg
225                 230                 235                 240

Ser Ala Leu Arg Ser Thr Thr Gly Gln Ala Arg Ser Ala Asp Tyr Gly
                245                 250                 255

Ile Thr Asp Cys Asn Pro Leu Pro Ala Asn Asp Leu Thr Pro Glu Gln
            260                 265                 270

Lys Val Ala Ala Ala Leu Leu Ala Pro Ala Ala Ala Ile Val
        275                 280                 285

Ala Gly Pro Lys Gln Asn Cys Glu Pro Asp Leu Met Pro Tyr Ala Arg
    290                 295                 300

Pro Phe Ala Val Gly Lys Arg Thr Cys Ser Gly Ile Val Thr Pro Ser
305                 310                 315                 320

Leu
```

<210> SEQ ID NO 85
<211> LENGTH: 1107
<212> TYPE: DNA
<213> ORGANISM: Clarkia breweri
<220> FEATURE:
<223> OTHER INFORMATION: (CbMOMT T133S/L322N)

<400> SEQUENCE: 85

```
atgggttcga caggcaatgc ggaaattcag atcattccga cacatagctc cgacgaagaa      60
gcgaatttgt ttgcgatgca actggcctca gctgcggttc tgcccatggc gctgaaagcc     120
gcgattgagc ttgatgtgtt agagattatg gccaaatccg taccaccaag cggctatatt     180
tcaccggccg aaattgctgc tcaactcccg acgactaatc ggaagcacc ggtcatgttg      240
gatcgcgttt gcggttact ggcgagctat tcggtagtga cgtataccct gcgtgagctg      300
ccgtctggca agtcgaacg tctgtacgga ctggcgccgg tgtgcaaatt cctgactaag     360
aatgaggatg gggtttctct cgcacccttt ctgctctcgg cgacggataa agtcctgctg      420
gaaccatggt tctacctgaa agacgccatt ctggaaggcg gcattccgtt caacaaggca     480
```

-continued

```
tacggaatga acatcttcga ttactttggc actgatcacc gcatcaacaa agtattcaac    540
aaagggatgt ctagcaatag taccatcacc atgaagaaaa ttctggagat gtacaatggg    600
tttgaaggcc tgaccaccat cgtggatgtt ggtggtggta caggcgcagt tgcctccatg    660
attgtggcga aatatccgtc gatcaatgcc attaactttg acttacccca tgtcattcag    720
gatgcgcctg cgtttagcgg tgttgaacac ttaggtgggg acatgtttga cggtgtgcca    780
aaaggcgatg cgatctttat caaatggatc tgtcatgact ggagcgatga acactgtctg    840
aaacttctta agaactgcta tgctgccttg ccggatcatg caaagtgat cgttgccgaa     900 tacattctgc ctccgtcgcc tgatccgagt attgcaacca agtagtcat ccataccgac     960 gctaacatgc tcgcctataa ccctggtgga aaagagcgta cggagaaaga attccaggca    1020
ttagcaatgg cgagtggctt cgcggtttt aaggtggcat catgcgcttt caacacctat     1080
gtgatggaat tcctgaaaac ggcctaa                                        1107
```

<210> SEQ ID NO 86
<211> LENGTH: 368
<212> TYPE: PRT
<213> ORGANISM: Clarkia breweri
<220> FEATURE:
<223> OTHER INFORMATION: (CbMOMT T133S/L322N)

<400> SEQUENCE: 86

```
Met Gly Ser Thr Gly Asn Ala Glu Ile Gln Ile Ile Pro Thr His Ser
1               5                   10                  15

Ser Asp Glu Glu Ala Asn Leu Phe Ala Met Gln Leu Ala Ser Ala Ala
            20                  25                  30

Val Leu Pro Met Ala Leu Lys Ala Ala Ile Glu Leu Asp Val Leu Glu
        35                  40                  45

Ile Met Ala Lys Ser Val Pro Pro Ser Gly Tyr Ile Ser Pro Ala Glu
    50                  55                  60

Ile Ala Ala Gln Leu Pro Thr Thr Asn Pro Glu Ala Pro Val Met Leu
65                  70                  75                  80

Asp Arg Val Leu Arg Leu Leu Ala Ser Tyr Ser Val Val Thr Tyr Thr
                85                  90                  95

Leu Arg Glu Leu Pro Ser Gly Lys Val Glu Arg Leu Tyr Gly Leu Ala
            100                 105                 110

Pro Val Cys Lys Phe Leu Thr Lys Asn Glu Asp Gly Val Ser Leu Ala
        115                 120                 125

Pro Phe Leu Leu Ser Ala Thr Asp Lys Val Leu Leu Glu Pro Trp Phe
    130                 135                 140

Tyr Leu Lys Asp Ala Ile Leu Glu Gly Gly Ile Pro Phe Asn Lys Ala
145                 150                 155                 160

Tyr Gly Met Asn Ile Phe Asp Tyr Phe Gly Thr Asp His Arg Ile Asn
                165                 170                 175

Lys Val Phe Asn Lys Gly Met Ser Ser Asn Ser Thr Ile Thr Met Lys
            180                 185                 190

Lys Ile Leu Glu Met Tyr Asn Gly Phe Glu Gly Leu Thr Thr Ile Val
        195                 200                 205

Asp Val Gly Gly Gly Thr Gly Ala Val Ala Ser Met Ile Val Ala Lys
    210                 215                 220

Tyr Pro Ser Ile Asn Ala Ile Asn Phe Asp Leu Pro His Val Ile Gln
225                 230                 235                 240

Asp Ala Pro Ala Phe Ser Gly Val Glu His Leu Gly Gly Asp Met Phe
```

-continued

```
                245                 250                 255
Asp Gly Val Pro Lys Gly Asp Ala Ile Phe Ile Lys Trp Ile Cys His
            260                 265                 270

Asp Trp Ser Asp Glu His Cys Leu Lys Leu Leu Lys Asn Cys Tyr Ala
        275                 280                 285

Ala Leu Pro Asp His Gly Lys Val Ile Val Ala Glu Tyr Ile Leu Pro
    290                 295                 300

Pro Ser Pro Asp Pro Ser Ile Ala Thr Lys Val Val Ile His Thr Asp
305                 310                 315                 320

Ala Asn Met Leu Ala Tyr Asn Pro Gly Gly Lys Glu Arg Thr Glu Lys
                325                 330                 335

Glu Phe Gln Ala Leu Ala Met Ala Ser Gly Phe Arg Gly Phe Lys Val
                340                 345                 350

Ala Ser Cys Ala Phe Asn Thr Tyr Val Met Glu Phe Leu Lys Thr Ala
            355                 360                 365
```